United States Patent
Petratos et al.

(10) Patent No.: US 10,640,748 B2
(45) Date of Patent: May 5, 2020

(54) OLIGODENDROGLIAL CELL CULTURING METHODS AND IN METHODS FOR TREATING NEURODEGENERATIVE DISORDERS BY USING THYROID HORMONES OR ANALOGUES

(71) Applicant: NeuOrphan Pty Ltd, Box Hill North, Victoria (AU)

(72) Inventors: Steven Petratos, Rowville (AU); Michael Farzad Azari, Mulgrave (AU); Jae Young Lee, Melbourne (AU); Min Joung Kim, Melbourne (AU)

(73) Assignee: NEUORPHAN PTY LTD, Box Hill North (AU)

( * ) Notice: Subject to any disclaimer, the term of this patent is extended or adjusted under 35 U.S.C. 154(b) by 0 days.

(21) Appl. No.: 15/538,150

(22) PCT Filed: Dec. 24, 2015

(86) PCT No.: PCT/AU2015/000770
§ 371 (c)(1),
(2) Date: Jun. 20, 2017

(87) PCT Pub. No.: WO2016/101017
PCT Pub. Date: Jun. 30, 2016

(65) Prior Publication Data
US 2017/0342380 A1 Nov. 30, 2017

(30) Foreign Application Priority Data
Dec. 24, 2014 (AU) .................. 2014905276

(51) Int. Cl.
*C12N 5/00* (2006.01)
*C12N 5/079* (2010.01)
*A61K 35/545* (2015.01)

(52) U.S. Cl.
CPC .......... *C12N 5/0618* (2013.01); *A61K 35/545* (2013.01); *C12N 5/0622* (2013.01); *C12N 2501/395* (2013.01); *C12N 2502/081* (2013.01); *C12N 2502/086* (2013.01); *C12N 2506/02* (2013.01)

(58) Field of Classification Search
CPC .......................... C12N 5/0618; C12N 2506/02
See application file for complete search history.

(56) References Cited

U.S. PATENT DOCUMENTS

| 7,534,765 B2 * | 5/2009 | Gregg | A61K 35/30 424/198.1 |
|---|---|---|---|
| 7,968,337 B2 | 6/2011 | Bruestle | |
| 2002/0164308 A1 | 11/2002 | Reubinoff et al. | |
| 2004/0009593 A1 | 1/2004 | Keirstead | |
| 2010/0159595 A1 | 6/2010 | Zhang | |
| 2019/0211309 A1* | 7/2019 | Rezania | C12N 5/0676 |

FOREIGN PATENT DOCUMENTS

| JP | 4090692 B2 | 5/2008 |
| WO | WO 2012/171065 | 12/2012 |

OTHER PUBLICATIONS

Printout from https://en.wikipedia.org/wiki/Oligodendrocyte_progenitor_cell. pp. 1-19, printed Jul. 3, 2019. (Year: 2019).*
Printout from https://en.wikipedia.org/wiki/Vertebrate. Printed pp. 1-9, Jul. 2019 (Year: 2019).*
Devika et al. Reproduction. 158:R97-R111. 2019 (Year: 2019).*
Ahlgren. S.C., Wallace, H., Bishop, J., Neophytou, C., and Raff, M.C. (1997). Effects of thyroid hormone on embryonic oligodendrocyte precursor cell development in vivo and in vitro. Mol Cell Neurosci g, 420-432.
Alsanie, W.F., NiCliS, J.C., and PetratOs, S. (2013). Human embryonic Stem cell-derived oligodendrocytes: protocols and perspectives. Stem Cells Dev 22, 2459-2476.
Armour, C.M., Kersseboom, S. , Yoon, G., and Visser, T.J. (2015). Further Insghts into the Allan-Herndon-Dudley Syndrome: Clinical and Functional Characterization of a Novel MCT8 Mutation. PLOS one 10, e0139343.
Baas et al. (1997), Oligodendrocyte maturation and progenitor cell proliferation are independently regulated by thyroid hormone. Glia 19, 324-332.
Baas et al. (2002), Persistence of oligodendrocyte precursor cells and altered myelination in optic nerve associated to retina degeneration in mice devoid of all thyroid hormone receptors. Proc Natl Acad Sci U S A 99.2907-2911.
Baas et al. (2000), Rat oligodendrocytes express the vitamin D(3) receptor and respond to 1,25-dihydroxyvitamin D(3). Glia 31, 59-68.
Barres, B.A., Lazar, M.A., and Raff, M.C. (1994). A novel role for thyroid hormone, glucocorticoids and retinoic acid in timing oligodendrocyte development. Development 120, 1097-1108.
Baxi, E.G., Schott, J.T., Fairchild, A.N., Kirby, L.A., Karani, R., Uapinyoying, P. , Pardo-Villamizar, C., Rothstein, J.R., Bergles, D.E., and Calabresi, P.A. (2014). A selective thyroid hormone beta receptor agonist enhances human and rodent oligodendrocyte differentiation. Glia 62, 1513-1529.

(Continued)

*Primary Examiner* — Marcia S Noble
(74) *Attorney, Agent, or Firm* — Barnes & Thornburg LLP; G. Peter Nichols

(57) ABSTRACT

The present invention relates to methods of treating or ameliorating certain neurodegenerative disorders (namely, dysmyelinating and demyelinating disorders) in patients in need of such treatment or amelioration. The invention provides methods of treating or ameliorating a patient in need of such treatment and includes the administration to the patient of: (a) thyroid hormones or thyroid hormone analogues; (b) cell replacement therapies involving the use of homogenous Oligodendrocyte Precursor Cells derived from embryonic stem cells that have been treated with thyroid hormones or thyroid hormone analogues; (c) gene therapy to correct mutated genes in vivo; or (d) a combination of two or more of (a), (b) and (c). The invention also provides compositions and formulations of thyroid hormones and thyroid hormone analogues for use in treating or ameliorating such disorders.

10 Claims, 22 Drawing Sheets

(56) References Cited

OTHER PUBLICATIONS

Bernal, J. (2007). Thyroid hormone receptors in brain development and function. Nat Clin Pract Endocrinol Metab 3, 249-259.

Biebermann, H. Ambrugger, P., Tarnow, P., von Moers, A., Schweizer. U, and Grueters, A. (2005). Extended clinical phenotype, endocrine investigations and functional studies of a loss-of-function mutation A150V in the thyroid hormone specific transporter MCT8. Eur J Endocrinol 153, 359-366.

Billon, N., Jolicoeur, C., Tokumoto, Y., Vennstrom, B., and Raff, M. (2002). Normal timing of oligodendrocyte development depends on thyroid hormone receptor alpha 1 (TRalpha1). E-mb0 J 21, 6452-6460.

Braun, D., Kim, T.D., le Coutre, P., Kohrle, J., Hershman, J.M., and Schweizer. U. (2012). Tyrosine kinase inhibitors noncompetitively inhibit tv1CT8-mediated iodothyronine transport. J Clin Endocrinol Metabo 97, E100-105.

Ceballos, A., Belinchon, M.M., Sanchez-Mendoza, E, Grijotatvlartinez, C., Dumitrescu, A.M., Refetoff, S., Morte, B., and Bernal, J. (2009). Importance of monocarboxylate transporter 8 for the blood-brain barrier-dependent avail±ility of 3,5,3'-triiodo-L-thyronine. endocrinology 150, 2491-2496.

Chaerkady, R. , Letzen, B. , Renuse, S. , Sahasrabuddhe, N.A., Kumar, P., All, A.H., Thakor, N.V., Delanghe, 3. , Gearhart, J.D., Pandey, A. , et al. (2011). Quantitative temporal proteomic analysis of human embryonic stem cell differentiation into oligodendrocyte progenitor cells. Proteomics 1 1, 4007-4020.

Chew, L.J., Shen, W.. Ming. X. , Senatorov, V.V., Jr., Chen, H.L., Cheng, Y., Hong, E. , Knoblach, S., and Gallo, V. (2011). Sry-box containing gene 17 regulates the Wnt'beta-catenin signaling pathway in oligodendrocyte progenitor cells. J Neurosci 31, 13921-13935.

Deliyanti, D. , and Wilkinson-Berka, J.L (2015). Inhibition of NOXI,'4 with GKTI 37831: a potential novel treatment to attenuate neuroglial cell inflammation in the retina. J Neuroinflammation 12, 136.

Dumitrescu, A.M., Liao, X.H., Best, T .3., Brockmann, K,, and Refetoff, S. (2004). A novel syndrome combining thyroid and neurological abnormalities is associated with mutations in a monocarboxylate transporter gene. Am J Human Genet 74, 168-175.

Dumitrescu, A.M., Liao. Weiss, R.E., Millen, K.. and Refetoff, S. (2006). Tissue-specific thyroid hormone deprivation and excess in monocarboxylate transporter (mct) a-deficient mice. Endocrinology 147, 4036-4043.

Ferrara et al., "Placenta Passage of the Thyroid Hormone Analog DITPA to Male Wild-Type and Mct8-Deficient Mice", Endocrinology, vol. 155, No. 10, Oct. 1, 2014 (Oct. 1, 2014), pp. 4088-4093, XP055475997.

Friesema, E.C., Ganguly, S. , Abdalla, A., Manning Fox, J.E.. Halestrap, A.P., and Visser, T.J. (2003). Identification of monocartoxylate transporter 8 as a specific thyroid hormone transporter. J Biol Chem 278, 40128-40135.

Friesema, E.C., Jansen, J. , Jachtenberg, J.W., Visser, W.E., Kester, M.H., and Visser, T.J. (2008). Effective cellular uptake and efflux of thyroid hormone by human monocarboxylate transporter 10. Mol Endocrinol 22, 1357-1369.

Friesema, E.C., Kuiper, G.G., Jansen, J. , Visser, T.J., and Kester, M.H. (2006). Thyroid hormone transport by the human monocarboxylate transporter 8 and its rate-limiting role in intracellular metabolism. Mol Endocrinol 20, 2761-2772.

Friesema, S.C., Grueters, A_, Biebermann, H. , Krude, H. , von Moers, A, Reeser, M., Barrett, T.G., Mancilla, E.E., Svensson, J.. Kester, M.H., et al. (2004). Association between mutations in a thyroid hormone transporter and severe X-linked psychomotor retardation. Lancet 364 1435-1437.

Gika, A.D., Siddiqui, A, Hulse, A.J., Edward, S., Fallon, P., McEntagart, M.E-., Jan, W. Josifova, D., Lerman-Sage, T., Drummond, J. , et al. (2010). White matter abnormalities and dystonic motor disorder associated with mutations in the SLC16A2 gene. Dev Med Child Neurol 52, 475-482.

Goulburn, A.L., Alden, D., Davis, R.P., Micallef, s.J., Ng, E.s., Yu, Q.c., Lim, s.M., soh, C.L., Elliott, D.A., Hatzistavrou, T.. et al. (2011). A targeted NKX2.1 human embryonic stem cell reporter line enables identification of human basal forebrain derivatives. Stem Cells 29, 462-473.

Hu, B-Y et al "Human oligodendrycytes from embryonic stem cells: conserved SHH signalling networks and divergent FGF effects", Development, vol. 136, pp. 1443-1452 (2009).

Kerr, C.L., Letzen, B.S., Hill, C.M., Agrawal, G., Thakor, N.V., Sterneckett, J.L., Gearhart, J.D., and All, A.H. (2010). Efficient differentiation of human embryonic stem cells into oligodendrocyte progenitors for application in a rat contusion model of spinal cord injury. Int J Neurosci 120, 305-313.

Kim, M et al "Efficient derivation of myelinating oligodendrocytes from NKX2.1-GFP human embryonic stem cell reporter line" Journal of Neurochemistry, vol. 134, No. Suppl. 1, Sp Iss. SI, pp. 245 (2015).

Kinne, A., Kleinau, G. , Hoefig, C.S., Gruters, A., Kohrle, J., Krause, G.. and Schweizer. U. (2010). Essential molecular determinants for thyroid hormone transport and first structural implications for monocarboxylate transporter 8. J Biol Chem 285, 28054-28063.

Laeng, P., Decimo, D.. Pettmann, B., Janet, T. , and Labourdette, G. (1994). Retinoic acid regulates the development of oligodendrocyte precursor cells in vitro. J Neurosci Res 39, 613-533.

Lee et al., "Overcoming Monocarboxylate Transporter 8 (MCT8)-Deficiency to Promote Human Oligodendrocyte Differentiation and Myelination", Ebiomedicine,vol. 25, Nov. 1, 2017 (Nov. 1, 2017),pp. 122-135, XP055475786.

Lee, J. Y et al "3,5-diiodothyropropionic acid (DITPA) promotes human oligodendrocyte differentiation and myelination" Meeting info, MS Research Australia Progress in MS Research Conference. Melbourne, Australia Oct. 29-30, 2015. Oral presentation abstract published in Multiple Sclerosis Journal, vol. 21, No. 14, p. 7 (2015).

Lopez-Espindola, D. , Morales-Bastos, C., Grijota-Madinez, C. , Liao, X.H., Lev, D. , Sugo, E., Verge, C.F., Refetoff, S. , Bernal, J. , and Guadano-Ferraz. A. (2014). Mutations of the thyroid hormone transporter MCT8 cause prenatal brain damage and persistent hypomyelination. J Clin Endocrinol Metab 99, &2799-2804.

Mayer', S., Muller, J. , Bauer, R., Richert, S. , Kassmann, C.M., Darras, V.M., Buder, K. , Boelen, A., Visser, T J. , and Heuer, H. (2014). Transporters MCT8 and OAT P ICI maintain murine brain thyroid hormone homeostasis. J Clin Invest 124, 1987-1999.

Mi et al. (2011), Death receptor 6 negatively regulates oligodendrocyte survival, maturation and myelination. Nat Med 17, 816-821.

Moog, N.K., Entringer, S., Heim, C., Wadhwa, R.D., Kathrnann, N., and Buss, C. (2015). Influence of maternal thyroid hormones during gestation on fetal brain development. Neuroscience. Published online Oct. 3, 2015.

Najm, F.J., Lager, A.M., Zaremba, A. , Wyatt, K., Caprariello, A.V., Factor, D.C., Karl, R.T., Maeda, T. , Miler, R.H., and Tesar, Pd. (2013). Transcription factor-medated reprogramming of fibroblasts to expandable, myelinogenic oligodendrocyte progenitor cells. Nat Biotechnol 31, 426-433.

Nistor et al., "Human embryonics stem cells differentiate into oligodendrocytes in high purity and myelinate after spinal cord transplantation" Glia, vol. 49, pp. 385-396 (2005).

Ostrakhovitch, S.A., Olsson, P.E., Jiang, S. , and Cherian, M.G. (2006). Interaction of metallothionein with tumor suppressor p53 protein. FEBS Lett 580, 1235-1238.

Pringle, N.P., Yu, W.P., Guthrie. S.. Roelink, H. , Lumsden, A., Peterson. A.C.. and Richardson, W.D. (1996). Determination of neuroepithelial cell fate: induction of the oligodendrocyte lineage by ventral midline cells and sonic hedgehog. Dev Biol 177, 30-42.

Sirakov, M.: Skah. S., Lone, I.N., Nac$ar, J., Angelov, D., and Plateroti, M. (2012). Multi-level interactions between the nuclear receptor T Ralphal and the WNT effectors beta-catenin!Tcf4 in the intestinal epithelium. PLOS One 7, e34162.

Sunberg et al, Stem Cell Research 5:91-103 (2010).

(56) References Cited

OTHER PUBLICATIONS

Supplementary European Search Report issued in App. No. EP15871340 (dated Jun. 7, 2018).
Thompson et al., Embryonic Stem Cell Lines Derived from Human Blastocysts, Science, vol. 282: 1145-1147 (Nov. 6, 1998).
Trajkovic, M., Visser, T", Mittag, J., Horn, S., Lukas, J., Darras, V.M.. Raivich. G.. Bauer. K., and Heuer, H. (2007). Abnormal thyroid hormone metabolism in mice lacking the monocarboxylate transporter B. J Clin Invest 117.627-635.
Vaurs-Barriere, C. , Deville, M. , Sarret, C., Giraud, G. , Des Portes, V., Prats-Vinas, J.M., De Michele: G., Dan, B., Brady, A.F., Boespflug-Tanguy: 0., et al. (2009). Pelizaeus-Merzbacher-Like disease presentation of MCT8 mutated male subjects. Ann Neurol 65, 114-118.
Verge et al., "Diiodothyropropionic acid (DITPA) in the treatment of MCT8 deficiency," J. Clin. Endocrinol. Metab., 97: 4515-4523 (2012).
Visser, T.J. (2013). Thyroid hormone transporters and resistance. Endocr Dev 24 1-10.
Visser, W.E., Friesema, E.C., Jansen, J. , and Visser, T.J. (2008). Thyroid hormone transport in and out of cells. Trends Endocrinol Metab 19.50-56.
Watkins, T.A., Emery, B. , Mulinyawe, S., and Barres, B.A. (2008). Distinct stages of myelination regulated by gamma-secretase and astrocytes in a rapidly myelinating CNS coculture system. Neuron 60, 555-569.
Wirth, E.K., Roth, S., Blechschmidt, C. , I-blter, S.M., Becker, L. , Racz, 1., Zimmer, A. , Klopstock, T. , Gailus-Durner, V., Fuchs, H., et al. (2009). Neuronal (T 3) uptake and behavioral phenotype of mice deficient in lv1ct8. The neuronal T3 transporter mutated in Allan-Herndon-Dudley syndrome. J Neurosci 29, 9439-9449.
Wosik, K. , Ante', J. , Kuhlmann, T,, Bruck, W.. Massie, B., and Nalbantoglu, J. (2003). Oligodendrocyte injury in multiple sclerosis: a role for p53. J Neurochem 85, 635-644.
Zada, D. , Tovin, A., Lerer-Goldshtein. T., Vatine. G.D., and Appelbaum, L. (2014). Altered behavioral performance and live imaging of circuit-specific neural deficiencies in a zebrafish model for psychomotor retardation. PLOS genetics 10, el 004615.
International Search Report (6 pages) dated Apr. 8, 2016 out of priority Application No. PCT/AU2015/000770.
Written Opinion (7 pages) dated Apr. 8, 2016 out of priority Application No. PCT/AU2015/000770.
International Preliminary Report on Patentability (II7 pages including Annexes) dated Apr. 18, 2017 out of priority Application No. PCT/AU2015/000770.

\* cited by examiner

Fig 1
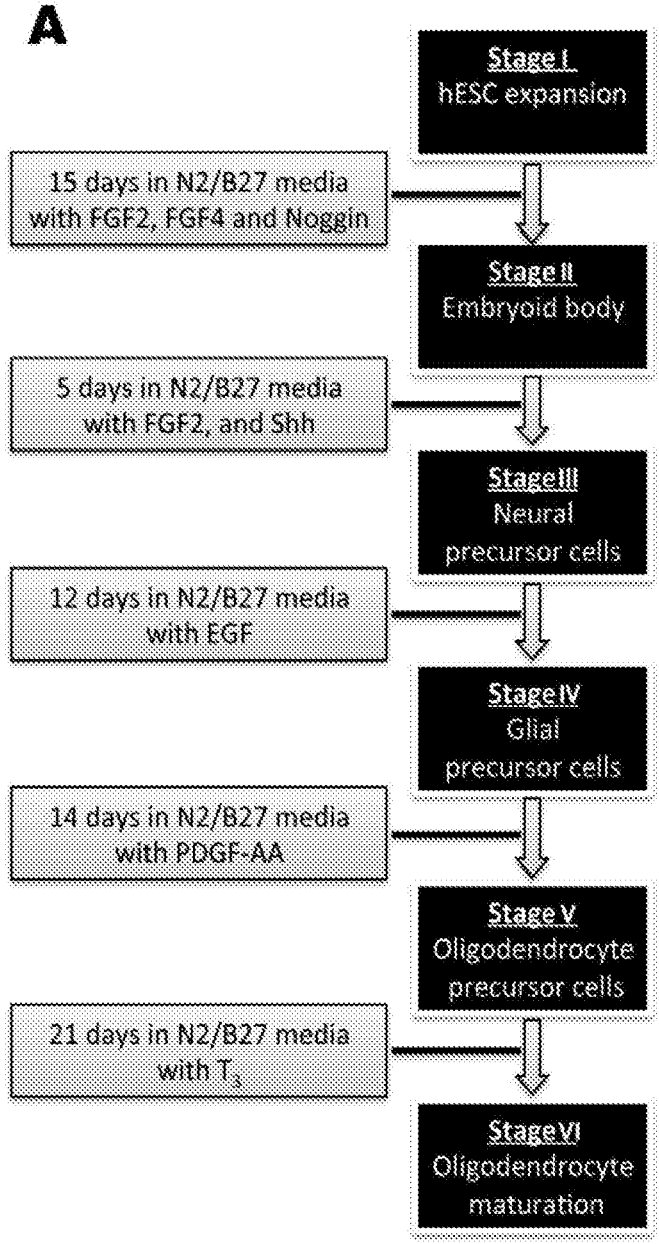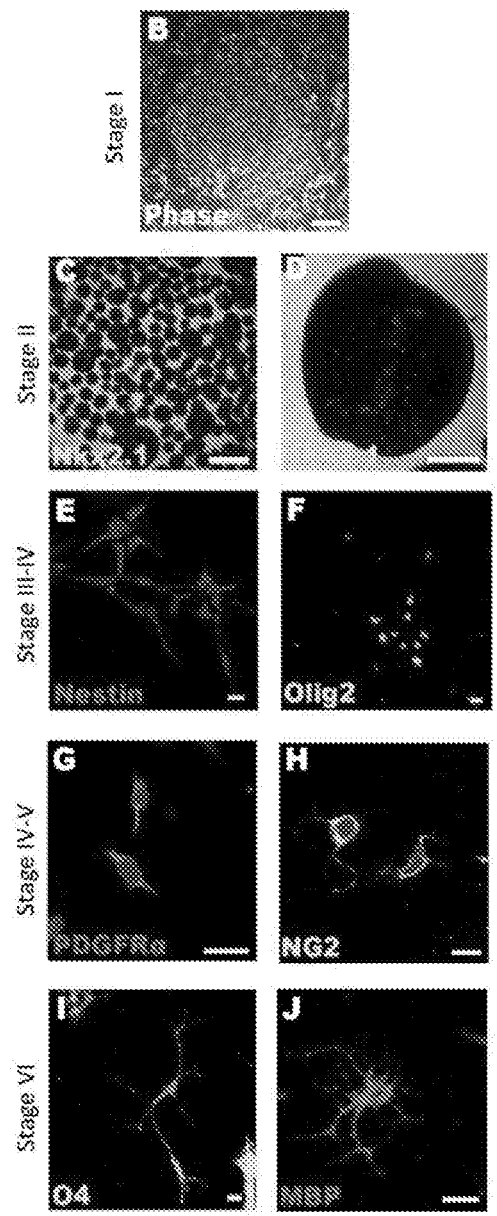

Fig 8
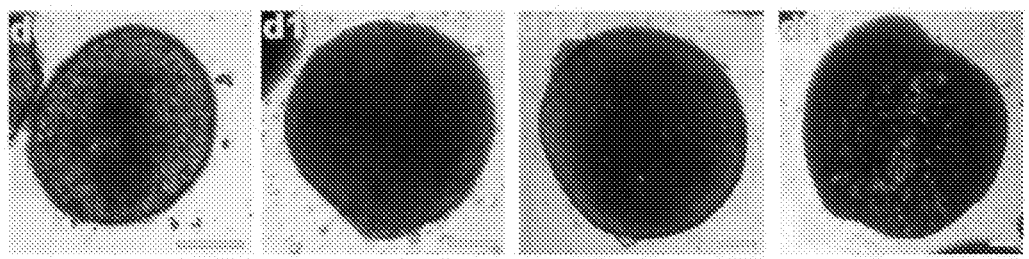
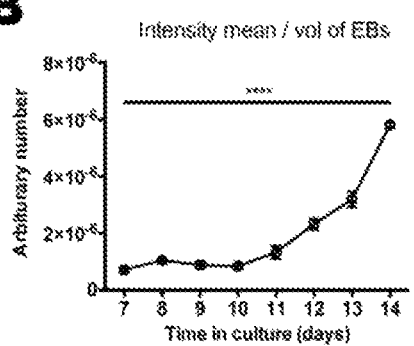
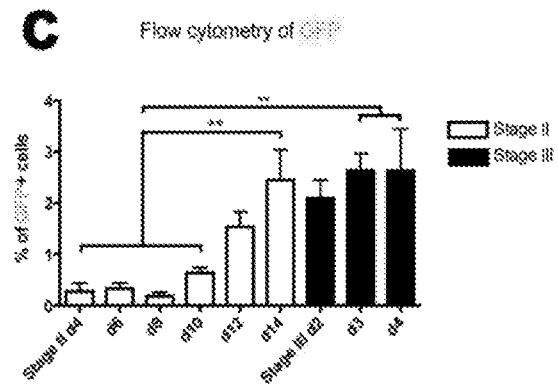
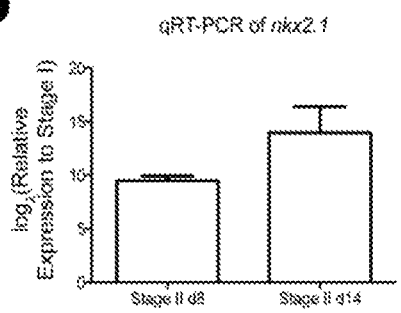
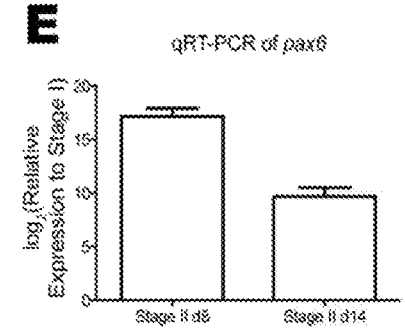

OLIGODENDROGLIAL CELL CULTURING METHODS AND IN METHODS FOR TREATING NEURODEGENERATIVE DISORDERS BY USING THYROID HORMONES OR ANALOGUES

This application claims priority to International Application No. PCT/AU2015/000770 filed Dec. 24, 2015 and to Australian Application No. 2014905276 filed Dec. 24, 2014; the entire contents of each are incorporated herein by reference.

FIELD OF THE INVENTION

The present invention relates broadly to improved methods of generating oligodendrocyte precursor cells, and to methods of treating certain neurodegenerative disorders by using thyroid hormones or thyroid hormone analogues. It has particular, although not exclusive application to improved methods for generating oligodendrocyte precursor cells from embryonic stem cells, and for the production of suitably pure cell cultures of oligodendrocyte precursor cells for use in potential cell replacement therapy or in research pertaining to certain neurodegenerative conditions in vertebrate species. Amongst other things, the invention also provides methods of treating certain neurodegenerative disorders by the use of thyroid hormones or thyroid hormone analogues, where the methods are based on an improved understanding of the biological mechanisms that are believed to be responsible for the genesis and onset of the disorders concerned.

BACKGROUND TO THE INVENTION

In vertebrates, the central nervous system (CNS) consists of two major structural elements, namely, the brain and the spinal cord. The brain in vertebrate species is normally encased within the skull. The spinal cord is continuous with the brain, and in mammals, lies disposed caudally relative to the brain and is encased within and supported by spinal vertebrae. The peripheral nervous system (PNS) comprises nerve cells that lead to and from (and which communicate with cells in) the CNS, often through junctions known as ganglia.

Within the CNS, the main cellular components of the brain and spinal cord are (1) neurons, (2) macroglia, and (3) microglia.

Neurons are the fundamental building blocks of the CNS. They are specialized cells that are electrically excitable, such that they are able to transmit information (which the CNS uses in order to monitor or control numerous body systems and functions) through electrical and chemical signalling methods communicated to receiving neurons, muscle cells or glands.

Structurally, a neuron typically comprises a cell body (which, amongst other structures, contains the cell nucleus, and thus, which stores the cell's genetic information), a main elongated extension from the cell body known as the axon, as well as one or more (and frequently, more than one) branched fine structures that protrude from the cell body, known as dendrites that are capable of forming junctions (known as synapses) with other neurons.

In many CNS neurons, the axon is covered with deposits of a fatty substance known as myelin. Myelin comprises about 40% water, and the dry mass component of the substance comprises about 70-85% lipid and about 15-30% protein. Myelin is deposited in a number of mounds along the length of the axon. When the axon portion of a myelinated neuron is viewed under a microscope, its visual appearance is not dissimilar to that of a string of sausages. On such neurons, myelin is deposited as a tubular coating along the length of the axon in structures that look like mounds, with relatively small spaces (known as "Nodes of Ranvier") defining a gap between adjoining mounds.

Electrical signals are propagated along the length of a neuron in the following way. Neurons exist in an aqueous extracellular environment that contains electrolytes (most notably, Sodium and Potassium ions). Depolarization and consequent excitation of a neuron in the vicinity of the region that bridges the cell body and the axon results in an influx of Sodium ions across the neuronal cell membrane and into the cell, which initiates an electrical signalling process (known as the "action potential") that travels along the length of the axon. In an unmyelinated axon, this electrical signal moves constantly as a wave. The function of the myelin coating (known as the "myelin sheath") in a myelinated neuron is to generate relative regions of electrical insulation between adjoining Nodes of Ranvier (because myelin, comprising fatty substances, acts as an electrical insulator). This means that in turn, the propagation of the action potential along a myelinated axon takes place by the electrical signal "jumping" from one Node of Ranvier to the next. This process, (known as "saltation") generally accelerates the velocity of the action potential along the length of the axon. Myelin additionally prevents unwanted electrical activity from interfering with the propagation of the action potential along the length of the axon to its end destination.

Many of the neurons in the CNS are myelinated. In normal subjects, myelin is deposited (via a process known as "myelination" or "myelinogenesis") in multiple tubular coating layers (known as "myelin sheaths", where—as explained earlier—adjoining sheaths are separated along the length of the axon by the Nodes of Ranvier) located on the axonal region of the neuron. The process of coating axons with myelin, is carried out by specialized macroglia known as "oligodendrocytes". Oligodendrocytes therefore play a fundamental role of communication and protection in the CNS.

Myelin is considered essential for normal neuronal function in the CNS. Indeed, myelin defects or deficiencies usually result in major neurological problems. Myelin problems can arise as a result of:
  (a) processes which interfere with myelination (such processes are generally referred to as "dysmyelination" processes); or
  (b) processes which do not interfere with myelination, but instead, which result in an attack on myelin that was previously deposited on neurons in accordance with normal myelinogenesis (these destructive processes are often referred to as "demyelination").

Dysmyelination processes (also known as leukodystrophies) often arise from hereditary mutations that affect the synthesis or the formation of myelin. In dysmyelinating conditions, myelin is either abnormally formed or cannot be maintained in its normal state because of an inherited enzymatic or metabolic disorder. One well-known medical condition arising from a dysmyelination process is Allan-Hernon-Dudley Syndrome (or 'AHDS'). AHDS is a rare X-chromosome linked recessive brain disorder (exclusively seen in males), is characterized by impaired brain development and intellectual disability. Amongst other symptoms, individuals afflicted with AHDS typically exhibit weak muscle tone, impaired muscular development, poor head control and often, a variety of faulty or involuntary movements of the arms and legs. These and other symptoms in AHDS patients typically begin in early childhood. By early adulthood, humans afflicted with AHDS have difficulty in walking independently, and many end up being wheelchair bound. AHDS is a progressive disorder.

AHDS is caused by mutations in the SLC16A2 (solute carrier family 16A2) gene. The SLC16A2 gene encodes the genetic instructions for synthesizing a protein, which in turn plays a crucial role in normal CNS development. The protein (known as Monocarboxylate Transporter 8, or MCT8) transports an endogenous hormone (triiodothyronine [also known as T3]) into neurons and glial cells in the developing brain. T3 is produced and secreted by the thyroid gland. T3 is known to be critical for the normal brain development, including normal myelination and growth of neurons and glial cells, as well as the establishment of neuronal synapses.

Demyelination usually results from certain neurodegenerative disorders. The most widely known condition of this nature is multiple sclerosis (MS). Although the exact cause of MS presently remains unknown, it is currently believed that in most instances, MS is an autoimmune-like disorder, and that in at least some forms of MS, exposure of a subject to an extrinsic pathogen (such as a bacterium or virus) or a chemical agent may be involved in its onset. As part of the autoimmune response, inflammatory cells invade the CNS, causing damage to the brain, spinal cord, and/or the optic nerves. In particular, the inflammatory cells target and damage the protective myelin sheath that coats myelinated neurons. This damage causes the formation of scars (called 'plaques' or 'lesions') on the affected neuronal tissue, which interfere with the normal processes of neuronal transmission.

The clinical symptoms exhibited by subjects afflicted with MS can be significant, and typically include the following (amongst others):
  (a) fatigue, which often manifests as a feeling of debilitation that is disproportionate to an activity in which the subject is engaged;
  (b) balance and co-ordination problems;
  (c) pain;
  (d) speech abnormalities;
  (e) psychological or emotional disturbances; and
  (f) blindness.

There is currently no known cure for either dysmyelinating or demyelinating conditions. In particular, there are presently no therapies known which would address the myelin defects or deficiencies that cause, or are involved in the development of these conditions, or of other conditions (eg, spinal cord injury), where remyelination or repair/replacement of damaged myelin would be highly desirable, if that were possible. Specifically, re-myelination (ie, "myelin repair" or "myelin replacement") is not a possibility on the current state of scientific knowledge. In humans, myelination begins in the third trimester of gestation, and the overwhelming majority of the myelination process is therefore completed by the adolescent years. In subjects who either suffer spinal cord injury (SCI) or who suffer from a dysmyelinating or demyelinating condition, the prevailing wisdom has been that the state of medical knowledge therefore offers little if any realistic hope for cures to these degenerative conditions.

In the last decade or so, stem cell science has offered new hope for the treatment of some conditions that were previously considered untreatable. In the context of dysmyelinating and demyelinating conditions in humans, it has been postulated that if human oligodendrocyte precursor cells (hOPC) could be generated from human embryonic stem cells (hESC), hOPCs generated in this manner could be used as part of a cell replacement therapy (CRT) in humans who suffer from either a dysmyelinating or a demyelinating condition.

hESCs are derived from the inner cell mass of the blastocyst from the pre-implantation stage of the human embryo, and are "pluripotent" (Thompson et al., 1998), meaning that they can differentiate into any cell type derived from the three primary germ layers: ectoderm, mesoderm and endoderm. Each corresponding germ layer has the potential to differentiate into different compartments of the body. Ectoderm derivatives include neural and epithelial lineage cells.

Despite the optimism pertaining to the use of hESCs as a potential source of large numbers of exogenous OPCs for CRT, to date an established protocol for generating acceptably homogenous populations of OPCs that are able to myelinate efficiently does not exist. An established protocol to generate pure populations of hESC-derived oligodendrocytes would advance the quality of any future clinical trials of CRT in conditions involving dysmyelination or demyelination. This would provide a potential therapeutic strategy for individuals (male or female) suffering from delayed myelination conditions, such as AHDS, Pelizaeus-Merzbacher disease (PMD), Canavan disease and Alexander disease (amongst other leukodystrophies). Importantly, the possibility for therapeutic interventions also exists for acute and chronic demyelination, such as occurs in MS and SCI.

hOPCs can be experimentally derived from hESCs in culture in the presence of specific growth factor-defined conditions in a culture medium. The desired outcome of hESC-derived oligodendrocyte differentiation is to obtain a sufficient yield of acceptably homogeneous populations of OPCs to be utilized for potential CRT. However, such an outcome has not yet been achieved, due to current gaps in scientific knowledge and understanding surrounding ex vivo oligodendrogenesis.

Although therapies have in the past been proposed for treating or alleviating some dysmyelinating and demyelinating conditions by using certain thyroid hormones or their analogues, the biological mechanisms responsible for the genesis and onset of such conditions have hitherto not been well understood, and hence, the previously attempted treatments are unlikely to have been as effective as they could be. Accordingly, and while a number of approaches have been used to date to use thyroid hormones or their analogues to treat such conditions, an inadequate understanding of the responsible biological mechanisms at play has hampered the development of suitable or more effective therapies for those conditions.

The present invention therefore aims to alleviate at least one of these problems, and to provide improved methods of generating acceptably homogeneous populations of OPCs for use in research or potentially for use in CRT, as well as aiming to provide methods of treating dysmyelinating and/or demyelinating conditions that are based on an improved understanding of the biological mechanisms responsible for causing them.

SUMMARY OF THE INVENTION

The present invention is based on the finding that at the sub-cellular level, in ways that were not previously understood, thyroid hormones play an important role in the differentiation of oliogodendrocyte precursor cells (OPCs) into myelinating oligodendrocytes, and that dysmyelinating and demyelinating neurodegenerative disorders can therefore be prevented, alleviated or treated by treating a patient with:
  (a) thyroid hormones or thyroid hormone analogues;
  (b) CRT involving the use of homogenous OPCs derived from embryonic stem cells that have been treated with thyroid hormones or thyroid hormone analogues;
  (c) gene therapy to correct mutated genes in vivo;
  (d) a combination of two or more of (a), (b) and (c).

In a first aspect, the present invention therefore generally provides a method of generating at least one vertebrate oligodendrocyte precursor cell (OPC) from at least one vertebrate embryonic stem cell, the method comprising the steps of:
  (a) culturing the at least one vertebrate embryonic stem cell in a culture medium;
  (b) administering a thyroid hormone or a thyroid hormone analogue to the at least one vertebrate embryonic stem cell in the culture medium in an amount or at a concentration which is effective to cause the at least one vertebrate embryonic stem cell to undergo differentiation to an oligodendrocyte precursor cell; and
  (c) Incubating the at least one vertebrate embryonic stem cell in presence of the thyroid hormone or thyroid hormone analogue in the culture medium under conditions which enable the at least one vertebrate embryonic stem cell to differentiate into one or more oligodendrocyte precursor cells.

In a second aspect, the invention further generally provides a method of differentiating at least one vertebrate embryonic stem cell so as to give rise to at least one oligodendrocyte precursor cell, the method comprising the steps (a) to (c) described in the preceding paragraph.

In a third aspect, the invention yet further generally provides at least one vertebrate oligodendrocyte precursor cell, the cell having been derived via either of the methods described in the preceding two paragraphs. Preferably further, the at least oligodendrocyte precursor cell is one of many such cells forming part of a cell line.

Preferably further, the at least one vertebrate oligodendrocyte precursor cell has the potential to myelinate (or is capable of myelinating) at least one neuron in a subject.

It is to be understood that wherever appearing in this specification, the terms 'patient' and 'subject' are used interchangeably, and mean the same thing.

Preferably, the vertebrate is a mammal. Preferably further, the mammal is a human. In some embodiments of the invention however, the mammal may be an animal other than a mammal. So, for example, the vertebrate may (without limiting the concept of what is a vertebrate) be a bird, fish or reptile. In those embodiments where the vertebrate is a mammal, the vertebrate may be a non-human mammal.

Preferably, the at least one vertebrate embryonic stem cell is a human embryonic stem cell (hESC). Preferably further, the hESC is derived from the ectodermal layer. In some embodiments, it is particularly preferred that the hESC is a hESC-derived Nkx2.1-positive reporter cell or a Hes3 reporter cell. In other preferred embodiments, the at least one vertebrate embryonic stem cell may include at least one H9 human embryonic cell, amongst other possible cell candidates. In yet other preferred embodiments, the at least one vertebrate embryonic stem cell may include at least one cell from the United States National Institute of Health approved H9 hESC line (Catalogue No. SCR600 or CS204496; Merck Millipore).

Preferably, the thyroid hormone or a thyroid hormone analogue is 3,5-Diiodothyropropionic acid (DITPA), whose chemical structure is shown below:

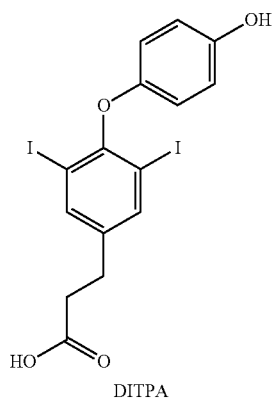 [SMILES: O=C(O)CCc1cc(I)c(Oc2ccc(O)cc2)c(I)c1]

DITPA

In alternative embodiments, the thyroid hormone or a thyroid hormone analogue may be:
  (a) 3,5-dimethyl-4-(4'-hydroxy-3'-isopropylbenzyl)-phenoxy acetic acid (GC-1);

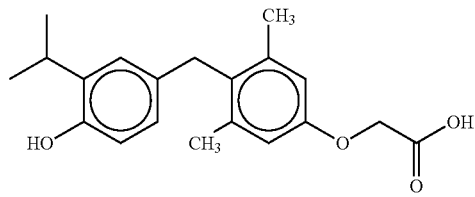

(b) tetraiodothyro acetic acid (TETRAC); or

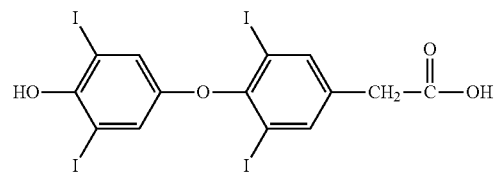 [SMILES: O=C(O)Cc1cc(I)c(Oc2cc(I)c(O)c(I)c2)c(I)c1]

(c) triiodothyroacetic acid (TRIAC).

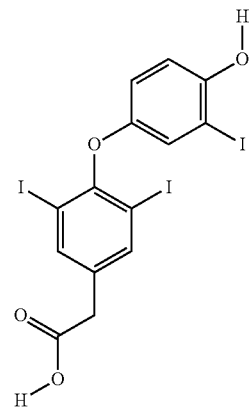 [SMILES: O=C(O)Cc1cc(I)c(Oc2ccc(O)c(I)c2)c(I)c1]

Preferably, the thyroid hormone or thyroid hormone analogue is administered at a concentration in the culture medium of from between 1 and 100 nanograms per millilitre (ng/mL). It is further preferred that thyroid hormone or thyroid hormone analogue is administered at a concentration in the culture medium of from between 1 and 10 ng/mL. It is especially preferred that the thyroid hormone or thyroid hormone analogue is administered at a concentration in the culture medium of about 10 ng/mL.

The culture medium is a predominantly aqueous environment. Preferred aqueous environments include water, physiological saline solutions, and other biologically acceptable aqueous environments for the culture of vertebrate cells. Some substances that are suitable as thyroid hormones or thyroid hormone analogues for the purposes of the invention may be insoluble or sparingly soluble in water or aqueous culture media of the kind, which persons of skill in the art would apprehend as being suitable for use in connection with the present invention. Preferably, where the thyroid hormone or thyroid hormone analogue is insoluble or sparingly soluble in such aqueous environments, the thyroid hormone or thyroid hormone analogue is first dissolved in another solvent before it is administered to the culture medium. A suitable other solvent for this purpose would include ethanol, although other chemical solubilizing agents and indeed, other solubilisation techniques (eg, milling of solid forms of the thyroid hormone or thyroid hormone analogue so as to enhance their solubility in such aqueous environments) are also embraced within the scope of the invention.

Preferably, the conditions which enable the at least one vertebrate embryonic stem cell to differentiate into one or more oligodendrocyte precursor cells include incubating the at least one vertebrate embryonic stem cell in the presence of the thyroid hormone or thyroid hormone analogue for between 24 hours and 3 months.

A preferred incubation period is between 48 hours and 3 months. A particularly preferred incubation period is between 7 days and 3 months.

Preferably further, the conditions which enable the at least one vertebrate embryonic stem cell to differentiate into one or more oligodendrocyte precursor cells include the step of incubating the at least one embryonic stem cell in a culture medium that comprises at least one substance which acts as a promoter of oligodendrocyte growth and/or division. Preferred growth factors for this purpose include:
  (a) PDGF (platelet-derived growth factor); and
  (b) CNTF (ciliary neurotrophic factor) according to Sunberg et al., 2010 Stem Cell Research 5:91-103;
  (c) EGF (epidermal growth factor); and
  (d) FGF (fibroblast growth factor); and
  (e) Sonic Hedgehog.

In preferred embodiments, the conditions which enable the at least one vertebrate embryonic stem cell to differentiate into one or more oligodendrocyte precursor cells include the step of incubating the at least one embryonic stem cell in a culture medium that comprises two or more such growth factors.

Preferably, the method according to the present invention, of generating at least one vertebrate oligodendrocyte precursor cell from at least one vertebrate embryonic stem cell, comprises the following steps:
  (1) Formation of a three-dimensional mass of the embryonic stem cell or cells through a cell proliferation stage;
  (2) Generating one or more embryoid bodies from at least one proliferating embryonic stem cell;
  (3) Commencing conversion of the embryonic stem cell or cells into a monolayer of neural precursor cells through the addition of sonic hedgehog (shh);
  (4) Promoting conversion of the neural precursor cells to one or more glial precursor cells;
  (5) Promoting the conversion of the one or more glial precursor cells to one or more oligodendrocyte precursor cells; and
  (6) Differentiating the one or more oligodendrocyte precursor cells toward post-mitotic cells capable of myelination.

Preferably, in stage (1), bFGF (basic fibroblast growth factor, also known as FGF2), is added to the culture medium, so that the embryonic stem cells form a three-dimensional embryoid body. This process typically takes up to 7 days. During this stage, bFGF is administered to the cells, which are typically suspended on a substrate material. A preferred substrate material for this purpose is Matrigel™ (a gelatinous protein mixture secreted by Engelbreth-Holm-Swarm mouse sarcoma cells, produced and marketed by Corning Life Sciences). Preferably, the bFGF is added to the cells to achieve a concentration of about 20 ng/mL.

In stage (2), hESC cultures are dissociated using collagenase type IV, then collected and resuspended in serum-free medium supplemented with bFGF (at a concentration of about 20 ng/mL), FGF4 (at a concentration of about 20 ng/mL), and Noggin (at a concentration of about 200 ng/mL). Resuspended cells are then placed onto non-adherent plates to form embryoid bodies (EBs), which are grown for 14 days.

In stage (3), a monolayer of embryonic stem cells is established on Matrigel™-coated plates cultured in medium containing bFGF and Sonic hedgehog for 5 days in order to differentiate them into neural precursor cells. Preferably, for this purpose, the cells are cultured in bFGF at a concentration of about 20 ng/mL. It is further preferred that the concentration of Sonic hedgehog in the culture medium is about 100 ng/mL.

In stage (4), the cells are detached using accutase (supplied by Life Technologies) and plated onto Matrigel™ coated plates in culture medium containing EGF. These cells are fed daily over a period of about 12 days to induce the formation of glial progenitor cells. Preferably, the concentration of EGF in the culture medium is about 20 ng/mL.

In stage 5, the cells are detached using accutase and then plated for 14 days onto Matrigel™ coated plates in culture medium containing PDGF in order to induce the formation of OPCs. Preferably, in this stage:
  (a) The PDGF used is in the form of PDGF-AA; and
  (b) The PDGF-AA is present in the culture medium at a concentration of about 20 ng/mL.

In stage (6), for terminal differentiation, the cells are plated with poly-L-ornithine (at a concentration of about 10 µg/mL) (Supplier: Sigma-Aldrich) and mouse laminin (at a concentration of about 10 µg/mL) (Supplier: Life technologies) coated plates in culture medium supplemented with a thyroid hormone or thyroid hormone analogue, for about 21 days, in order to induce premyelinating-oligodendrocytes. In preferred embodiments, the thyroid hormone or thyroid hormone analogue is DITPA, which is present at a concentration range of 1 ng/mL to 100 ng/mL. Preferably, the concentration of DITPA is about 10 ng/mL.

In a fourth aspect, the present invention also generally provides a culture medium for promoting the differentiation of at least one embryonic stem cell, the culture medium comprising:
(a) At least embryonic stem cell;
(b) A thyroid hormone or thyroid hormone analogue;
(c) A substantially aqueous solution; and
(d) At least one growth factor selected from the group comprising:
(1) PDGF (platelet-derived growth factor);
(2) CNTF (ciliary neurotrophic factor) (See Sunberg et al., 2010 *Stem Cell Research* 5:91-103);
(3) EGF (epidermal growth factor);
(4) FGF (fibroblast growth factor); and
(5) Sonic hedgehog,
in a solution that is suitable for culturing the at least one cell.

Preferred solutions for this purpose are aqueous solutions of the kinds discussed previously.

Preferred culture media for the purposes of this aspect of the invention would include at least one growth factor for oligodendrocytes, Preferred growth factors for this purpose include:
(a) PDGF (platelet-derived growth factor);
(b) CNTF (ciliary neurotrophic factor);
(c) EGF (epidermal growth factor);
(d) FGF (fibroblast growth factor), and
(e) shh (sonic hedgehog), as discussed previously.

In a fifth aspect, the present invention further generally provides the use of at least one oligodendrocyte precursor cell derived via (either of the methods described above in the manufacture of a medicament for treating a subject or patient suffering from a neurological condition caused by (or associated with) myelin deficiency.

In a sixth aspect, the present invention generally provides a method of treating or ameliorating a neurological disorder associated with MCT8 deficiency or impairment in a patient in need of such treatment or amelioration, the method comprising the step of administering to the patient, an effective amount of a thyroid hormone or thyroid hormone analogue of the kinds previously described.

In this aspect of the present invention, the thyroid hormone or analogue may be any of the agents previously discussed. Preferably however, the thyroid hormone or analogue is, or comprises, DITPA.

Further, in this aspect of the present invention, the neurological disorder associated with MCT8 deficiency or impairment may be one:
(a) that arises in the patient via genetic or hereditary means; or
(b) arises in the patient after conception or birth other than via genetic or hereditary means, such as through an acquired injury or disease.

Preferably in this aspect of the invention, the patient is a mammal. In certain preferred embodiments of the present invention, the patient is a human being. In some particular embodiments of the invention, the patient may be:
(a) an adult human being (meaning a human that has attained the age of 18 years);
(b) an infant or minor (meaning a human that has not yet attained the age of 18 years); or even
(c) a foetus that has not yet been born.

In yet further preferred embodiments of the invention, the patient may be a non-human animal. The non-human animal patient in such embodiments may be either an adult, an animal which has yet to reach adulthood, and even a foetus.

Poor myelination is a common finding in the brains of human babies born either prematurely, after chronic foetal hypoxia and foetal growth-retardation, or after a birth where oxygen deprivation has occurred or as a consequence of genetically inherited hypomyelination syndromes. Less common, but of more serious concern is the presence of frank white matter injury, sometimes present as cystic lesions. Hitherto, there has been no treatment for reduced myelination or these white matter injuries in babies, and myelination deficits appear to have been life-long and not amenable to repair by endogenous brain growth mechanisms. Therapies that directly target these conditions should be based on an understanding of the fundamental mechanisms that underlie the impaired myelination, and they should therefore preferably interrogate the maturation of oligodendrocytes from their early stage as a pluripotent progenitor cell to their attainment of their own cellular machinery to produce and lay down myelin. The presence of diffuse or cystic lesions in the brain of some pre-term infants suggests that the principal event is a loss of cells in white matter as a result of cytolytic processes initiated or exacerbated by hypoxia, ischaemia, and/or inflammation, and there is a corpus of evidence that this arises from a vulnerability of precursor oligodendrocytes to cell death {Stephen Back, 2002 #12; Back, 2005 #526; Volpe, 2008 #542}.

Whilst in humans, thyroid hormones can be transported across the placental barrier, in thyroid hormone-resistant conditions, such as AHDS, the toxic effects of T3 deprivation at the critical developmental stages within the brain will limit time-specific maturation of the foetal brain, causing psychomotor retardation. The key periods for the activity of thyroid hormones in the developing foetal brain are within the second trimester onward, where the maternal circulating thyroid hormone elevates and is then contributed to by the development and functionality of the foetal thyroid gland.

Assessment and diagnosis as to whether a given foetus requires treatment to prevent or ameliorate a thyroid hormone deficiency can be made from 17 weeks gestation onwards, by foetal DNA extracted from chorionic villi then followed by next genome sequencing techniques performed to validate the thyroid hormone resistance profile of the foetus.

In this aspect of the invention, the neurological disorder may be either a dysmyelinating condition, or a demyelinating condition. Examples of dysmyelinating conditions amenable to treatment via the method of this aspect of the invention include:
(a) AHDS,
(b) Pelizaeus-Merzbacher disease,
(c) Canavan disease,
(d) Alexander disease, and
(e) other leukodystrophies.

An example of a demyelinating disorder that is amenable to treatment via this second aspect of the invention is Multiple Sclerosis.

In the method in accordance with this sixth aspect of the invention, the thyroid hormone or thyroid hormone analogue may be administered to the patient via any suitable method of administration. Preferred methods of administration for this purpose include:
(a) topical administration (ie, where the thyroid hormone or thyroid hormone analogue is applied directly where its action is desired);
(b) enteral administration; and
(c) parenteral administration.

Examples of topical routes of administration having a local effect include epicutaneous (onto the skin) and intravitreal (into the eye). All such forms of administration are embraced within the scope of the present invention.

Wherever used in this specification, references to 'enteral' administration mean that the thyroid hormone or thyroid hormone analogue is administered to the patient via the digestive tract, with the objective that the effect of such administration is systemic within the patient. For this purpose, the term 'systemic' is to be understood as meaning that the effect of the thyroid hormone or thyroid hormone analogue so administered may be either local or non-local in the patient. Enteral administration therefore includes the oral administration of suitable pharmaceutical compositions, preparations or formulations of thyroid hormones or thyroid hormone analogues to the patient in ways and by means that would readily be understood by ordinary persons of skill in the field of the present invention.

Examples of enteral routes of administration having a systemic (non-local) effect include any form of administration that involves any part of the gastrointestinal tract, such as oral (into the mouth), intranasal (into the nose), rectal (into the rectum), and vaginal (into the vagina). All such forms of administration are embraced within the scope of the present invention.

Wherever used in this specification, references to 'parenteral' administration mean that the thyroid hormone or thyroid hormone analogue is administered to the patient in ways other than via the digestive tract (and other than topically).

Examples of parenteral administration include by injection, infusion, implantation or diffusion having a systemic effect, intravenous (into a vein), intraarterial (into an artery), intramuscular (into a muscle), intracardiac (into the heart), subcutaneous (under the skin), percutaneous (via needle-puncture into the skin), intradermal (into the skin itself), intrathecal (into the spinal canal), intraperitoneal (infusion or injection into the peritoneum), intravesical infusion (infusion into the urinary bladder), epidural (injection or infusion into the epidural space), transdermal or transcutaneous (diffusion through the intact skin), transmucosal (diffusion through a mucous membrane), insufflation (diffusion through the nose), inhalational (diffusion through the mouth), sublingual (under the tongue), and buccal (absorbed through cheek near gumline). All such forms of administration are embraced within the scope of the present invention.

Enteral and parenteral routes of administration are generally preferred. In some embodiments, orally into the mouth is preferred. In some other embodiments, injection or infusion is preferred. In these latter embodiments, intravenous (into a vein), intra-arterial (into an artery), intramuscular (into a muscle), subcutaneous (under the skin), percutaneous (via needle-puncture into the skin), intradermal (into the skin itself), transdermal or transcutaneous (diffusion through the intact skin), sublingual (under the tongue), and buccal (absorbed through cheek near gumline) parenteral routes of administration are generally preferred.

In this sixth aspect of the invention, the thyroid hormone or thyroid hormone analogue is preferably formulated for administration to the patient in accordance with the route of administration appropriate in the patient's circumstances.

As explained earlier, in preferred embodiments, the thyroid hormone or thyroid hormone analogue is preferably DITPA.

Pharmaceutical compositions comprising DITPA suitable for use in the invention may take any of a number of administration forms (see, for example, *Pharmaceutics and Pharmacy Practice*, J. B. Lippincott Company, Philadelphia, Pa., Banker and Chalmers, eds., pages 238-250 (1982)).

Depending on the intended or preferred mode of administration, a pharmaceutical composition comprising DITPA suitable for use in the invention may take the form of a solid, semi-solid, or liquid, such as, for example, a tablet, a capsule, a caplet, a liquid, a suspension, an emulsion, a gel, a suppository, granules, pellets, beads, a powder, or the like, preferably in unit dosage form suitable for single administration of a precise dosage.

Suitable pharmaceutical compositions and dosage forms may be prepared using conventional methods known to those in the field of pharmaceutical formulation and described in the pertinent texts and literature, (see, for example, Remington J. P., *The Science and Practice of Pharmacy*, ed. A. R. Gennaro, $20^{th}$ Edition, Lippincott, Williams and Wilkins Baltimore, Md. (2000)). Examples of oral dosage forms include, but are not limited to, tablets, capsules, caplets, solutions, suspensions, and syrups, and may also comprise a plurality of granules, beads, powders, or pellets that may or may not be encapsulated. Preferred oral dosage forms are tablets, capsules, solutions, suspensions, and syrups. Any of these oral dosage forms may be mixed with food or beverages.

Tablets comprising thyroid hormones or analogues (such as DITPA) of the kind embraced by the invention may be manufactured using standard tablet processing procedures and equipment, of the kind that would readily be understood by those of ordinary skill in the art. Direct compression and granulation techniques are preferred. In addition to the active agent, tablets will generally also contain inactive, pharmaceutically acceptable carrier materials such as binders, lubricants, disintegrants, fillers, stabilisers, surfactants, colouring agents, and the like. Binders are used to impart cohesive qualities to a tablet, and thus ensure that the tablet remains intact. Suitable binder materials include, but are not limited to, starch (including corn starch and pregelatinized starch), gelatin, sugars (including sucrose, glucose, dextrose, and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethyl cellulose, and the like), and Veegum™. Lubricants are used to facilitate tablet manufacture, promoting powder flow and preventing particle capping (i.e. particle breakage) when pressure is relieved. Useful lubricants are magnesium stearate, calcium stearate, and stearic acid. Disintegrants are used to facilitate disintegration of the tablet, and are generally starches, clays, celluloses, algins, gums, or crosslinked polymers. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Stabilisers, as well known in the art, are used to inhibit or retard drug decomposition reactions that include, by way of example, oxidative reactions.

For manufacturing capsules, the active agent-containing composition may be encapsulated in the form of a liquid or solid (including particulates such as granules, beads, powders, or pellets). Suitable capsules may be either hard or soft, and are generally made of gelatin, starch, or a cellulosic material, with gelatin capsules generally being preferred. Two-piece hard gelatin capsules are preferably sealed, such as with gelatin bands or the like. (See, for example, Remington J. P., *The Science and Practice of Pharmacy*, ed. A. R. Gennaro, $20^{th}$ edition, Lippincott, Williams and Wilkins Baltimore, Md. (2000), which describes materials and methods for preparing encapsulated pharmaceuticals).

Oral dosage forms, whether tablets, capsules, caplets, or particulates, may, if desired, be formulated so as to provide for gradual, sustained release of the active agent over an extended time period. Generally, as will be appreciated by those of ordinary skill in the art, sustained release dosage forms are usually formulated by dispersing the active agent within a matrix of a gradually hydrolyzable material such as a hydrophilic polymer, or by coating a solid, drug-containing dosage form with such a material. Hydrophilic polymers useful for providing a sustained release coating or matrix include, by way of example: cellulosic polymers such as hydroxypropyl cellulose, hydroxyethyl cellulose, hydroxypropyl methyl cellulose, methyl cellulose, ethyl cellulose, cellulose acetate, and carboxymethylcellulose sodium; acrylic acid polymers and copolymers, preferably formed from acrylic acid, methacrylic acid, acrylic acid alkyl esters, methacrylic acid alkyl esters, and the like, e.g. copolymers of acrylic acid, methacrylic acid, methyl acrylate, ethyl acrylate, methyl methacrylate and/or ethyl methacrylate; and vinyl polymers and copolymers such as polyvinyl pyrrolidone, polyvinyl acetate, and ethylene-vinyl acetate copolymer.

Pharmaceutical compositions for parenteral administration include sterile aqueous and non-aqueous solutions, suspensions, and emulsions. Injectable aqueous solutions contain DITPA in water-soluble form. Examples of non-aqueous solvents or vehicles include fatty oils, such as olive oil and corn oil, synthetic fatty acid esters, such as ethyl oleate or triglycerides, low molecular weight alcohols such as propylene glycol, synthetic hydrophilic polymers such as polyethylene glycol, liposomes, vesicles, nanoparticles, and the like. DITPA is sparingly soluble in water and aqueous solutions, and so the formulation of aqueous solutions for injection will typically require assistance to solubilise the substance in water. One technique for this purpose is to solubilise it using a formulation technology such as Captisol®.

Vesicle and/or nanoparticle preparations may be prepared with many different conventional ingredients, including, but not limited to, poly Lactic-co-Glycolic Acid (pLGA) particles of 200 nm, tocopheryl phosphate, lecithin, phospholipids, phospholipon 90G or phospholipon 90NG, volpo, cholesterol, span, tween, pluronic, DPPC, glyercol. Reagents in such preparations may include organic solvents, such as ethanol, isopropanol, ether and/or chloroform. Parenteral formulations may also contain adjuvants such as solubilizers, preservatives, wetting agents, emulsifiers, dispersants, and stabilizers, and aqueous suspensions may contain substances that increase the viscosity of the suspension, such as sodium carboxymethyl cellulose, sorbitol, and dextran. Injectable formulations are rendered sterile by incorporation of a sterilizing agent, filtration through a bacteria-retaining filter, irradiation, or heat. They can also be manufactured using a sterile injectable medium. The active agent may also be in dried (e.g. lyophilized), form that may be rehydrated with a suitable vehicle immediately prior to administration via injection.

In addition, DITPA may also be formulated for transdermal or implant administration. Such long acting implantation administrations include subcutaneous or intramuscular implantation. Thus, for example, DITPA may be formulated with suitable polymeric or hydrophobic materials (for example as an emulsion in an acceptable oil) or ion exchange resins or as sparing soluble derivatives, for example as a sparingly soluble salt.

A transdermal delivery system for use in accordance with the invention may include a carrier, such as a liquid, gel, solid matrix, or pressure sensitive adhesive or patch, into which DITPA is incorporated.

Although solutions of DITPA are generally preferred in embodiments that involve parenteral administration, emulsions are also effective. Such emulsions may be aqueous, in which the aqueous phase is the major and continuous phase, or non-aqueous, in which a water-insoluble solvent system comprises the continuous phase.

Although DITPA will generally be administered enterally or parenterally, other modes of administration are suitable as well for use in the invention. For example, administration may be rectal or vaginal, preferably using a suppository that contains, in addition to DITPA, excipients such as a suppository wax. Formulations for nasal or sublingual administration may also prepared with standard excipients well known in the art. DITPA may also be formulated for inhalation, e.g., as a solution in saline, as a dry powder, or as an aerosol.

Pharmaceutical compositions comprising DITPA (or other thyroid hormones or analogues) as the therapeutically active ingredient, may optionally further comprise one or more conventional ingredients. Examples of conventional ingredients include, but are not limited to, carriers, gelling agents, stabilizers, solvents, excipients, solubilisers, binders, buffers, preservatives, lubricants, suspending agents, disintegrating agents, flavours, sweeteners, antioxidants, isotonic agents, and combinations thereof. Other conventional ingredients may be discussed below.

Any conventional ingredient included in a pharmaceutical composition for use in the invention must be "pharmaceutically acceptable", meaning that it is compatible with the other ingredients of the composition and is not deleterious to DITPA (or the other thyroid hormone or analogue, as the case may be) or the patient. Accordingly, the present invention further provides a pharmaceutical composition comprising DITPA (or an alternative thyroid hormone or analogue, as the case may be) and one or more pharmaceutically acceptable conventional ingredients.

The conventional ingredients may be present from 0 up to about 50 weight percent of the total weight of the pharmaceutical composition, or in an amount up to 5 times the weight percent of the amount of DITPA (or an alternative thyroid hormone or analogue, as the case may be).

Examples of suitable stabilizers include albumin, globulin, gelatin, mannitol, glucose, dextran, ethylene glycol and the like. Examples of suitable solvents include water, lower alcohols ($C_2$-$C_6$) including ethanol, isopropyl alcohol, propyl alcohol, and so on. Other examples of solvents include glycols such as ethylene glycol, propylene glycol, glycerol, and the like. The solvent may also be one or more dialkylsulfoxides and/or dialkylsulfones. The solvent may also comprise one or more ketones, ethers, and esters such as for example acetone, methylethylketone, dimethylether, diethylether, dibutylether, and alkyl acetates, alkyl proprionates, alkyl butyrates, and the like.

The ingredients in a pharmaceutical composition for use in the invention, may include one or more pharmaceutically acceptable antioxidants. For this purpose, the term "antioxidant" refers to a molecule capable of slowing or preventing the oxidation of other molecules. Oxidation is a chemical reaction that transfers electrons from a substance to an oxidizing agent. Oxidation reactions can produce free radicals, which start chain reactions that damage cells. Antioxidants terminate these chain reactions by removing free radical intermediates, and inhibit other oxidation reactions by being oxidized themselves. As a result, antioxidants are often reducing agents.

Antioxidants are generally classified into two broad divisions, depending on whether they are soluble in water (hydrophilic) or in lipids (hydrophobic). Ascorbic acid (vitamin C) is an example of a water soluble antioxidant. Carotenes, tocopherol (Vitamin E), retinol (Vitamin A), ubiquinol (the reduced form of coenzyme Q) and calciferol (Vitamin D) are examples of lipid soluble antioxidants.

Carotenes are carotenoids containing no oxygen. Carotenoids are based on carotenes with one or more hydrogen atoms substituted by a hydroxyl group and/or some pairs of hydrogen atoms are substituted by oxygen atoms. The term "hydroxy carotenoids" refers to carotenes substituted with one or more hydroxyl groups. Cryptoxanthin is an example of a hydroxy carotenoid: it is closely related to beta-carotene with only the addition of a hydroxyl group.

Vitamin E exists in eight different forms, namely four tocopherols and four tocotrienols. All feature a chroman ring, with a hydroxyl group that can donate a hydrogen atom to reduce free radicals and a hydrophobic side chain which allows for penetration into biological membranes. Such derivatives of Vitamin E may be classified as "hydroxy chromans". Both tocopherols and tocotrienols occur in alpha, beta, gamma and delta forms, determined by the number and location of methyl groups on the chroman ring. The tocotrienols differ from the analogous tocopherols by the presence of three double bonds in the hydrophobic side chain.

Retinol belongs to the family of chemical compounds known as retinoids. There are three generations of retinoids. First generation retinoids include retinol, retinal, tretinoin (retinoic acid, Retin-A), isotretinoin and alitretinoin. Second generation retinoids include etretinate and its metabolite acitretin. Third generation retinoids include tazarotene, bexarotene and adapalene.

Ubiquinol is a benzoquinol and is the reduced form of ubiquinone (coenzyme $Q_{10}$). Calciferol (Vitamin D) comes in several forms. The two major forms are vitamin $D_2$ (e.g. ergocalciferol) and vitamin $D_3$ (e.g. calcitriol, cholecalciferol). The other forms include vitamin (molecular compound of ergocalciferol with lumisterol, 1:1), vitamin $D_4$ (22-dihydroergocalciferol) and vitamin D5 (sitocalciferol, made from 7-dehydrositosterol).

Any antioxidant or derivative thereof described herein would be suitable for the present invention. Preferred antioxidants and derivatives thereof are selected from the group consisting of carotenoids, hydroxy chromans, carotenoids, retinoids, benzoquinols and calcitriols. Hydroxy chromans are preferred. Tocols such as a tocopherol and its derivatives including salts (sodium), in any form, is most preferred.

One example of a gelling agent is sodium carboxymethyl cellulose.

One example of a sweetener is sodium saccharin.

Pharmaceutical compositions suitable for use in the invention may also comprise one or more agents known to accelerate the delivery of medicaments through the skin or mucosa (including intestinal mucosa) of animals, including humans, which are sometimes known as penetration enhancers, accelerants, adjuvants, and sorption promoters, and are collectively referred to in this specification as "enhancers". Some examples of enhancers include polyhydric alcohols such as dipropylene glycol; oils such as olive oil, squalene, and lanolin; polyethylene glycol ethers and fatty ethers such as cetyl ether and oleyl ether; fatty acid esters such as isopropyl myristate; fatty acid alcohols such as oleyl alcohol; urea and urea derivatives such as allantoin; polar solvents such as dimethyldecylphosphoxide, methyloctylsulf oxide, dimethylacetonide, dimethyllaurylamide, dodecylpyrrolidone, isosorbitol, decylmethylsulfoxide, and dimethylformamide; salicylic acid; benzyl nicotinate; bile salts; higher molecular weight aliphatic surfactants such as lauryl sulfate salts. Other agents include oleic acid and linoleic acids, ascorbic acid, panthenol, butylated hydroxytoluene, tocopherol, tocopheryl acetate, tocopheryl linoleate, propyloleate, tocopheryl phosphate, sodium tocopheryl phosphate, di-sodium tocopheryl phosphate, Trolox™ (6-hydroxy-2,5,7,8-tetramethylchroman-2-carboxylic acid, a water-soluble derivative of vitamin E), isopropyl palmitate, oleamide, polyoxyethylene lauryl ether, polyoxyethylene olelyl ether and polyoxyethylene oleyl ether. The one or more enhancers may be present from 0 up to about 10 weight percent of the total weight of the pharmaceutical composition, or in an amount up to 5 times the weight percent of the amount of DITPA (or an alternative thyroid hormone or analogue, as the case may be).

Pharmaceutical compositions may be formulated according to techniques such as those well known in the art of pharmaceutical formulation. (See, for example, Remington: *The Science and Practice of Pharmacy,* 21 st Ed., 2005, Lippincott Williams & Wilkins).

A simple method for preparing a pharmaceutical composition comprising DITPA and one or more conventional ingredients involves mixing the DITPA with the one or more optional ingredients to form the pharmaceutical composition. Preferably, DITPA is provided in powdered form, having >98.0% purity.

When preparing a pharmaceutical composition also comprising one or more antiinflammatory agents, the one or more anti-inflammatory agents may be mixed with the one or more conventional ingredients at the same time as the DITPA.

In one embodiment, a pharmaceutical composition comprises DITPA and a vehicle solution, preferably aqueous and/or able to form a suspension. One example of an aqueous vehicle comprises water, one or more enhancers, a gelling agent, and a sweetener. The one or more enhancers may be tocopheryl phosphate, sodium tocopheryl phosphate, di-sodium tocopheryl phosphate, the gelling agent may be sodium carboxymethyl cellulose, and the sweetener may be sodium saccharin. The sodium tocopheryl phosphate may be present in an amount of 0.25% w/v, sodium carboxymethyl cellulose may be present in an amount of 0.5% w/v, and the sodium saccharin may be present in an amount of 0.02%, with water making the balance to about 12 ml. To prepare such a pharmaceutical composition, 30 mg powdered DITPA is mixed in 12 ml aqueous vehicle. When DITPA is mixed with a vehicle solution, as described, the mixture will form a suspension of 2.5 mg DITPA/ml. The volume of the mixture that is to be administered to achieve the patient's dose may be calculated according to body weight of the patient. The following is an example on how to calculate the volume: For a patient's body weight of 25 kg and the dose of 1.5 mg/kg then the amount of DITPA to be administered is 37.5 mg per day. Dividing the dose into 3 portions means that 0.5 mg/kg will be given 3 times a day. Each of the 3 daily portions is prepared as follows: 25 kg×0.5 mg/kg=12.5 mg DITPA. The amount of mixture at 2.5 mg/ml needed for 12.5 mg is 12.5/2.5 mg/ml, and therefore the volume of the mixture is 5 ml. The unused portion is discarded. Surplus mixture of DITPA in vehicle is discarded.

Any pharmaceutical composition comprising DITPA is preferably prepared immediately before use (or within at least 30 minutes), particularly if a solution or suspension. However, DITPA may be pre-formulated as a ready to use pharmaceutical preparation that has been demonstrated to have stability and a good shelf-life.

Unless the context requires otherwise, wherever used in this specification, the expression "therapeutically effective amount" refers to an amount of DITPA (or an alternative thyroid hormone or analogue) that will elicit the biological or medical response of a patient, tissue or cell that is being investigated or treated (as the case may be) by a researcher, veterinarian, medical doctor or other clinician. This amount may be within the range of from about 0.1 to about 5 mg/kg body weight/day, from about 0.5 to about 5 mg/kg body weight/day, from about 0.5 to about 3 mg/kg body weight/day, or from about 1 to about 2 mg/kg body weight/day. Preferably, the amount of DITPA is within the range of from about 1 to about 5 mg/kg body weight/day. In some embodiments, the amount of DITPA is about 0.5 mg/kg body weight/day, about 1 mg/kg body weight/day, about 1.5 mg/kg body weight/day, about 2 mg/kg body weight/day, about 2.7 mg/kg body weight/day, about 3 mg/kg body weight/day, about 3.6 mg/kg body weight/day, about 4 mg/kg body weight/day, about 4.5 mg/kg body weight/day, about 4.75 mg/kg body weight/day, or about 5 mg/kg body weight/day. In one embodiment, the daily dose of DITPA is divided into 3 equal portions given 3 times a day, at intervals of about 8 hours.

The methods of the invention also embrace the possibility of DITPA (or an alternative thyroid hormone or analogue) being co-administered to a patient in combination with other pharmaceutical agents, formulations or composition, as appropriate to treat the patient. So, for example, a patient could be treated using a combination of DITPA and an anti-inflammatory agent.

In a seventh aspect, the present invention generally provides a method of treating or ameliorating a neurological disorder associated with slc16A2 gene deficiency or impairment in a patient in need of such treatment or amelioration, the method comprising the step of administering to the patient, an effective amount of a thyroid hormone or thyroid hormone analogue.

In this seventh aspect of the invention,
(a) the patient may be any of the kinds of subjects previously discussed.
(b) the neurological disorder may be any of the neurodegenerative disorders previously discussed; and
(c) the thyroid hormone or thyroid hormone analogue is any of the substances, compositions or formulations previously discussed, but where DITPA is the preferred agent for treating the patient.

Further, in this seventh aspect of the present invention, the neurological disorder associated with slc16A2 gene deficiency or impairment may be one:

(a) that arises in the patient via genetic or hereditary means; or
(b) arises in the patient after conception or birth other than via genetic or hereditary means.

In an eighth aspect, the present invention generally provides a method of treating or ameliorating a neurological disorder associated with slc16A2 gene deficiency or impairment in a patient in need of such treatment or amelioration, the method comprising the step of administering to the patient, an effective amount of a genetic repair means.

In this eighth aspect of the invention,
(a) the patient may be any of the kinds of subjects previously discussed.
(b) the neurological disorder may be any of the neurodegenerative disorders previously discussed; and
(c) the genetic repair means is preferably a clustered regulatory interspaced short palindromic repeat (CRISPR)/Cas-based RNA-guided DNA endonuclease to repair the patient's genome.

Preferably, in this embodiment of the invention, the genetic repair means administered to the patient through recombinant vectors such as adenoassociated viral (AAV) or lentiviral (LV) vectors.

In a ninth aspect of the present invention, the invention generally provides a method of treating or ameliorating a neurological disorder associated with slc16A2 gene or MCT8 deficiency or impairment in a patient in need of such treatment or amelioration, the method comprising the step of administering to the patient, an effective amount of vertebrate oligodendrocyte precursor cells produced via the methods of the third aspect of the invention.

In this ninth aspect of the invention,
(a) the patient may be any of the kinds of subjects previously discussed. and
(b) the neurological disorder may be any of the neurodegenerative disorders previously discussed.

Preferably, in this aspect, the vertebrate oligodendrocyte precursor cells would be administered to the patient in the course of or via a surgical procedure. Preferably, in the surgical procedure, the vertebrate oligodendrocyte precursor cells would be administered to the patient:
(a) via infusion of a single intrathecal bolus;
(b) comprising about $1 \times 10^6$ purified MCT8-expressing OPCs;
(c) in a suitable physiological medium; and
(d) either with our without a thyroid hormone or analogue, such as DITPA.

BRIEF DESCRIPTION OF THE DRAWINGS

Preferred embodiments of the Invention will now be described by way of example only, with reference to the accompanying drawings, in which:

| Drawing Number | Description |
| --- | --- |
| FIG. 1 | Depicts schematically, an exemplary method of deriving oligodendroglial precursor cells from a Hes3-derived Nkk2.1-GFP cell line, in accordance with the invention |
| FIG. 2 | Depicts the isolation of high GFP (Nkx2.1) expressing embryonic stem cells following the provision of shh at stage III of the illustrated exemplary method according to the invention. Subsequent to the isolation and growth of these high GFP (Nkx2.1) expressing cells, the enhancement of oligodendroglial precursoor cell yield was observed by the end of stage VI under the conditions outlined in FIG 1. |
| FIG. 3 | Illustrates the expression of the monocarboxylate transporter 8 on enriched oligodendroglial cells at Stage VI derived from the previously isolated Nkx2.1- |

Figure 17:
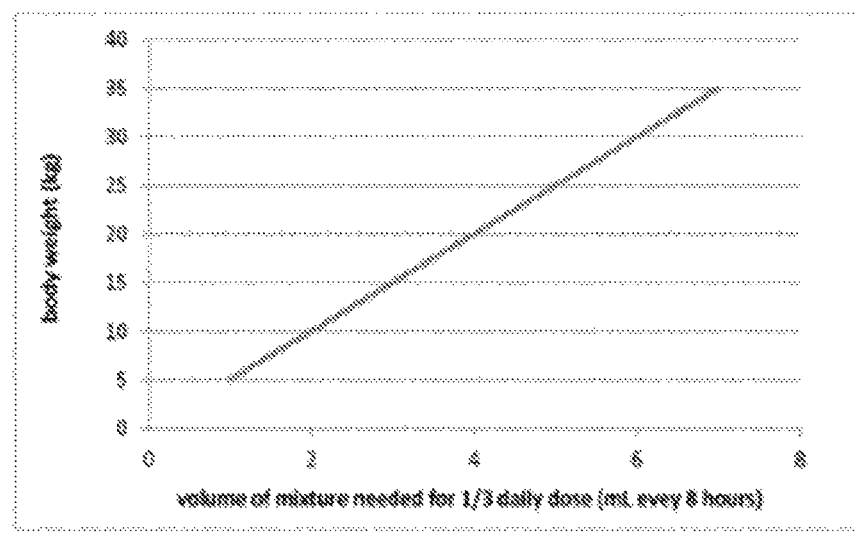
Figure 18:
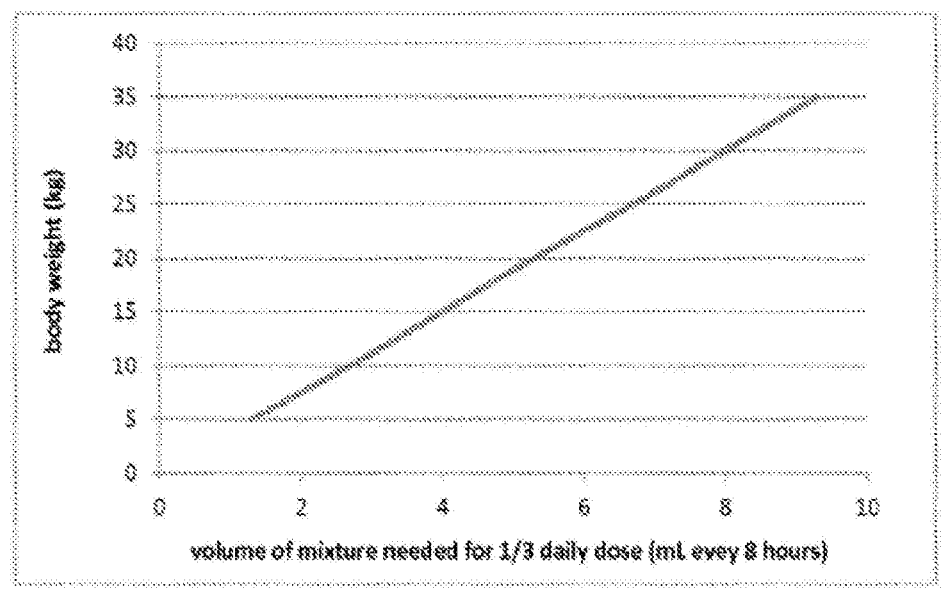
Figure 19:
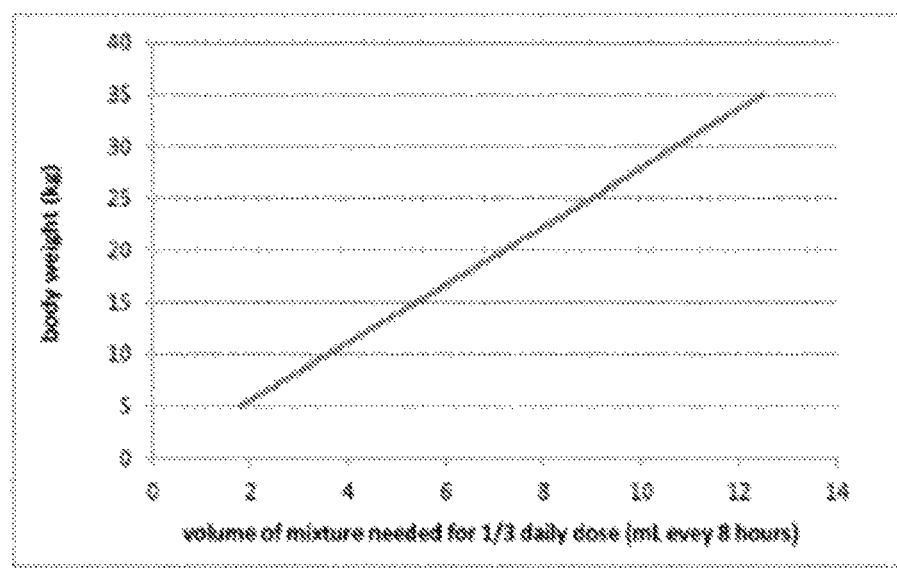
Figure 20:
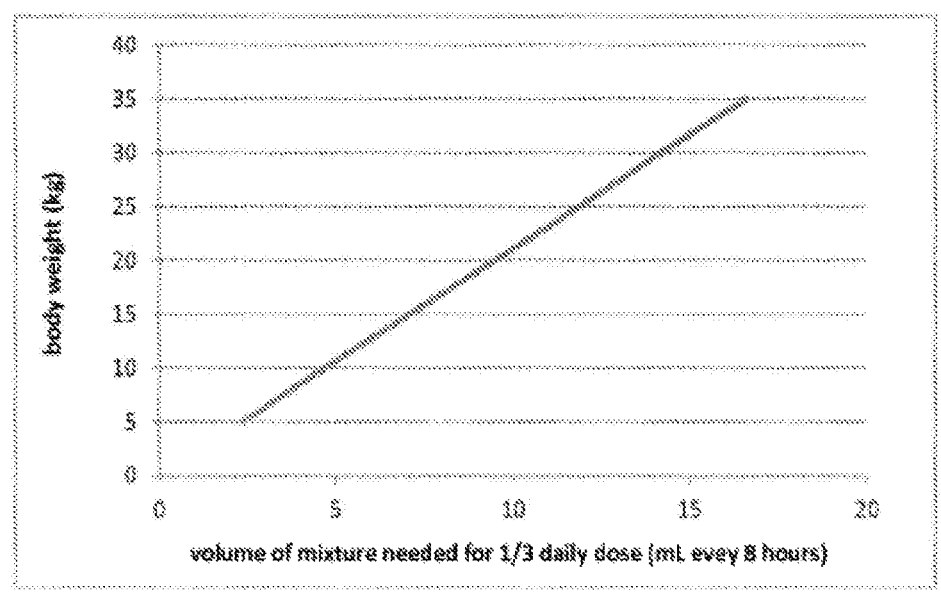
Figure 21:
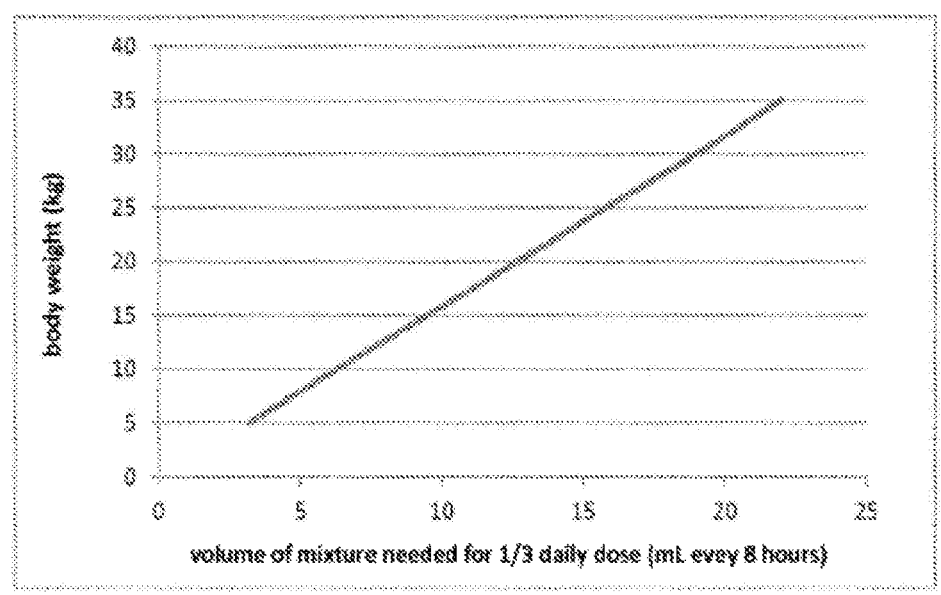

| Drawing Number | Description |
| --- | --- |
| | GFP hESCs. As depicted, all mature markers of OPCs and mature oligodendrocytes demonstrate MCT8 expression. |
| FIG. 4 | Represents the biological outcome of providing DITPA for 48 hours in culture to oligodendroglial precursor cells derived from the H9 hESC line. As shown, DITPA administration upregulated known OPC-specific transcription factors at concentrations of 1 and 10 ng/mL. |
| FIG. 5 | Depicts the results of an experiment which show that DITPA promotes cell cycle exit of OPCs, enhancing their differentiation. |
| FIG. 6 | Depicts an experiment which shows that DITPA promotes the myelination of rat retinal ganglion cells. |
| FIG. 7 | Depicts an experiment which shows that DITPA rescues oligodendrocyte death mediated by MCT8 deficiency and can still promote myelination of axons under such deprivation conditions. |
| FIG. 8 | Shows the differential expression of the nkx2.1 transcription factor during neural precursor derivation from hESCs. |
| FIG. 9 | Shows enhanced yield of early derived OPCs isolated from the nkx2.1 GFP + hESC line of cells. |
| FIG. 10 | Shows low yields of neuroepithelial cells isolated from the nkx2.1 GFP + hESC line of cells. |
| FIG. 11 | Shows MCT10, DIO2, and DIO3 are all expressed in oligodendroglial lineage cells (related to FIG. 3) |
| FIG. 12 | Shows that DITPA regulates cell cycle associated signaling pathways and associated genes to promote OL development (related to FIG. 4 and 5) |
| FIG. 13 | DITPA treatment of differentiating OPCs overcomes the cell death initiated by the pharmacological blockade of MCT8 through Bosutinib. |
| FIG. 14 | Shows downregulation of slc16A2 using the lentivirus carrying the shRNA of the slc16A2 gene. |
| FIG. 15 | Depicts MCT8 expression in the mouse sub ventricular zone, corpus callosum and optic nerve. |
| FIG. 16 | Shows dysregulation of thyroid hormone signaling during progression of EAE disease and in post mortem brain tissue from Multiple Sclerosis patients. |
| FIG. 17 | Is a chart showing body weight and volume of mixture required for the dose of 0.5 mg/kg. This is ⅓ of the daily dose; therefore, it is repeated 3 times a day. |
| FIG. 18 | Is a chart showing body weight and volume of mixture required for the dose of 0.67 mg/kg. This is ⅓ of the daily dose; therefore, repeat this 3 times a day. |
| FIG. 19 | Is a chart showing body weight and volume of mixture required for the dose of 0.89 mg/kg. This is ⅓ of the daily dose; therefore, repeat this 3 times a day. |
| FIG. 20 | Is a chart showing body weight and volume of mixture required for the dose of 1.19 mg/kg. This is ⅓ of the daily dose; therefore, repeat this 3 times a day. |
| FIG. 21 | Is a chart showing body weight and volume of mixture required for the dose of 1.583 mg/kg. This is ⅓ of the daily dose; therefore, repeat this 3 times a day. |

DETAILED DESCRIPTION OF PREFERRED EMBODIMENTS OF THE INVENTION

Example 1—Overcoming MCT8 Deficiency in Oligodendrocytes

Introduction

Thyroid hormones (THs) play a vital role during mammalian embryonic brain development. The monocarboxylate transporters are now known to facilitate the transport of TH into cells to exert both genomic and non-genomic effects upon cellular development and metabolism (for review see Visser et al., 2008). The monocarboxylate transporter 8 (MCT8) has recently been identified as the candidate TH transporter, since the only substrates have been shown to be tri-iodothyronine ($T_3$) and its pro-hormone thyroxine ($T_4$) (Friesema et al., 2003; Kinne et al., 2010). In humans, mutations at the slc16a2 gene locus (encoding MCT8) cause the severe congenital X-linked psychomotor retardation, known as Allan-Herndon-Dudley syndrome (AHDS) (Dumitrescu et al., 2004; Friesema et al., 2004). Along with the increased serum levels of free-$T_3$, developmentally delayed myelination shown by magnetic resonance imaging (MRI), is a common feature of this disorder (Armour et al., 2015; Gika et al., 2010; Vaurs-Barriere et al., 2009). Although myelination was reported in T2-weighted MRI from follow-up longitudinal studies of AHDS patients, the developmental is incomplete as neurological phenotypes persist (Armour et al., 2015; Gika et al., 2010; Vaurs-Barriere et al., 2009). Furthermore, a recent post-mortem analysis of an 11-year-old AHDS boy revealed prominent hypomyelination by myelin basic protein (MBP) immunostaining (Lopez-Espindola et al., 2014).

Despite dependency for THs during oligodendrocyte (OL) differentiation, cell entry of these hydrophobic hormones remains undefined. Since slc16a2 mutant mice display no observable neurological phenotype (Dumitrescu et al., 2006; Wirth et al., 2009), we utilized oligodendroglial precursor cells (OPCs) derived from human embryonic stem cells (hESCs) to identify the expression profiles and physiological role of MCT8 during OL development. Several protocols exist that derive OPCs from hESCs (for review see Alsanie et al., 2013), although the efficiency to develop homogeneous cultures varies which limit clear molecular analyses of OPCs and mature OLs. Therefore, we developed a modified technique to obtain high yields of oligodendroglial cells to clearly define the role of MCT8 during OL development.

TH analogs that do not require MCT8 have been suggested as a potential therapy to treat AHDS. For example, di-iodothyropropionic acid (DITPA) can normalize peripheral hyperthyroidism and reduce hypermetabolism in AHDS patients (Verge et al., 2012). However, the exact mechanism by which DITPA acts is largely unknown. Considering our findings of reduced OL viability upon inhibition of MCT8, in this study we posit that the provision of DITPA upon knockdown of slc16a2 in hESC-derived OPCs may potentiate their proliferation and differentiation. Microarray analysis revealed up-regulation of OL-specific transcription factors upon DITPA administration to early OPCs. We tested the effect of DITPA upon OL development and found that it induced cell cycle exit, OPC differentiation and myelination in vitro. Importantly, DITPA administration rescued these cells from apoptosis mediated by slc16a2 down-regulation and promoted their myelination of axons. Collectively, these data suggest that MCT8 is a physiological TH transporter in OLs and that early intervention using DITPA holds therapeutic promise in enhancing myelination in AHDS.

Results

Nkx2.1-GFP-Based Sorting Enhances OPC Yield

The inventors utilized two hESC lines in this study; Hes3 and Hes3-derived Nkx2.1-GFP reporter line (Goulburn et al., 2011). The protocol of (Chaerkady et al., 2011) was modified with the addition of sonic hedgehog (shh) (Pringle et al., 1996) during the neural precursor stage of differentiation (FIG. 1). The inventors successfully derived PDGFRα+/NG2+ OPCs, O4+ pre-OLs and MBP+ premyelinating OLs (FIG. 1). By flow cytometry and immunocytochemistry, the inventors identified that the peak of PDGFRα+/NG2+ OPCs and O4+ pre-OLs was at the end of stage IV and VI, respectively. However, the yields of PDGFRα+/NG2+ OPCs and O4+ pre-OLs by the end of stage VI were low.

To increase the yield of OLs, the inventors sorted Nkx2.1+ cells at peak GFP expression during differentiation. By live imaging and flow cytometry, the inventors observed Nkx2.1-GFP induction at day 8 of stage II (FIG. 8). During stage III, the inventors identified that the maximal induction of Nkx2.1-GFP occurred by day 5, served as a time-point for cell sorting (FIGS. 2A-B). Therefore, both GFP+ and GFP− cells were sorted by FACS at day 5 of stage III, then differentiated under the same culture conditions upon which their oligodendrogenic potential was addressed. qRT-PCR for nkx2.1 showed significant up-regulation of this gene in GFP+ compared with GFP− sorted populations at stages IV-V (FIG. 2C). First, the yield of PDGFRα+/NG2+ OPC derivation was analyzed. At the end of stage IV, the yield of OPC derivation was significantly higher in the GFP+ (~55.2%) compared with GFP− (~1.62%) isolated cells (FIGS. 2D-E). This trend was also evident at stage V day 6, although the percentage of PDGFRα+/NG2+ OPCs significantly decreased as the cells differentiated (FIG. 2F, FIGS. 9A-B). Immunocytochemistry for PDGFRα and NG2 at stage IV day 12, supported the flow cytometry data (FIGS. 2G-H). Furthermore, in line with these data the inventors also showed significant up-regulation in pdgfra from stage IV day 12, to stage V day 8, whereas the cspg4 (encoding NG2) gene was significantly up-regulated early from stage IV onwards in GFP+ compared with GFP− sorted cells (FIGS. 2I-J). Next, the inventors analyzed the yield of O4+ pre-OL derivation from stage IV to stage VI. It was found that the percentage of O4+ pre-OLs was significantly higher in GFP+ compared with GFP− sorted cells from stages V-VI (FIGS. 2K-O). Immunocytochemistry analysis also demonstrated a greater derivation of O4+ pre-OLs at the end of stage VI (FIGS. 2N-O). In support of these data, qRT-PCR analysis for the mbp gene showed a ~4-fold up-regulation in GFP+ sorted cells when compared with GFP− isolated cells at stage VI day 21 (FIG. 2P). Further to these surface markers, the inventors analyzed an essential transcription factor for oligodendrogenesis, Sox10 (FIGS. 9C-F). From immunocytochemistry analysis, the inventors demonstrated that there was a significant number of cells that expressed Sox10 derived from the GFP+ sorted cells at stage IV day 12 (~49.22%), to stage VI day 21 (~82.44%), compared to the GFP− sorted cells (FIG. 9E). qRT-PCR analysis supported these immunocytochemistry data, showing significantly up-regulated sox10 gene expression levels in GFP+ when compared with the GFP− sorted cells from stage IV day 12, to stage V day 8 (FIG. 9F). Analysis of other neural lineages by flow cytometry, immunocytochemistry and qRT-PCR demonstrated that significantly lower numbers of cells were Nestin+ neural precursors, GFAP+ astrocytes, and β-III-tubulin+ neurons derived from GFP+ compared to GFP− sorted cells at stage VI day 21 (FIGS. 10D-U). Furthermore, there were low yields of neuroepithelial cells derived throughout the differentiation of both GFP+ and GFP− isolated cells (FIGS. 10A-C). Collectively, these data suggest that sorting of the Nkx2.1-GFP+ cell enhanced the yield of OL derivation.

MCT8 is Expressed on Oligodendroglial Lineage Cells

Figure 3:
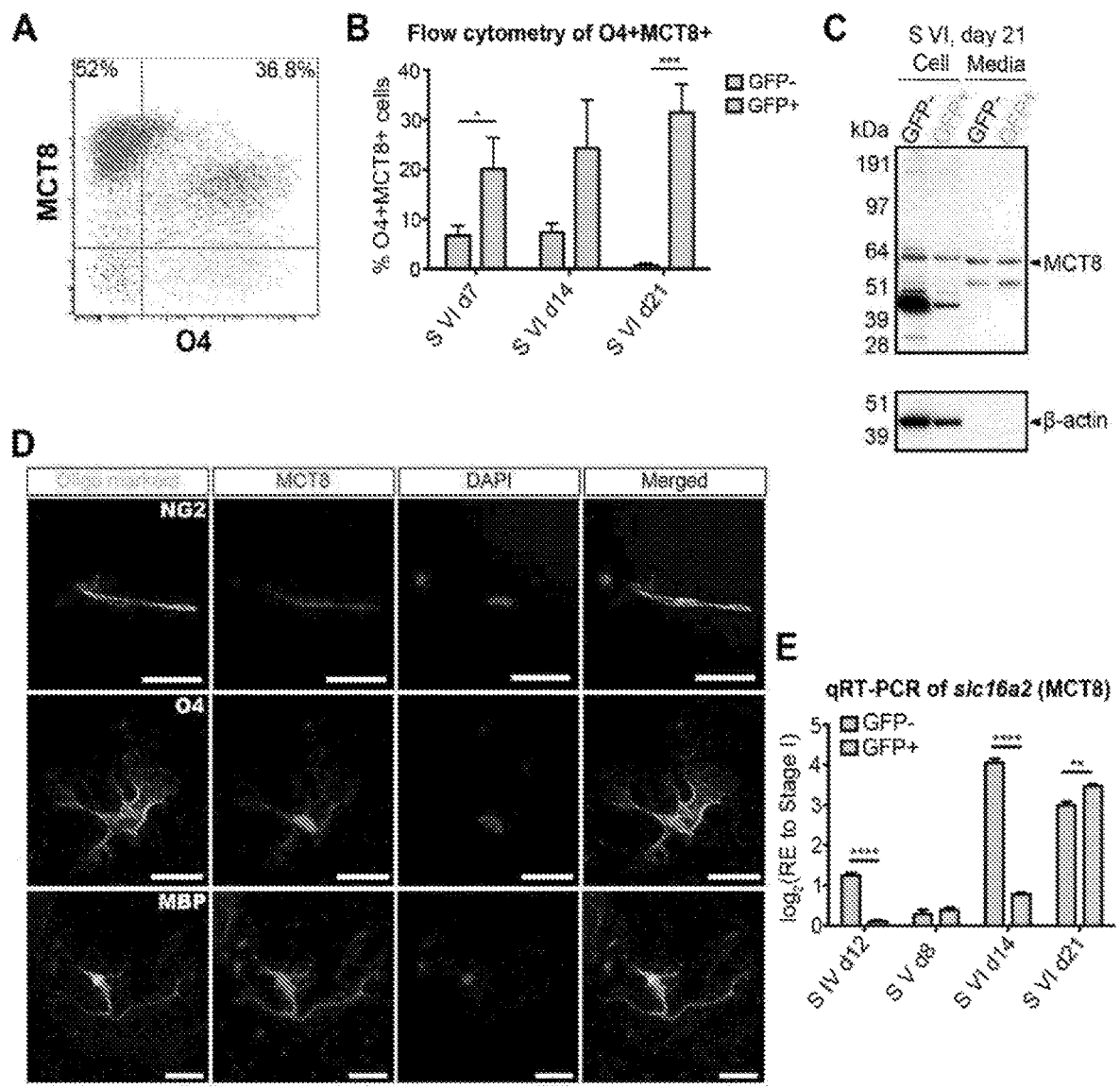

Since consistent and validated high yields of OLs from Nkx2.1-GFP+ sorted cells were established, we went on to identify that MCT8 was indeed co-expressed with various oligodendroglial lineage markers (FIG. 3). Firstly, we showed MCT8 expression on O4+ pre-OLs by flow cytometry during stage VI, where significant numbers of O4+ cells were labeled with MCT8 among the GFP+ sorted cultures (FIGS. 3A-B). Moreover, western blot analysis of cell lysates from stage VI, revealed a specific monomeric form of MCT8 (~60 kDa) (Friesema et al., 2006) in both the GFP− and GFP+ isolated cells. The inventors also detected this in the conditioned medium, indicating MCT8 may be secreted extracellularly (FIG. 3C). Immunocytochemical analysis revealed co-localization of MCT8 in Olig2+ oligodendroglia, O4+ pre-OLs, CNPase+ and MBP+ pre-myelinating OLs at the end of stage VI. Moreover, MCT8 immunostaining at stage IV day 12, also showed co-localization of MCT8 in NG2+ OPCs, indicating that MCT8 is expressed in immature precursors through to pre-myelinating OLs (FIG. 3D). qRT-PCR analysis for slc16a2 revealed increasing levels of this gene from the OPC stage (stage IV day 12) through to the pre-OL stage (stage VI day 21) in GFP+ isolated cells (FIG. 3E). These results indicate that MCT8 is expressed in maturing oligodendroglial lineage cells. Along with MCT8 we identified the expression of MCT10 (the alternate TH transporter, (Friesema et al., 2008)) in PDGFRα+ OPCs and O4+ pre-OLs derived from Nkx2.1-GFP+ sorted cells (FIGS. 11A-H). Additionally, we found the expression of DIO2 and DIO3 in these O4+ cells (FIGS. 11I-P), demonstrating that these MCT8/10-expressing oligodendroglial lineage cells actively uptake THs and metabolize them.

DITPA Potentiates OL Development in Mixed Neural Cultures

To identify whether DITPA can promote oligodendrogenesis in the same manner as $T_3$, we first utilized the human OPC differentiation kit (Merck-Millipore). Using this kit, the inventors were able to derive ~30% of NG2+ OPCs at the end of differentiation (Week 4) (FIG. 4A). Further analysis revealed that there was a mixed population of Nestin+ neural precursors, GFAP+ astrocytes and β-III-tubulin+ neurons at the end of differentiation (Week 4, data not shown), indicating these cells are at the early stage of OPC specification from multipotent neural precursors. From this time-point, cells were treated with 1 ng/mL and 10 ng/mL of DITPA for 48 hours and microarray analysis performed. Cells grown in differentiation medium with 0.01% ethanol (dissolvent of DITPA) served as a negative control. Gene expression profiles of cells treated with DITPA at 1 ng/mL and DITPA at 10 ng/mL vs Ethanol control; showed 3385 of commonly regulated genes following the provision of different DITPA concentrations (FIG. 4C), illustrated in the heatmap (FIG. 4D). Gene ontology (GO) analysis showed that development-related genes were regulated upon DITPA treatment (FIG. 4E). From this GO analysis, the inventors selected the GO term 'TH signaling' and found a down-regulation of retinoic acid response element 3 (RARRES3) and intracellular transporter of TH, μ-crystallin (CRYM) and up-regulation of deiodinase 3 (DIO3), nuclear retinoic acid receptor alpha (RARA), nuclear TH receptor β (THRB) and DIO3 opposite strand (DIO3OS) (FIG. 4F). These results indicate that DITPA may not be transported by μ-crystallin in the cell, however one plausible hypothesis is that DITPA may bind to the retinoic acid receptor α and TH receptor β to transcribe OL-related genes (Baas et al., 2002; Baas et al., 2000; Laeng et al., 1994). Importantly, the inventors found up-regulation of an array of transcription factors (lists from (Najm et al., 2013)) enriched in oligodendroglial cells such as achaete-scute homolog 1 (ASCL1) and myelin transcription factor 1 (MYT1) with DITPA treatment whereas, minimal astrocyte and neuron enriched transcription factors were regulated upon DITPA treatment (FIG. 4G). Since $T_3$ has been previously shown to promote cell cycle exit and OL differentiation (Barres et al., 1994), the inventors further analyzed cell cycle associated gene pathways such as BMP, TGF6, WNT, and Notch signaling (within the GO term). From this analysis, the inventors found genes associated with these pathways to be regulated by DITPA (FIGS. 12A-B). Furthermore, they found: (i) a significant up-regulation of the reprimo (RPRM) (~13 fold), a p53-dependent G2 arrest mediator (Laeng et al., 1994); (ii) up-regulation of metallothionein (MT1A) (~8 fold), a binding partner of p53 to modulate p53-dependent apoptosis (Ostrakhovitch et al., 2006); and (iii) the up-regulation of p53 (~2 fold) upon DITPA treatment (FIG. 12B). These results may indicate that DITPA promotes cell cycle exit and potentiates OL development at the early stage of differentiation.

DITPA Promotes Cell Cycle Exit to Potentiate OL Differentiation

Since a significant effect of DITPA was found in potentiating cell cycle exit and oligodendrogenesis at the early stage of differentiation, the inventors utilized the Nkx2.1-GFP+ sorted, enriched immature OL cultures to specifically test the effect of DITPA. For this analysis, the inventors treated cells (daily medium replacement for 21 days) with $T_3$ alone ($T_3$ control), DITPA alone (DITPA), or co-administration of $T_3$ and DITPA ($T_3$+DITPA) from Nkx2.1-GFP+ sorted cells at stage VI of terminal differentiation toward OLs, and analyzed them for gene expression (qRT-PCR) and by flow cytometry upon BrdU incorporation, specifically testing the cell cycle events occurring at day 7 and 21 post-treatment. Co-administration of $T_3$ and DITPA to test any functional relevance of the combined exogenous treatment was also included (FIG. 5A). At day 7, the inventors found a significant reduction in the numbers of cells that were in S phase upon both the administration of DITPA in the cultures, compared with those treated with $T_3$ alone. However, at day 21 the inventors found no significant differences among all three groups (FIGS. 5B-D). These data indicate that DITPA potentiates cell cycle exit faster than $T_3$. TH-responsive cell cycle arrest associated genes such as cdkn1b (encodes for p27) (FIG. 5E) and tp53 (encodes for p53) (FIG. 5F) were both up-regulated by DITPA and $T_3$+DITPA when compared to the $T_3$ treated cultures. As overexpression of p53 has been identified to potentiate apoptosis via death receptors (DRs) (Wosik et al., 2003), the inventors analyzed one of the DRs, which has been reported to promote oligodendrocytopathy, DR6 (Mi et al., 2011), and found almost negligible up-regulation of tnfrsf2 (encodes DR6) upon DITPA treatment. Hence, the up-regulation of tp53 by DITPA treatment is likely to promote cell cycle exit for the purpose of OL differentiation, not cell death (FIG. 5G). Along with these data, further gene expression analysis by qRT-PCR revealed that down-regulation of the essential genes for BMP signaling, bmp7, JNK signaling jun, TGF6 signaling, tgfb3, and WNT signaling wnt5a upon DITPA treatment occurs, corroborating the hypothesis that DITPA can promote differentiation. Furthermore, up-regulation of the WNT antagonists such as frzb, sfrp1, and sfrp2 were found upon DITPA treatment supporting this notion (FIG. 12C). These data indicate that DITPA potentiates oligodendroglial cell cycle exit, promoting differentiation at the late stage from OPCs toward O4+ pre-OLs.

Moreover, myelin genes such as myt1, plp1, and mbp all showed up-regulation following the treatment of differentiating cultures with DITPA (FIGS. 5H, I). In particular, at day 21 of DITPA treatment, the inventors found substantial up-regulation of plp1 than that documented for the cells treated with $T_3$ alone (FIGS. 5J-L). In line with these data, further qRT-PCR-based gene expression analysis revealed that master regulators of OL differentiation such as olig1, olig2 and sox10 were up-regulated following DITPA treatment. The most up-regulation of genes that occurred following DITPA treatment at day 7, were observed for olig1 and olig2, far greater than that seen for $T_3$. Moreover, important genes for OL development such as ascl1, pdgfra, and nkx6.2 were up-regulated following all treatment regimes. On the other hand, as cells mature, the immature OPC gene, cspg4 was down-regulated in all three treatment groups (FIG. 12C). These results suggest that DITPA promotes OL differentiation and this is far greater than what $T_3$ can facilitate.

Having established the OL derivation potential of DITPA, the inventors then asked whether there is dysregulation in TH signaling related genes. Firstly, the inventors found a significant up-regulation of slc16a2 and slc16a10 upon DITPA treatment at day 7 when compared with $T_3$. The results showed a ~14-fold up-regulation of slc16a10 following DITPA treatment (FIGS. 5M and N). Further analysis revealed no significant differences in the gene expression for thrb, dio2 and dio3, between T3 and DITPA treatments, indicating that similar intracellular signaling is operative upon either $T_3$ or DITPA stimulation of cells. Co-administration of $T_3$ and DITPA showed significant up-regulation of thrb and dio3 (FIG. 12C), which may indicate that cells are in a hyperthyroid state.

DITPA Promotes Myelination in Co-Culture

Since the evidence argued that DITPA can promote OL differentiation, the inventors next asked whether it also potentiates CNS myelination. For this, they set up a co-culture system comprising rat retinal ganglion cells (RGCs) and Nkx2.1-GFP+ sorted OPCs where, these cultures were treated with $T_3$, DITPA, or $T_3$+DITPA. Seven days following co-culture, the inventors were able to detect subsets of MBP+ OLs that began initiating or wrapping axons with myelin membrane in all treatment groups, identified by MBP+ segments around NF-200+ axons. Quantification revealed that more contacting or ensheathing MBP+ OLs are observed in DITPA treated cultures than those observed following treatment with $T_3$ alone. In line with this, the percentage of myelination (number of myelinated axons/total number of axons) was significantly enhanced with DITPA compared with $T_3$ treatment alone. These data illustrate that DITPA drives myelination of axons from differentiating OLs in an expedited manner than that occurs with $T_3$ under normal differentiation conditions and MCT8 expression status.

DITPA Attenuates OPC Death Induced by Bosutinib-Dependent MCT8-Blockade

Figure 13:
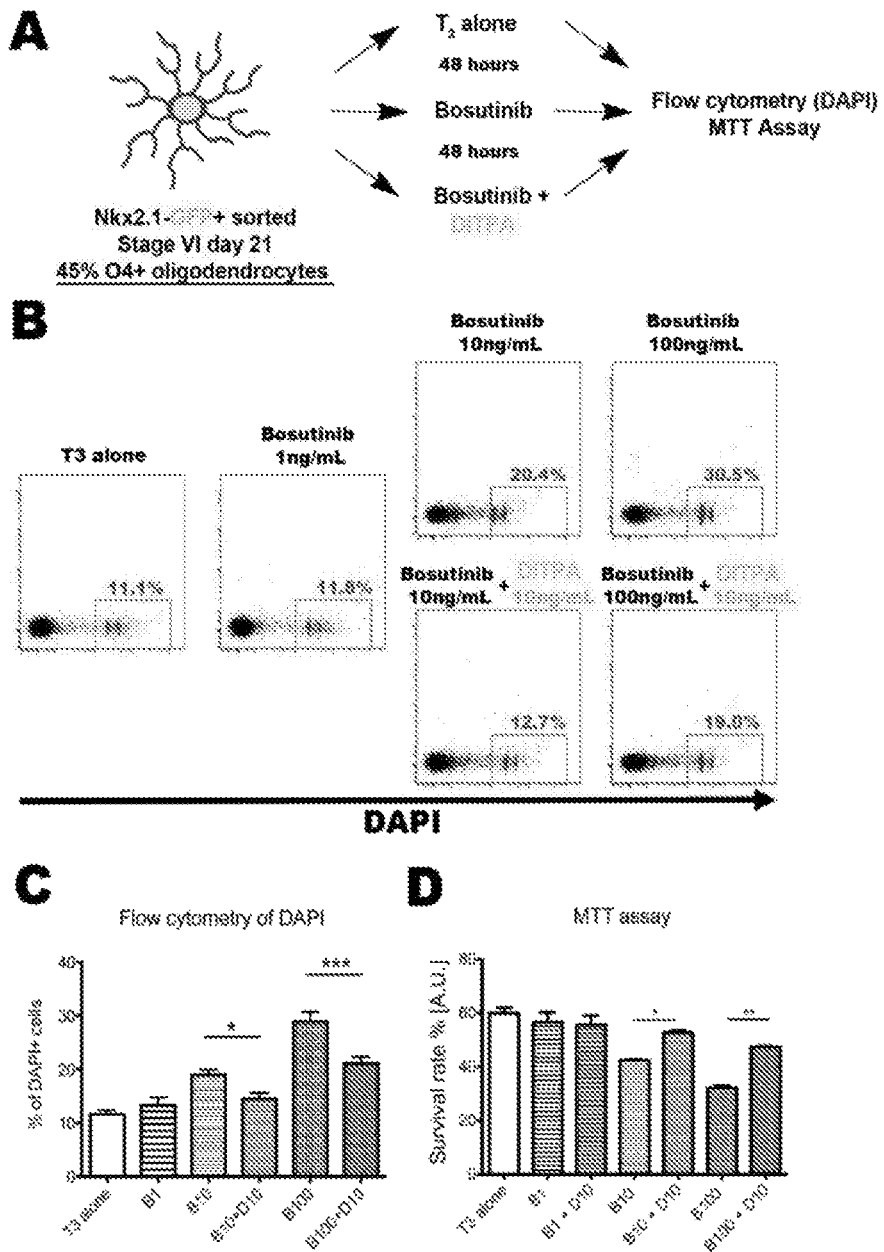

As DITPA is suggested to cross the plasma membrane in a MCT8-independent manner, the inventors then asked whether DITPA can bypass a specific MCT8 blockade to potentiate OL differentiation. A third generation of tyrosine kinase inhibitor, Bosutinib, was used to inhibit MCT8-mediated TH transport commonly used clinically for chronic myeloid leukaemia (Braun et al., 2012). We administered different concentrations of Bosutinib (1-100 ng/mL) with and without 10 ng/mL of DITPA for 48 hours to OL-enriched populations derived from Nkx2.1-GFP+ sorted cells at day 21 stage VI (FIG. 13). Flow cytometric analysis using DAPI revealed increased proportions of DAPI+ dead cells with increasing concentration of Bosutinib in culture, indicating MCT8 is required for the viability of these cells. However, upon co-administration of DITPA with Bosutinib, the inventors found a significant reduction in cell death (FIGS. 13B-C). A MTT-based cytotoxicity assay also supported this result (FIG. 13D).

Figure 7:
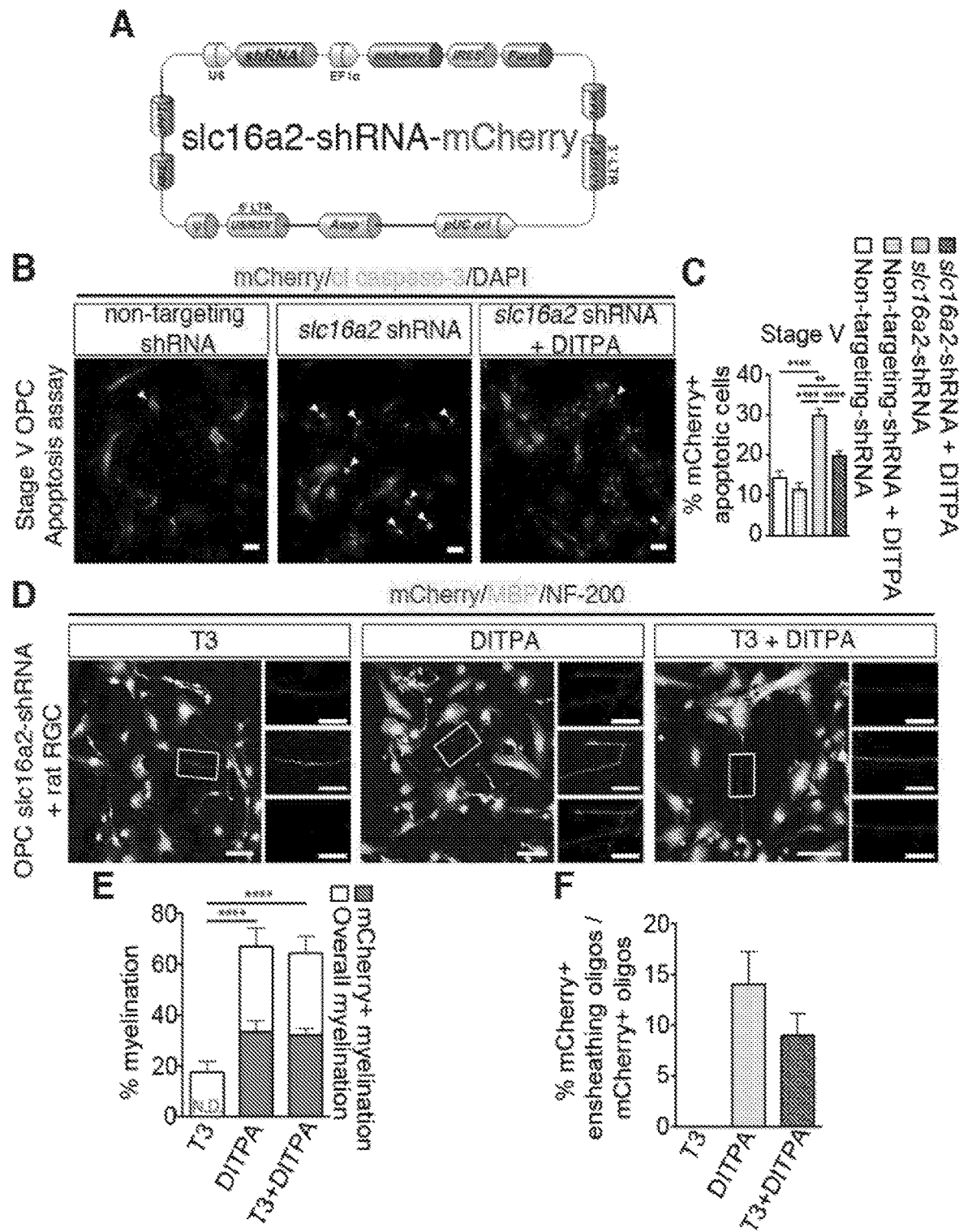
Figure 14:
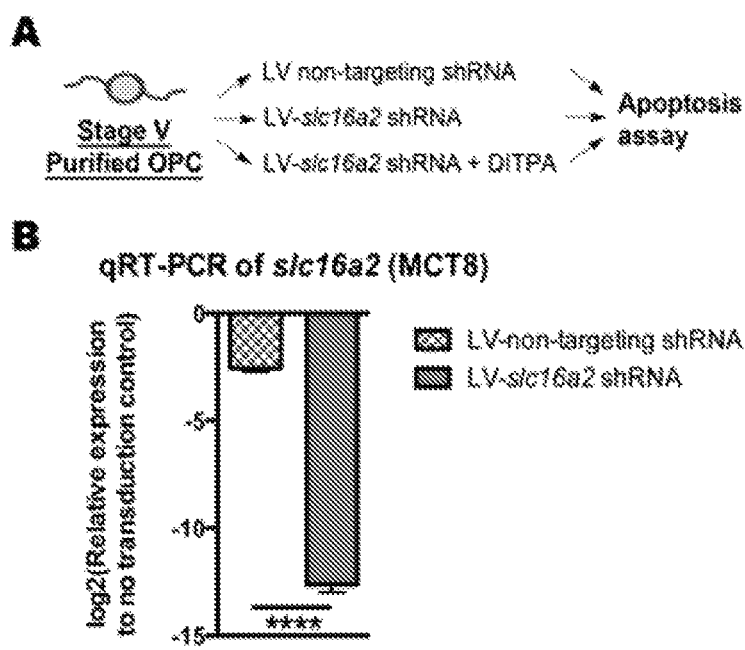

DITPA Limits OL Cell Death Caused by slc16a2 Down-Regulation and Promotes Myelination Under these Conditions Along with the pharmacological blockade of MCT8, the inventors stably knocked down slc16a2 to mimic the deprivation conditions that these cells would experience in the CNS of AHDS patients. They then tested the potential of DITPA in promoting myelination under the MCT8-deprived conditions (FIGS. 7, 14). For stable knock-down of slc16a2, the inventors generated a lentivirus (LV) carrying the shRNA-slc16a2 with a mCherry reporter (slc16a2 shRNA—FIG. 7A). Knock-down efficiency was verified with qRT-PCR which resulted in ~10-fold down-regulation of slc16a2 when compared with LV incorporating non-targeting shRNA (FIG. 14B). Since, the inventors found significant cell death upon pharmacological blockade of MCT8, they performed an apoptosis assay using an antibody against cleaved caspase-3, 5 days post-LV-transduction of these cells (FIG. 7). In-keeping with the data generated for pharmacological blockade of MCT8, knock-down of slc16a2 also caused significant death of mCherry+ cells (cleaved caspase 3+ with retracted processes). However, the administration of DITPA from 3 days post-LV-transduction significantly reduced cell death (FIGS. 7B-C), indicating DITPA bypasses MCT8 deprivation to support survival of maturing OLs at least in culture.

Finally, to test whether DITPA bypasses MCT8 to potentiate myelination, the inventors set up the same co-culture experiment where rat RGCs were cultured with slc16a2 down-regulated OLs (post-LV-transduction) from Nkx2.1-GFP+ sorted cells at stage V day 14 (FIGS. 7D-F). The inventors treated the cultures with $T_3$, DITPA or, $T_3$+DITPA, on the day of co-culture and these were maintained for 7 days. mCherry+/MBP+ myelinating OLs and mCherry+/MBP+ myelin segments were found only in DITPA or $T_3$+DITPA treated cultures (FIGS. 7E-F), indicating that DITPA can still promote differentiation of OLs that lack MCT8 expression and moreover, can still establish the myelination of axons.

Figure 15:
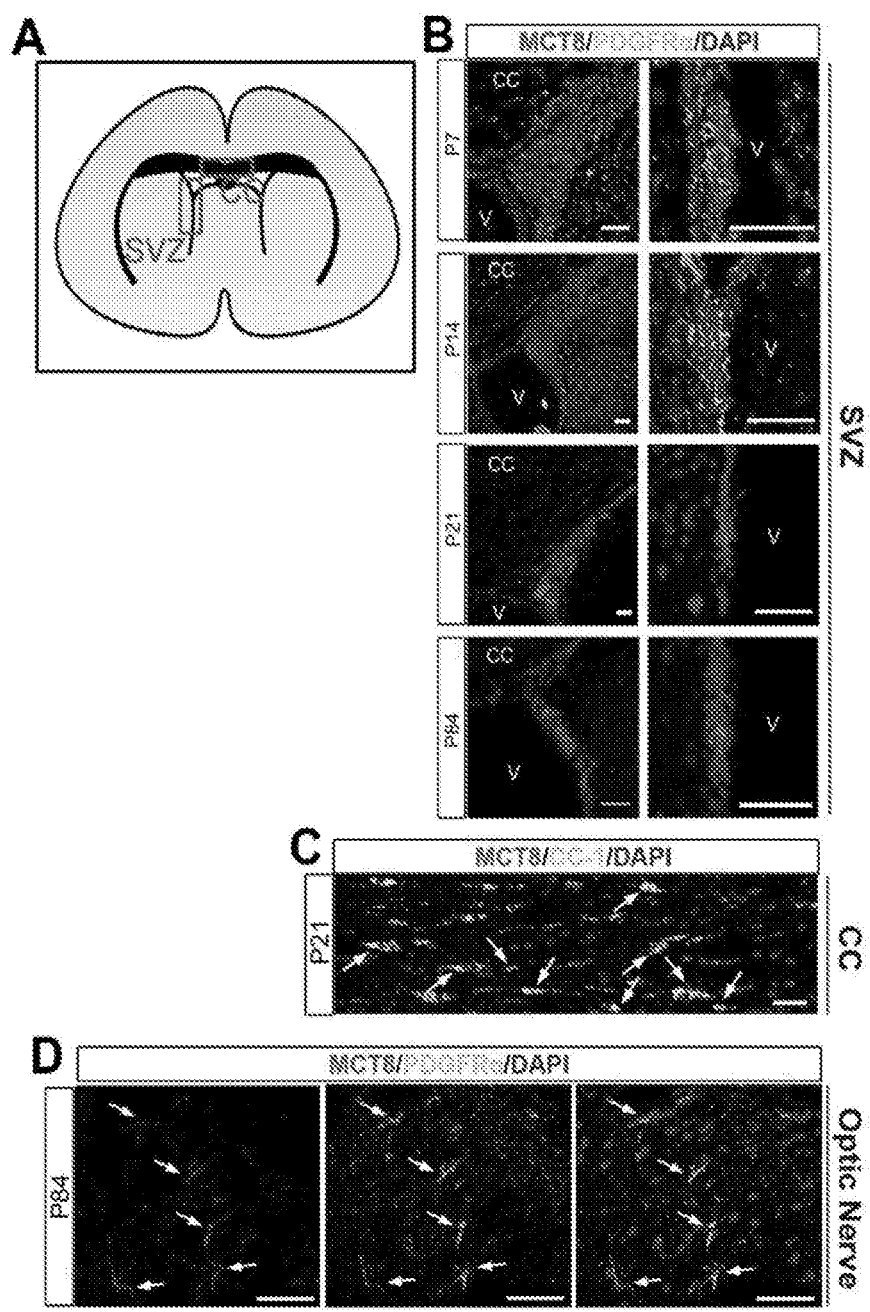
Figure 16:
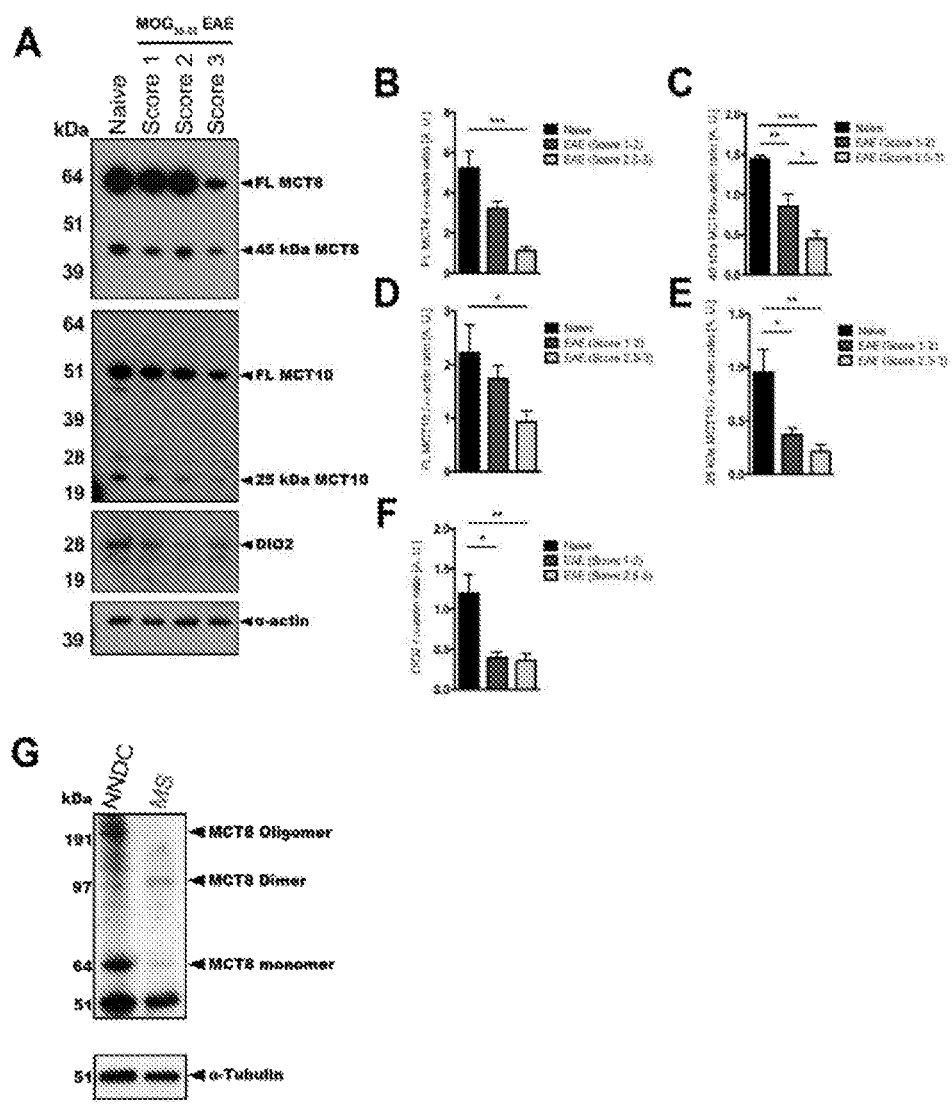

MCT8 is Expressed in OPCs During Development from the SVZ and Downregulated in Progressive EAE and MS Tissue To potentiate oligodendrocyte differentiation, the TH analog, DITPA, that bypasses the major TH transporter MCT8, was extensively studied. From this study, it seems that human oligodendrocytes require MCT8 for their maintenance, differentiation and myelination. Furthermore, the major finding of this study is that DITPA is capable of driving oligodendrocyte differentiation and myelination even in the absence of MCT8. To support in vitro oligodendroglial expression of MCT8, I performed an in vivo expression study of MCT8 during postnatal mouse brain development. From this, a specific expression of MCT8 in postnatal OPCs within the sub-ventricular zone (SVZ) during postnatal development, mature oligodendrocytes within the corpus callosum (CC) white matter tract and adult OPCs within the optic nerve were found (FIG. 15). Of interest, MCT8 expression seems to be maintained in cells residing within the SVZ throughout development, suggesting for its role in their maintenance (FIG. 15). Intriguingly, although it requires further validation, it seems that in EAE and MS, local cellular hypothyroidism associated with reduced cellular TH transport is suspected as the expression level of MCT8, MCT10, and DIO2 was found to be reduced during EAE and MS progression (FIG. 16). For a translational perspective, DITPA holds great promise as it has already passed phase I clinical trials for treating patients with AHDS (Verge et al., 2012). Therefore, given enough evidence of dysregulation of TH transport during neuroinflammation, DITPA could well be immediately utilized in an attempt to enhance remyelination in MS.

Discussion

Critical stages of the perinatal period govern brain development, where axons organized in fascicles are myelinated over several years, thereby appropriating time-dependent cognitive and motor functions. Hence, it is not surprising that the development of the fetal thyroid gland and circulating levels of THs are indeed elevated by the late gestational age, with maternal contributions delivered through the placenta (for review, see Bernal, 2007; Moog et al., 2015). Similarly, OL development coincides with circulating and CNS-specific fetal TH (Bernal, 2007). Despite the co-dependency of circulating and intracellular TH for brain development, oligodendrogenesis and myelination, the fact remains that both $T_3$ and $T_4$ need to enter developing neural cells to exert their genomic and non-genomic effects. In this study the inventors show for the first time that OL development can be intrinsically controlled by the function of the TH membrane transporter, MCT8. They identified that specific MCT8-deficiency in human OPCs can promote their cell death and that addition of the TH analog, DITPA can bypass such a deficiency to salvage OPCs and still promote their maturity toward myelinating OL.

These data argue that down-regulation of oligodendroglial differentiation repressor genes of the Wnt/Notch signaling pathways can be achieved upon the administration of DITPA to hESC-derived OPCs. This raises the tantalizing hypothesis that DITPA can lift the repression imposed on myelin gene expression during OL development (Chew et al., 2011). Supporting this contention, the inventors identified the up-regulations of WNT antagonists frzb, sfrp1, and sfrp2 with DITPA treatment, again underpinning how DITPA can promote OL differentiation. However, recent evidence strongly suggests that in gastrointestinal tumors, the increased β-catenin/Tcf4 levels not only correlate with reduced TR□1 transcriptional activity on its target genes but are also likely responsible for the shift of TRβ1 binding on Wnt targets (Sirakov et al., 2012) demonstrating a regulatory role for TH nuclear signaling in the cell cycle, all-be-it in a tumor cell line. Whether there is a causative effect of TH on Wnt or Notch pathways in neural cell differentiation including the derivation of mature OLs, has yet to be proven.

Along with the evidence supporting the action of TH directly on OL differentiation (Barres et al., 1994), $T_3$ may affect OPC proliferation dependant on the cells' specific stage of development (Baas et al., 1997). OPCs have been shown to exhibit a limited number of divisions before terminal differentiation, with TH and retinoic acid acting as external signals that influence this timing (Ahlgren et al., 1997). In particular, downstream signaling through TRα1 is fundamental since it has been shown that in tra1$^{-/-}$ mice, OPCs fail to differentiate in vitro in response to TH (Billon et al., 2002). The inventors' data show that the effect of $T_3$ on developing OLs derived from hESCs, is primarily seen from Stages V-VI, when the pre-OL marker O4 is expressed, coinciding with robust expression of the $T_3$ membrane transporter MCT8. The inventors showed that these O4+ OPCs consisted of a higher proportion of cells in S-phase, suggesting that $T_3$ stimulation potentiates proliferation at this stage of development. However, the inventors showed that down-regulation of, or functional blockade of MCT8 promotes cell death of OPCs, identifying the cell membrane-transport of $T_3$ as integral to the expansion or depletion of OL populations. Intriguingly, the inventors identified that the administration of DITPA to hESC-derived OPCs and other neural cell populations promoted the up-regulation of thrb and dio3 suggesting that bypassing MCT8 can still potentiate TH genomic signaling in the context of OL maturation and myelin gene expression, similar to that observed by other thyromimetics (Baxi et al., 2014). These data also corroborate the preferential switch of TR isoforms from a to 13 with regard to OL maturation and myelination (Baas et al., 2002).

Despite the developmental dependency of OPCs on $T_3$, no evidence exists for MCT8 during oligodendrogenesis and myelination. In mice, MCT8 facilitates the entry of TH into the brain parenchyma across the blood brain-barrier (BBB) (Ceballos et al., 2009) and, at a cellular level, the entry of TH into neurons in a region-specific manner (Trajkovic et al., 2007), where MCT8 is responsible for 75% of $T_3$ uptake (Wirth et al., 2009). The importance of MCT8 for neurodevelopment was unequivocally demonstrated in patients genetically identified as AHDS, phenotypically characterized by severe mental retardation with delayed myelination despite high levels of circulating $T_3$ with normal or low free $T_4$ concentrations (Vaurs-Barriere et al., 2009). In AHDS patients, the hypothyroid environment within the CNS, as a consequence of the MCT8 defect, cannot be corrected with $T_3/T_4$ therapies; indeed, $T_3/T_4$ supplements can lead to thyrotoxicosis in peripheral tissues such as the liver and heart where MCT8 has a diminished role in $T_3$ uptake (Biebermann et al., 2005). It is indeed evident that the activity of MCT8 plays a critical role, particularly in the human brain, to mediate the uptake of $T_3$ across the plasma membrane. This influences the intracellular concentration of active $T_3$ (Visser, 2013). The inventors' findings argue that the availability of $T_3$ to OPCs specifically can be restricted by a lack of functional MCT8 and as identified in this study, can potentiate OL dystrophy.

An important implication for the effect of limited MCT8 function on myelin formation was established in a developmental zebrafish model where the ablation of the slc16a2 gene rendered a OL maturation and myelin defect with associated locomotor and behavioural deficits (Zada et al., 2014). Indeed these resemble the neurological outcomes observed in AHDS patients under T2-weighted MRI (Armour et al., 2015). It therefore appears that the zebrafish model may mimic the human TH regulation more closely than that exhibited in the mouse. This is evident since the slc16a2$^{-/-}$ mouse model does not develop the neurological manifestations of AHDS patients, and has since been identified that in the mouse the CNS compensates for the loss of MCT8 through OATP1c1, an organic anion transporting polypeptide also capable of transporting $T_4$ across the BBB and a compensatory increase in the astrocytic deiodinase 2, converting $T_4$ to $T_3$ (Trajkovic et al., 2007). This was confirmed recently in a slc16a2/oatp1c1 double knockout exhibited the neurological deficits characteristic of AHDS, with reduced $T_3$ and $T_4$ uptake within the CNS and deiodinase activity with classical myelin delay (Mayerl et al., 2014). The inventors' data support the effects seen in the zebrafish experimental paradigm since our hESC-derived OPCs had limited differentiation and myelinogenic potential following the acute LV-mediated shRNA knockdown of the slc16a2 gene. Of greatest importance was the finding that DITPA treatment of the slc16a2$^{-/-}$ zebrafish restored myelin deficiencies and locomotor behavioral outcomes (Zada et al., 2014). These data corroborate the inventors' findings that DITPA can potentiate OL differentiation and myelination in the absence of MCT8.

The current research (disclosed here) has uncovered the biological outcomes of the DITPA when administered to differentiating OPCs. These cell-specific effects were the direct result of facilitated transcriptional regulation of OL differentiation and eventual myelination of CNS axons that could not be matched by $T_3$ administration alone. The most profound pharmacological property of DITPA was that it was capable of salvaging OPCs deficient in MCT8 with a unique capacity to continue their differentiation towards myelination. These findings provide proof-of-principle data for the treatment of severe inherited neurodevelopmental disorders where TH metabolism is dysfunctional, such as the well-established CNS hypothyroid state occurring in AHDS afflicted children.

Experimental Procedures hESC Culture

The inventors used two distinct lines of hESC for this study, Hes3 and Nkx2.1-GFP reporter line derived from Hes3 (Goulburn et al., 2011). hESC studies were approved by Monash University Human Research Ethics Committee.

Derivation of OPCs

OPCs were generated from Nkx2.1-GFP reporter line using our modified protocol from (Chaerkady et al., 2011; Kerr et al., 2010). A detailed protocol is described in Supplemental Experimental Procedures.

Immunocytochemistry

Preparations of cultures for immunolabeling are described in Supplemental Experimental Procedures.

Flow Cytometry

Preparations of cells for flow cytometry are described in Supplemental Experimental Procedures.

Fluorescence-Activated Cell Sorting (FACS)

The rationale and detailed protocol for Nkx2.1-based sorting is described in Supplemental Experimental Procedures. At the end of stage III of hESC differentiation, Nkx2.1-GFP+ cells were sorted on BD Influx (BD Biosciences). The sorted cells; GFP− and GFP+ cells were collected in stage IV medium with 10 μM Y27632 (Enzo) then further differentiated.

Microarray Analysis

H9-derived hOPCs (Merck/Millipore) were differentiated for 4 weeks and the following treatments were administered to the cells for 48 hours: Medium with 0.01% absolute ethanol control; 1 ng/mL DITPA (DITPA 1 ng/mL); 10 ng/mL DITPA (DITPA 10 ng/mL); or 100 ng/mL DITPA (DITPA 100 ng/mL). 1 µg of collected mRNA from each population was hybridized to Human HT-12 v3.0 Gene Expression BeadChip (Illumina) according to the manufacturer's instruction (For detailed procedure see Supplemental Experimental Procedures).

Cell Cycle Analysis with BrdU

BrdU cell cycle analysis was performed according to the manufacturer's protocol (BD Biosciences). For a detailed protocol, see Supplemental Experimental Procedures.

Stable Knockdown of slc16a2

Nkx2.1-GFP sorted cells at the end of stage VI or V were transduced with MOI of 10 in appropriate stage-specific medium containing polybrene (5 µg/mL, Sigma-Aldrich). Efficiency of transduction was validated by analyzing mCherry+ cells by flow cytometry and efficiency of knockdown was validated by analyzing the slc16a2 transcript level by qRT-PCR 72 hours post-transduction. An apoptosis assay was performed on cells either, treated with or without DITPA for 2 days from 72 hours post-transduction, then fixed. Cells were stained with monoclonal rat anti-mCherry (M11217, Life Technologies, 1:1,000), polyclonal rabbit anti-cleaved caspase-3 (9661, Cell Signaling Technology, 1:400) and DAPI (Life Technologies) then analyzed by confocal microscopy (Nikon A1 Inverted using a ×20 water objective lens). Apoptotic OLs were defined as those mCherry-positive cells with cleaved caspase-3+ nuclei that were also condensed and fragmented as assessed by DAPI. The data were plotted as the number of cleaved caspase-3/mCherry+ cells divided by total number of mCherry+ cells.

Co-Culture and Myelination Assays with Rat RGC and hESC-Derived OPCs

Retinae were dissected from P6 Sprague-Dawley rat pups (AEC #1121/2011/M). RGCs were purified according to the published immunopanning protocol (Deliyanti and Wilkinson-Berka, 2015; Watkins et al., 2008). Details of the RGC preparation are described in Supplemental Experimental Procedure. The RGC growth medium was changed every third day and cultures were maintained for 9 days. Pre-OLs from Nkx2.1-GFP+ cells at stage VI day 10, were FACS sorted according to O4 antibody labeling. O4+ sorted cells were then co-cultured with RGCs at a density of 20,000/well under 3 different conditions: $T_3$ with 0.01% ethanol, 10 ng/mL DITPA, and 40 ng/mL $T_3$ with DITPA in myelination medium (see Supplemental Experimental Procedure). The medium was changed every 3 days and all co-cultures were fixed after 7 days, followed by immunocytochemistry. Cells were stained with a monoclonal rat anti-mCherry (Life Technologies, M11217, 1:1,000); monoclonal mouse anti-NF-200 (Sigma-Aldrich, N0142, 1:200); and polyclonal rabbit anti-MBP (Millipore, AB980, 1:200). Followed by incubation of appropriate Alexa Fluor-labeled secondary antibodies (Life technologies).

Quantification of Myelination in Culture

In RGC-OPC co-cultures, myelin segments were counted manually. 10 fields (×20 objective) were randomly selected and captured from each coverslip with a confocal microscope (Nikon A1 inverted). For representative images, 10 z-stack images (0.25 µm intervals) were captured, analysed and processed for 3D volume rendering by Imaris version 7.6.4. OLs were scored according to their morphology and defined as either "resting" (processes not touching axons); "contacting" (processes touching axons but not wrapping); and "ensheathing" (processes aligned with and wrapping axons). A myelination index (i.e. axons myelinated) was calculated by: the number of MBP+ membrane, ensheathing the NF200+ axons/the total number of NF200+ axons.

For quantification of myelination in vitro following knockdown of slc16a2, at least nine fields (×20 objective) were randomly selected and captured from each coverslip with a confocal microscope (Nikon A1 inverted). A myelination index (%) by mCherry+ cells (i.e. axons myelinated by mCherry+ cells) was calculated by: the number of mCherry+/MBP+ membrane, ensheathing the NF200+ axons/the total number of NF200+ axons. Furthermore, the viable ensheathing mCherry+/MBP+ OLs and mature mCherry+ OLs according to their morphology with multiple processes and membranous sheaths were counted and their % calculated.

Statistical Analysis

Data are presented as mean±SEM. Two-way ANOVA with Tukey's multiple comparison test determined statistical significance, unless otherwise stated. A P value of <0.05 was considered as statistically significant. Graph Pad Prism version 6.0c software was used for statistical analysis of the data.

REFERENCES

Ahlgren, S. C., Wallace, H., Bishop, J., Neophytou, C., and Raff, M. C. (1997). Effects of thyroid hormone on embryonic oligodendrocyte precursor cell development in vivo and in vitro. Mol Cell Neurosci 9, 420-432.

Alsanie, W. F., Niclis, J. C., and Petratos, S. (2013). Human embryonic stem cell-derived oligodendrocytes: protocols and perspectives. Stem Cells Dev 22, 2459-2476.

Armour, C. M., Kersseboom, S., Yoon, G., and Visser, T. J. (2015). Further Insights into the Allan-Herndon-Dudley Syndrome: Clinical and Functional Characterization of a Novel MCT8 Mutation. PLoS One 10, e0139343.

Baas, D., Bourbeau, D., Sarlieve, L. L., Ittel, M. E., Dussault, J. H., and Puymirat, J. (1997). Oligodendrocyte maturation and progenitor cell proliferation are independently regulated by thyroid hormone. Glia 19, 324-332.

Baas, D., Legrand, C., Samarut, J., and Flamant, F. (2002). Persistence of oligodendrocyte precursor cells and altered myelination in optic nerve associated to retina degeneration in mice devoid of all thyroid hormone receptors. Proc Natl Acad Sci USA 99, 2907-2911.

Baas, D., Prufer, K., Ittel, M. E., Kuchler-Bopp, S., Labourdette, G., Sarlieve, L. L., and Brachet, P. (2000). Rat oligodendrocytes express the vitamin D(3) receptor and respond to 1,25-dihydroxyvitamin D(3). Glia 31, 59-68.

Barres, B. A., Lazar, M. A., and Raff, M. C. (1994). A novel role for thyroid hormone, glucocorticoids and retinoic acid in timing oligodendrocyte development. Development 120, 1097-1108.

Baxi, E. G., Schott, J. T., Fairchild, A. N., Kirby, L. A., Karani, R., Uapinyoying, P., Pardo-Villamizar, C., Rothstein, J. R., Bergles, D. E., and Calabresi, P. A. (2014). A selective thyroid hormone beta receptor agonist enhances human and rodent oligodendrocyte differentiation. Glia 62, 1513-1529.

Bernal, J. (2007). Thyroid hormone receptors in brain development and function. Nat Clin Pract Endocrinol Metab 3, 249-259.

Biebermann, H., Ambrugger, P., Tarnow, P., von Moers, A., Schweizer, U., and Grueters, A. (2005). Extended clinical phenotype, endocrine investigations and functional studies of a loss-of-function mutation A150V in the thyroid hormone specific transporter MCT8. Eur J Endocrinol 153, 359-366.

Billon, N., Jolicoeur, C., Tokumoto, Y., Vennstrom, B., and Raff, M. (2002). Normal timing of oligodendrocyte development depends on thyroid hormone receptor alpha 1 (TRalpha1). Embo J 21, 6452-6460.

Braun, D., Kim, T. D., le Coutre, P., Kohrle, J., Hershman, J. M., and Schweizer, U. (2012). Tyrosine kinase inhibitors noncompetitively inhibit MCT8-mediated iodothyronine transport. J Clin Endocrinol Metabo 97, E100-105.

Ceballos, A., Belinchon, M. M., Sanchez-Mendoza, E., Grijota-Martinez, C., Dumitrescu, A. M., Refetoff, S., Morte, B., and Bernal, J. (2009). Importance of monocarboxylate transporter 8 for the blood-brain barrier-dependent availability of 3,5,3'-triiodo-L-thyronine. Endocrinology 150, 2491-2496.

Chaerkady, R., Letzen, B., Renuse, S., Sahasrabuddhe, N. A., Kumar, P., All, A. H., Thakor, N. V., Delanghe, B., Gearhart, J. D., Pandey, A., et al. (2011). Quantitative temporal proteomic analysis of human embryonic stem cell differentiation into oligodendrocyte progenitor cells. Proteomics 11, 4007-4020.

Chew, L. J., Shen, W., Ming, X., Senatorov, V. V., Jr., Chen, H. L., Cheng, Y., Hong, E., Knoblach, S., and Gallo, V. (2011). SRY-box containing gene 17 regulates the Wnt/beta-catenin signaling pathway in oligodendrocyte progenitor cells. J Neurosci 31, 13921-13935.

Deliyanti, D., and Wilkinson-Berka, J. L. (2015). Inhibition of NOX1/4 with GKT137831: a potential novel treatment to attenuate neuroglial cell inflammation in the retina. J Neuroinflammation 12, 136.

Dumitrescu, A. M., Liao, X. H., Best, T. B., Brockmann, K., and Refetoff, S. (2004). A novel syndrome combining thyroid and neurological abnormalities is associated with mutations in a monocarboxylate transporter gene. Am J Human Genet 74, 168-175.

Dumitrescu, A. M., Liao, X. H., Weiss, R. E., Millen, K., and Refetoff, S. (2006). Tissue-specific thyroid hormone deprivation and excess in monocarboxylate transporter (mct) 8-deficient mice. Endocrinology 147, 4036-4043.

Friesema, E. C., Ganguly, S., Abdalla, A., Manning Fox, J. E., Halestrap, A. P., and Visser, T. J. (2003). Identification of monocarboxylate transporter 8 as a specific thyroid hormone transporter. J Biol Chem 278, 40128-40135.

Friesema, E. C., Grueters, A., Biebermann, H., Krude, H., von Moers, A., Reeser, M., Barrett, T. G., Mancilla, E. E., Svensson, J., Kester, M. H., et al. (2004). Association between mutations in a thyroid hormone transporter and severe X-linked psychomotor retardation. Lancet 364, 1435-1437.

Friesema, E. C., Jansen, J., Jachtenberg, J. W., Visser, W. E., Kester, M. H., and Visser, T. J. (2008). Effective cellular uptake and efflux of thyroid hormone by human monocarboxylate transporter 10. Mol Endocrinol 22, 1357-1369.

Friesema, E. C., Kuiper, G. G., Jansen, J., Visser, T. J., and Kester, M. H. (2006). Thyroid hormone transport by the human monocarboxylate transporter 8 and its rate-limiting role in intracellular metabolism. Mol Endocrinol 20, 2761-2772.

Gika, A. D., Siddiqui, A., Hulse, A. J., Edward, S., Fallon, P., McEntagart, M. E., Jan, W., Josifova, D., Lerman-Sagie, T., Drummond, J., et al. (2010). White matter abnormalities and dystonic motor disorder associated with mutations in the SLC16A2 gene. Dev Med Child Neurol 52, 475-482.

Goulburn, A. L., Alden, D., Davis, R. P., Micallef, S. J., Ng, E. S., Yu, Q. C., Lim, S. M., Soh, C. L., Elliott, D. A., Hatzistavrou, T., et al. (2011). A targeted NKX2.1 human embryonic stem cell reporter line enables identification of human basal forebrain derivatives. Stem Cells 29, 462-473.

Kerr, C. L., Letzen, B. S., Hill, C. M., Agrawal, G., Thakor, N. V., Sterneckert, J. L., Gearhart, J. D., and All, A. H. (2010). Efficient differentiation of human embryonic stem cells into oligodendrocyte progenitors for application in a rat contusion model of spinal cord injury. Int J Neurosci 120, 305-313.

Kinne, A., Kleinau, G., Hoefig, C. S., Gruters, A., Kohrle, J., Krause, G., and Schweizer, U. (2010). Essential molecular determinants for thyroid hormone transport and first structural implications for monocarboxylate transporter 8. J Biol Chem 285, 28054-28063.

Laeng, P., Decimo, D., Pettmann, B., Janet, T., and Labourdette, G. (1994). Retinoic acid regulates the development of oligodendrocyte precursor cells in vitro. J Neurosci Res 39, 613-633.

Lopez-Espindola, D., Morales-Bastos, C., Grijota-Martinez, C., Liao, X. H., Lev, D., Sugo, E., Verge, C. F., Refetoff, S., Bernal, J., and Guadano-Ferraz, A. (2014). Mutations of the thyroid hormone transporter MCT8 cause prenatal brain damage and persistent hypomyelination. J Clin Endocrinol Metab 99, E2799-2804.

Mayerl, S., Muller, J., Bauer, R., Richert, S., Kassmann, C. M., Darras, V. M., Buder, K., Boelen, A., Visser, T. J., and Heuer, H. (2014). Transporters MCT8 and OATP1C1 maintain murine brain thyroid hormone homeostasis. J Clin Invest 124, 1987-1999.

Mi, S., Lee, X., Hu, Y., Ji, B., Shao, Z., Yang, W., Huang, G., Walus, L., Rhodes, K., Gong, B. J., et al. (2011). Death receptor 6 negatively regulates oligodendrocyte survival, maturation and myelination. Nat Med 17, 816-821.

Moog, N. K., Entringer, S., Heim, C., Wadhwa, P. D., Kathmann, N., and Buss, C. (2015). Influence of maternal thyroid hormones during gestation on fetal brain development. Neuroscience. Published online Oct. 3, 2015 doi:10.1016/j.neuroscience.2015.09.070

Najm, F. J., Lager, A. M., Zaremba, A., Wyatt, K., Caprariello, A. V., Factor, D. C., Karl, R. T., Maeda, T., Miller, R. H., and Tesar, P. J. (2013). Transcription factor-mediated reprogramming of fibroblasts to expandable, myelinogenic oligodendrocyte progenitor cells. Nat Biotechnol 31, 426-433.

Ostrakhovitch, E. A., Olsson, P. E., Jiang, S., and Cherian, M. G. (2006). Interaction of metallothionein with tumor suppressor p53 protein. FEBS Lett 580, 1235-1238.

Pringle, N. P., Yu, W. P., Guthrie, S., Roelink, H., Lumsden, A., Peterson, A. C., and Richardson, W. D. (1996). Determination of neuroepithelial cell fate: induction of the oligodendrocyte lineage by ventral midline cells and sonic hedgehog. Dev Biol 177, 30-42.

Sirakov, M., Skah, S., Lone, I. N., Nadjar, J., Angelov, D., and Plateroti, M. (2012). Multi-level interactions between the nuclear receptor TRalpha1 and the WNT effectors beta-catenin/Tcf4 in the intestinal epithelium. PLoS One 7, e34162.

Trajkovic, M., Visser, T. J., Mittag, J., Horn, S., Lukas, J., Darras, V. M., Raivich, G., Bauer, K., and Heuer, H. (2007). Abnormal thyroid hormone metabolism in mice lacking the monocarboxylate transporter 8. J Clin Invest 117, 627-635.

Vaurs-Barriere, C., Deville, M., Sarret, C., Giraud, G., Des Portes, V., Prats-Vinas, J. M., De Michele, G., Dan, B., Brady, A. F., Boespflug-Tanguy, O., et al. (2009). Pelizaeus-Merzbacher-Like disease presentation of MCT8 mutated male subjects. Ann Neurol 65, 114-118.

Verge, C. F., Konrad, D., Cohen, M., Di Cosmo, C., Dumitrescu, A. M., Marcinkowski, T., Hameed, S., Hamilton, J., Weiss, R. E., and Refetoff, S. (2012). Diiodothyropropionic acid (DITPA) in the treatment of MCT8 deficiency. J Clin Endocrinol Metab 97, 4515-4523.

Visser, T. J. (2013). Thyroid hormone transporters and resistance. Endocr Dev 24, 1-10.

Visser, W. E., Friesema, E. C., Jansen, J., and Visser, T. J. (2008). Thyroid hormone transport in and out of cells. Trends Endocrinol Metab 19, 50-56.

Watkins, T. A., Emery, B., Mulinyawe, S., and Barres, B. A. (2008). Distinct stages of myelination regulated by gamma-secretase and astrocytes in a rapidly myelinating CNS coculture system. Neuron 60, 555-569.

Wirth, E. K., Roth, S., Blechschmidt, C., Holter, S. M., Becker, L., Racz, I., Zimmer, A., Klopstock, T., Gailus-Durner, V., Fuchs, H., et al. (2009). Neuronal 3',3,5-triiodothyronine (T3) uptake and behavioral phenotype of mice deficient in Mct8, the neuronal T3 transporter mutated in Allan-Herndon-Dudley syndrome. J Neurosci 29, 9439-9449.

Wosik, K., Antel, J., Kuhlmann, T., Bruck, W., Massie, B., and Nalbantoglu, J. (2003). Oligodendrocyte injury in multiple sclerosis: a role for p53. J Neurochem 85, 635-644.

Zada, D., Tovin, A., Lerer-Goldshtein, T., Vatine, G. D., and Appelbaum, L. (2014). Altered behavioral performance and live imaging of circuit-specific neural deficiencies in a zebrafish model for psychomotor retardation. PLoS genetics 10, e1004615.

FIGURE LEGENDS

FIG. 1. Nkx2.1-GFP hESC Reporter Line can be Directed Toward an OPC Fate (A) Directed differentiation of hESC into OPCs. (B) hESCs (stage I) were differentiated to neural embryoid bodies (EBs) (stage II) expressing (C, D) Nkx2.1. (E) Nestin+ neural precursor cells (stage III) were generated. (F) Olig2+ Glial precursor cells (stage IV) appeared under the influence of EGF. These were further differentiated into OPCs (stage V) expressing (G) PDGFRα and (H) NG2 through the addition of PDGF-AA. (I, J) $T_3$ promoted terminal differentiation of OPCs into (I) O4+ pre-OLs (stage VI), and (J) MBP+ pre-myelinating OLs. (E-J) Counterstaining was performed by DAPI. Scale bar=100 μm for (B-D) and 20 μm for (E-J).

Figure 2:
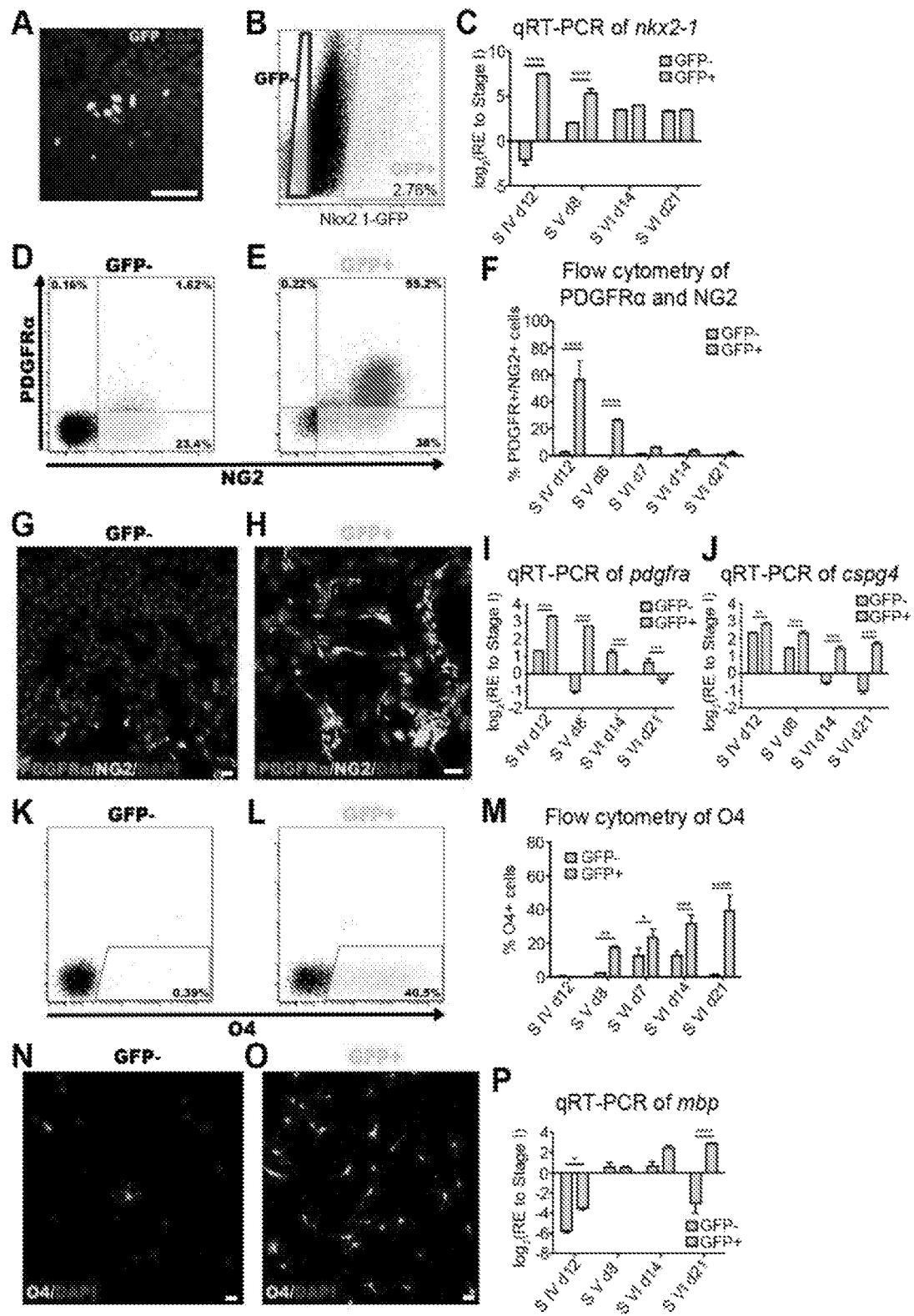

FIG. 2. Nkx2.1-GFP+ Sorted Cells were Differentiated Toward an Oligodendroglial Lineage (A) hESC-derived Nkx2.1-expressing cells were identified by immunolabeling for GFP followed by DAPI counterstaining. (B) GFP+ cells were FACS-sorted from GFP− cells at stage III, day 5. (C) qRT-PCR analysis of nkx2.1 post-sorting throughout differentiation. (D-E) Flow cytometric analysis of PDGFRα+/NG2+ OPCs in (D) the GFP− and (E) GFP+ populations at stage IV, day 12. (F) The proportion of PDGFRα+/NG2+ OPCs during differentiation. (G-H) Immunostaining for PDGFRα and NG2 on (G) GFP− and (H) GFP+ sorted cells at stage V, counterstained with DAPI. (I-J) qRT-PCR analyses of (I) pdgfra and (J) cspg4 throughout differentiation. (K-M) Flow cytometric analysis of O4 in (K) GFP− and (L) GFP+ sorted populations at stage VI, day 21. (M) The proportion of O4+ immature OLs throughout differentiation. (N-O) Immunostaining for O4 and DAPI on (N) GFP− and (O) GFP+ sorted populations. (P) qRT-PCR analysis of mbp throughout differentiation (RE; relative expression). *$P<0.05$; $P<0.01$; *$P<0.001$; ****$P<0.0001$; (n=3-4; mean±SEM). Scale bar=50 μm.

FIG. 3. MCT8 is Expressed on Immature and Pre-Myelinating OLs (A) Flow cytometric analysis showing expression of MCT8 in O4+ immature OLs derived from the GFP+ sorted population at stage VI, day 21. (B) The proportion of O4+/MCT8+ cells during differentiation (C) Western blot of cell lysates and conditioned medium from the GFP− and GFP+ sorted population at stage VI, day 21 with MCT8 and β-actin antibodies. (D) GFP+ sorted cells at stage VI, day 21 were immunostained with NG2, O4, or MBP, which were co-stained with MCT8 and DAPI counterstaining. The merged images demonstrate oligodendroglial expression of MCT8. (E) qRT-PCR analysis of slc16a2 during differentiation. *$P<0.05$; $P<0.01$; *$P<0.001$; ****$P<0.0001$; (n=3; mean±SEM). Scale bar=50 μm.

Figure 4:
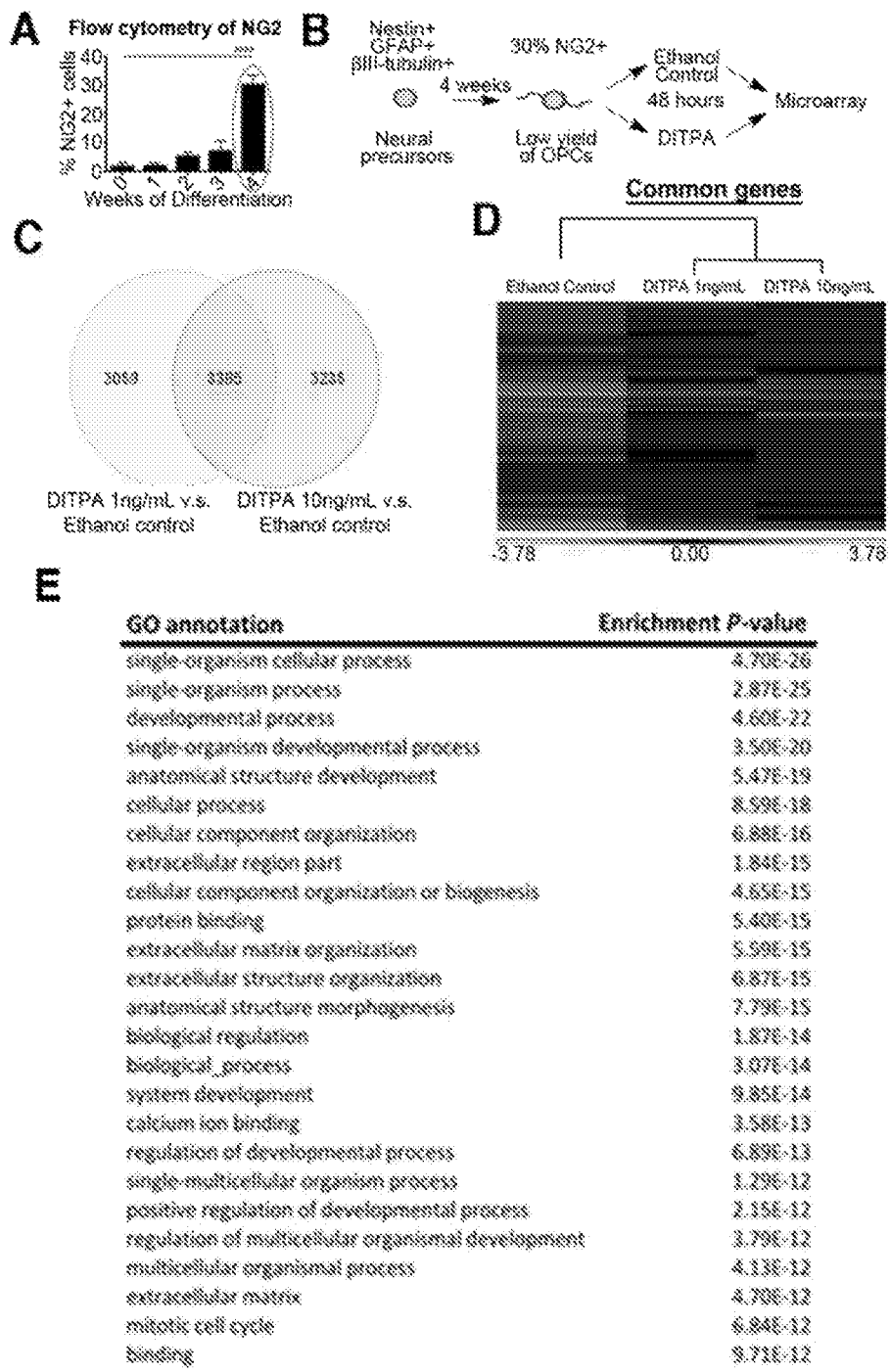
Figure 4:
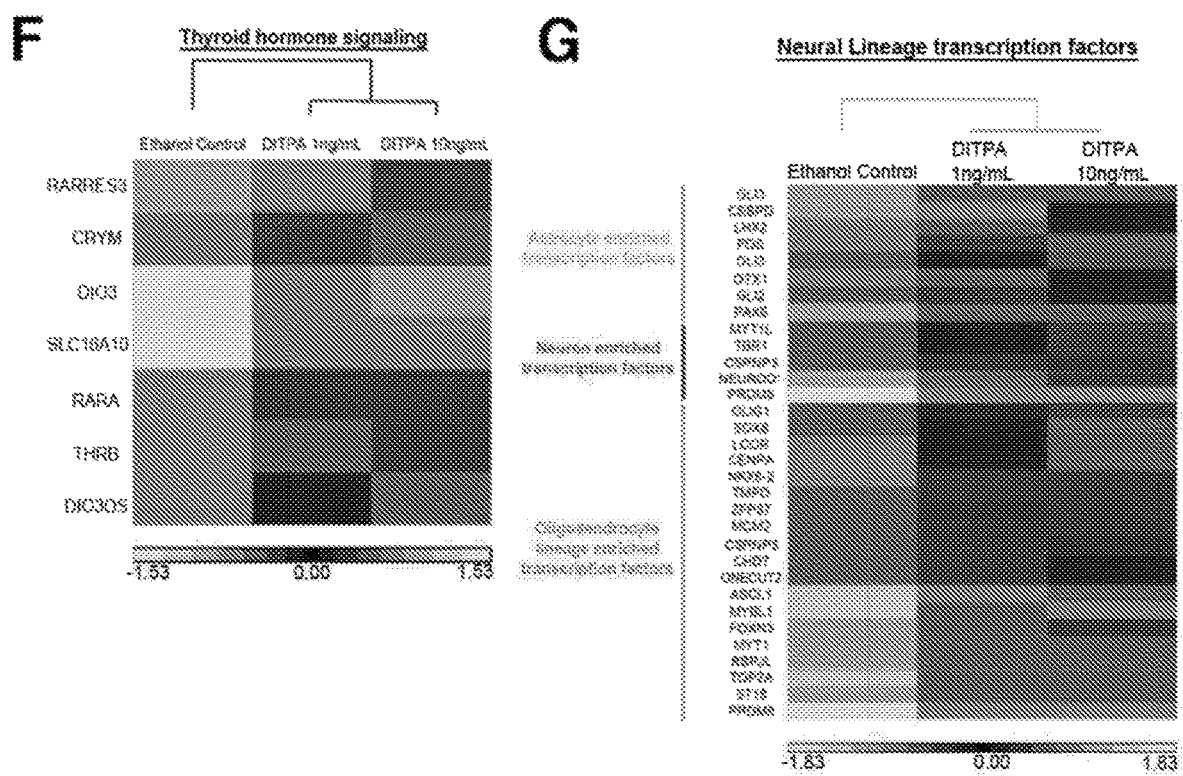

FIG. 4. Distinct Transcriptome Analysis for Human Mixed Neural Cell Cultures Differentiated Toward the OPC Lineage with or without DITPA.

(A) The proportion of NG2-positive cells during differentiation of Merck-Millipore human mixed neural cell cultures. One-way ANOVA with Tukey's post-hoc test; ****$P<0.0001$ (n=3-4; mean±SEM). At week 4, ~30% of NG2+ cells were derived and DITPA was treated (circled in red). (B) DITPA treatment regime upon human OPC specification from neural precursors. (C) Comparative gene expression profiles from different concentrations of DITPA versus ethanol control treatments. (D) Genome-wide transcriptional profile heatmap obtained for the different concentrations of DITPA and ethanol control treatments. (E) Highly enriched GO terms of commonly expressed genes following the administration of DITPA at 1 ng/mL and 10 ng/mL versus ethanol control. (F and G) Heatmap of (F) genes related to TH signaling and (G) Neuronal, astroglial and oligodendroglial enriched transcription factors (Gene lists are from (Najm et al., 2013)) following the administration DITPA and ethanol control.

Figure 5:
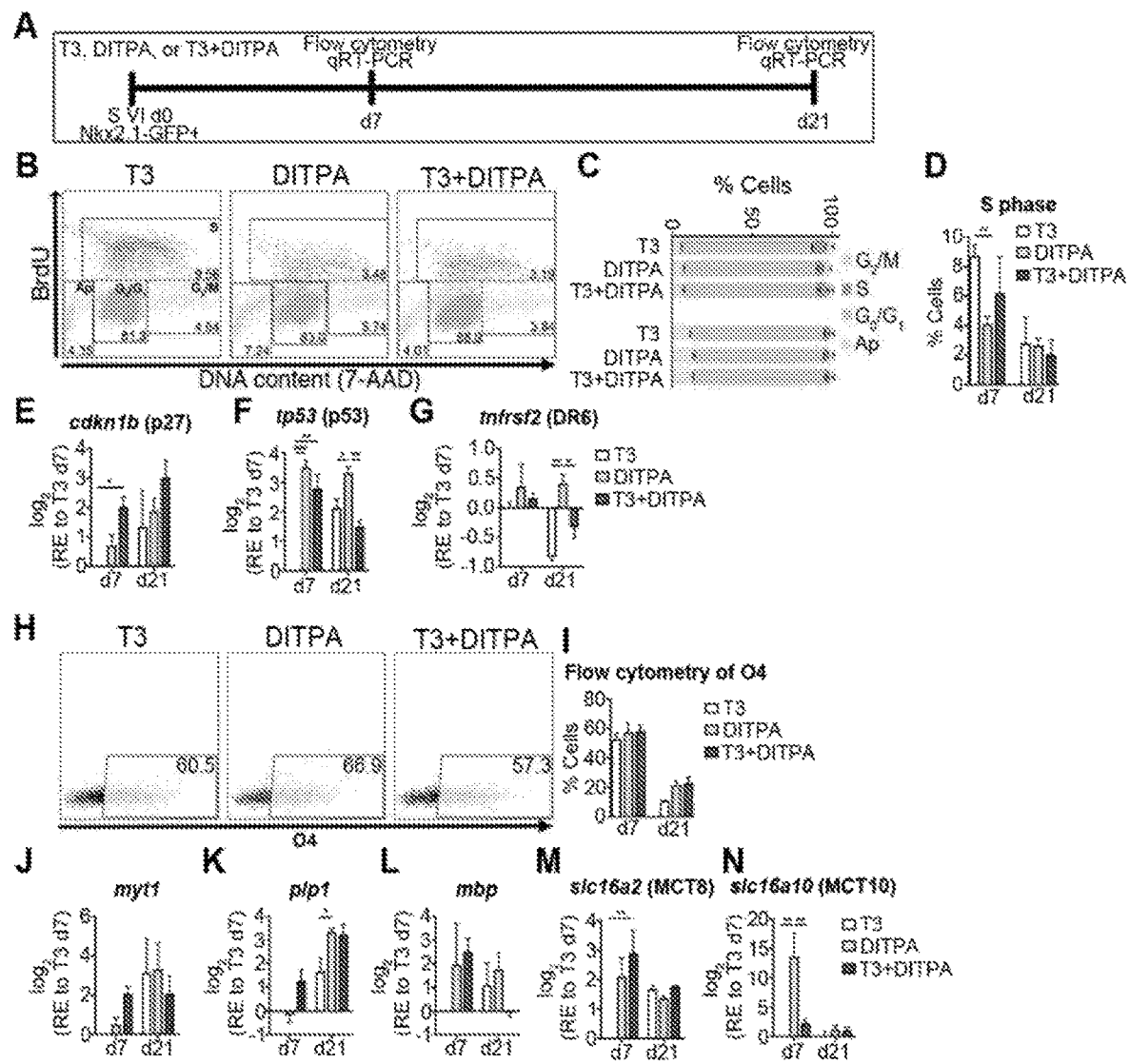

FIG. 5. DITPA Potentiates OPC Cycle Exit to Promote Differentiation in Enriched OL Cultures Derived from Nkx2.1-GFP+ Sorted hESCs (A) DITPA treatment regime throughout Stage VI. Cells were treated with either $T_3$ alone ($T_3$), DITPA alone (DITPA) or $T_3$ with DITPA ($T_3$+DITPA) then these were analyzed on days 7 and 21 post-treatments by flow cytometry and qRT-PCR. (B) Flow cytometric dot plots upon BrdU incorporation at day 7 of treatments (Ap; apoptotic cells). (C) The percentage of cells at the different cell cycle stages at days 7 and 21 post-treatments. (D) The percentage of cells in S phase (BrdU-positive) for the different treatment groups are shown. (E-G) qRT-PCR analyses of cell cycle-associated genes; (E) cdkn1b, (F) tp53 and (G) tnfrsf2, 7 and 21 days post-treatments. (H) Flow cytometric analysis of O4 at day 7 post-treatments. (I) The percentage of O4+ cells analyzed by flow cytometry at day 7 and 21 post p-treatments. (J-L) qRT-PCR analyses of myelin genes; (J) myt1, (K) plp1, (L) mbp, 7 and 21 days post-treatments. (M and N) qRT-PCR analyses of TH transporter genes; (M) slc16a2 (MCT8), and (N) slc16a10 (MCT10) 7 and 21 days post-treatments. *$P<0.05$; $P<0.01$; *$P<0.001$; (n=3; mean±SEM).

Figure 6:
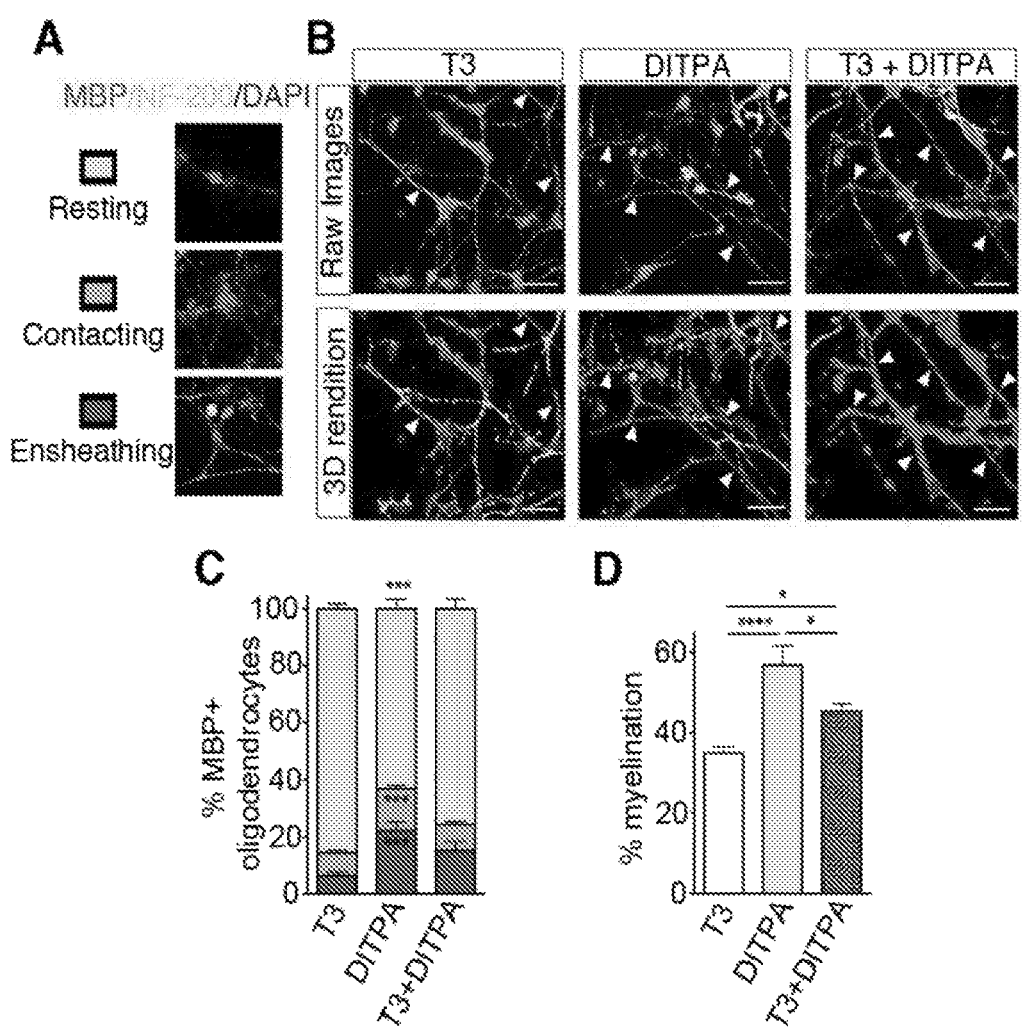

FIG. 6. DITPA Promotes the Myelination of Rat RGCs from Nkx2.1-GFP+ hESC Derived OPCs.

(A-D) At day 10, stage VI, OPCs from Nkx2.1-GFP+ sorted cells were seeded on rat RGCs and maintained for 7 days with $T_3$, DITPA, or $T_3$+DITPA treatment, then immunostained with MBP, NF-200, and DAPI. MBP+ OLs were scored for their morphology as (A) "Resting", "Contacting", or "Ensheathing". (B) Representative deconvoluted z-stack captured images from the myelinating co-cultures treated with $T_3$, DITPA or $T_3$+DITPA. For better representation, these z-stack images were rendered into an artificial 3D image and shown below as raw images (arrowhead indicates regions of myelination, scale bars=50 μm). (C) The percentage of MBP+ OLs that are resting, contacting, and ensheathing from the different treatment groups. (D) The percentage of myelination within the different treatment groups. One-way ANOVA with Tukey's post-hoc analysis; *$P<0.05$; *$P<0.001$; **$P<0.0001$; (n=9-10, mean±SEM).

FIG. 7. DITPA Rescues Oligodendroglial Cell Death Mediated by slc16a2 Knock Down and Under MCT8-Deficient Conditions can Still Promote Axon Myelination (A) Immunostaining for mCherry and cleaved caspase-3 (cl caspase-3) on Nkx2.1-GFP+ sorted OPCs at stage V, day 12 (3 days post-transduction with non-targeting shRNA, slc16a2-shRNA, or slc16a2-shRNA+DITPA) counterstained with DAPI. (B and C) The proportion of mCherry+/cl caspase-3+ apoptotic cells was significantly increased upon the lentivirus-transduction containing slc16a2-shRNA. DITPA treatment significantly reduced the slc16a2-shRNA-mediated apoptosis (n=3; mean±SEM). Scale bar=50 μm. (D) 3 days post-transduction with slc16a2-shRNA, OPCs from Nkx2.1-GFP+ sorted cells were seeded on rat RGCs and were maintained for 7 days with $T_3$, DITPA, or $T_3$+DITPA treatment, then immunostained with mCherry, MBP and NF-200 Scale bar=100 μm. Magnified images of single myelinated axons are shown on the right hand side of each image Scale bar=20 μm. (E) The percentage of overall myelination and mCherry+ myelination and (F) the percentages of ensheathing mCherry+/MBP+ OLs among the different treatment groups. One-way ANOVA with Tukey's post-hoc analysis; $P<0.01$; *$P<0.0001$; N.D.: not detected; (n=9-10, mean±SEM).

FIG. 8. Differential Expression of Nkx2.1 Transcription Factor During Stage II and III of Neural Derivation from hESC (A) Bright field microscopy images of Nkx2.1-GFP+ EBs at day 8, 10, 12 and 14 during stage II (Scale bar=100 μm). (B) The expression of the GFP reporter for the transcription factor Nkx2.1 was demonstrated by the mean intensity of fluorescence; i.e. GFP luminosity over the volume of EBs during stage II (n=5-7; mean±SEM). (C) The GFP fluorescence intensity of EBs was analyzed by flow cytometry during stage II and III. (D, E) qRT-PCR semi-quantitative analyses of the (D) nkx2.1 and (E) pax6 genes during stage II. One-way ANOVA with Tukeys' post-hoc test; $P<0.01$; **$P<0.0001$; (n=4-5; mean±SEM).

Figure 9:
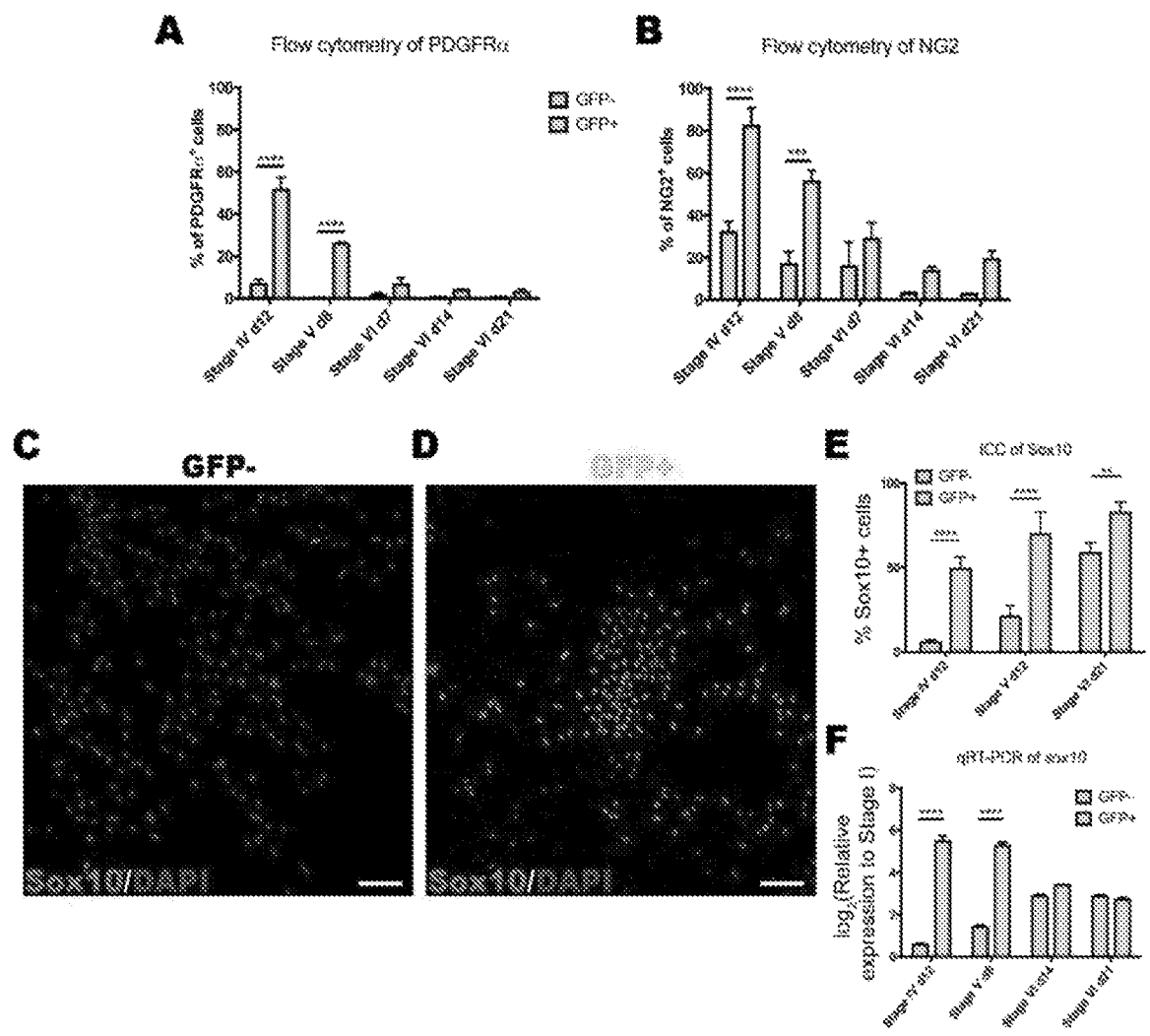

FIG. 9. Enhanced Yield for Both the Derived PDGFRα+ and NG2+ OPC Populations and Upregulation of Sox10 Following the Sorting of hESCs According to Nkx2.1-GFP+ Expression when Compared with the GFP− Sorted Population (Related to FIG. 2)

Flow cytometric analysis using antibodies against either (A) PDGFRα or (B) NG2, detecting both the Nkx2.1-GFP+ and GFP− sorted populations from stage IV to VI of hESC-derivation. Significantly higher percentages of OPCs were derived from the GFP+ compared with the GFP− sorted populations at the end of stage IV and during stage V (n=3; mean±SEM). (C-F) At day 12, stage V, the (C) GFP− and (D) GFP+ sorted cells were immunostained with the ubiquitous OL transcription factor, Sox10 (red) and counterstained with DAPI (blue). (E) Increased numbers of Sox10-positive cells in the GFP+ sorted population compared with that of the GFP− sorted population were found throughout OL differentiation. (F) qRT-PCR analysis of sox10 demonstrates significant upregulation during stage IV and V of differentiation. Data are represented as $\log_2$ of the average fold-change in relative gene expression up to stage I of differentiation. Two-way ANOVA with Tukeys' post-hoc test; $P<0.01$; *$P<0.001$; ****$P<0.0001$; (n=3; mean±SEM).

Figure 10:
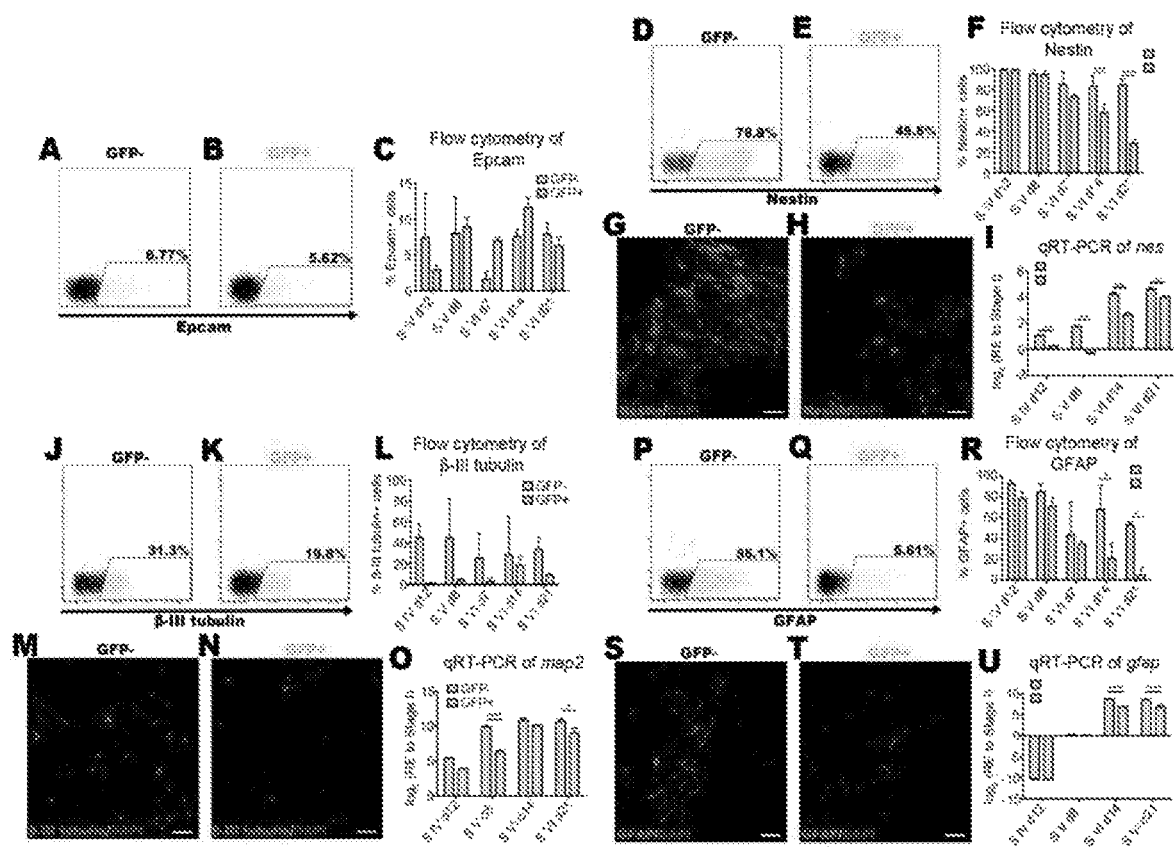

FIG. 10. Low Yields of Epcam+ Neuroepithelial Cells Derived from the GFP+ and GFP− Sorted Populations and GFP− Sorted hESCs Remain as Nestin+ Progenitors, or Alternatively, being Able to Preferentially Differentiate Toward β-III Tubulin+ Neurons, GFAP+ Astrocytes.

(A-C) Flow cytometric analysis of Epcam expression in the (A) GFP− and (B) GFP+ sorted cells at stage VI0 day 21 of differentiation. (C) The proportions of Epcam+ cells (%) during differentiation. (D-F) Flow cytometric analysis of Nestin expression between the (D) GFP− and (E) GFP+ sorted cells at stage VI, day 21 of differentiation. (F) The proportion of Nestin+ progenitors (%) during differentiation. (G-H) Immunostaining for Nestin (red) on (G) GFP− and (H) GFP+ sorted cells at stage VI day 21 of differentiation, counterstained with DAPI (blue). (I) qRT-PCR analysis of nes during differentiation. (J-L) Flow cytometric analysis of β-III-tubulin expression in (J) GFP− and (K) GFP+ sorted cells at stage VI, day 21. (L) The proportion of β-III-tubulin+ neurons (%) during differentiation. (M, N) Immunostaining for β-III-tubulin (red) between the (M) GFP− and (N) GFP+ sorted cells at stage VI day 21 of differentiation, counterstained with DAPI (blue). (O) qRT-PCR analysis of map2 during differentiation. (P-R) Flow cytometric analysis of GFAP expression between the (P) GFP− and (Q) GFP+ sorted cells at stage VI day 21 of differentiation. (R) The proportion of GFAP+ astrocytes (%) during differentiation. (S, T) Immunostaining for GFAP (red) between the (S) GFP− and (T) GFP+ sorted cells at stage VI day 21 of differentiation, counterstained with DAPI (blue). (U) qRT-PCR analysis of gfap during differentiation. Bar graphs generated for qRT-PCR analysis indicate log 2 of the average fold-change in gene expression compared with the undifferentiated hESCs. Two-way ANOVA with Tukeys' post-hoc test; *$P<0.05$; *$P<0.001$; **$P<0.0001$; (n=3-4; mean±SEM); Scale bars=100 μm.

Figure 11:
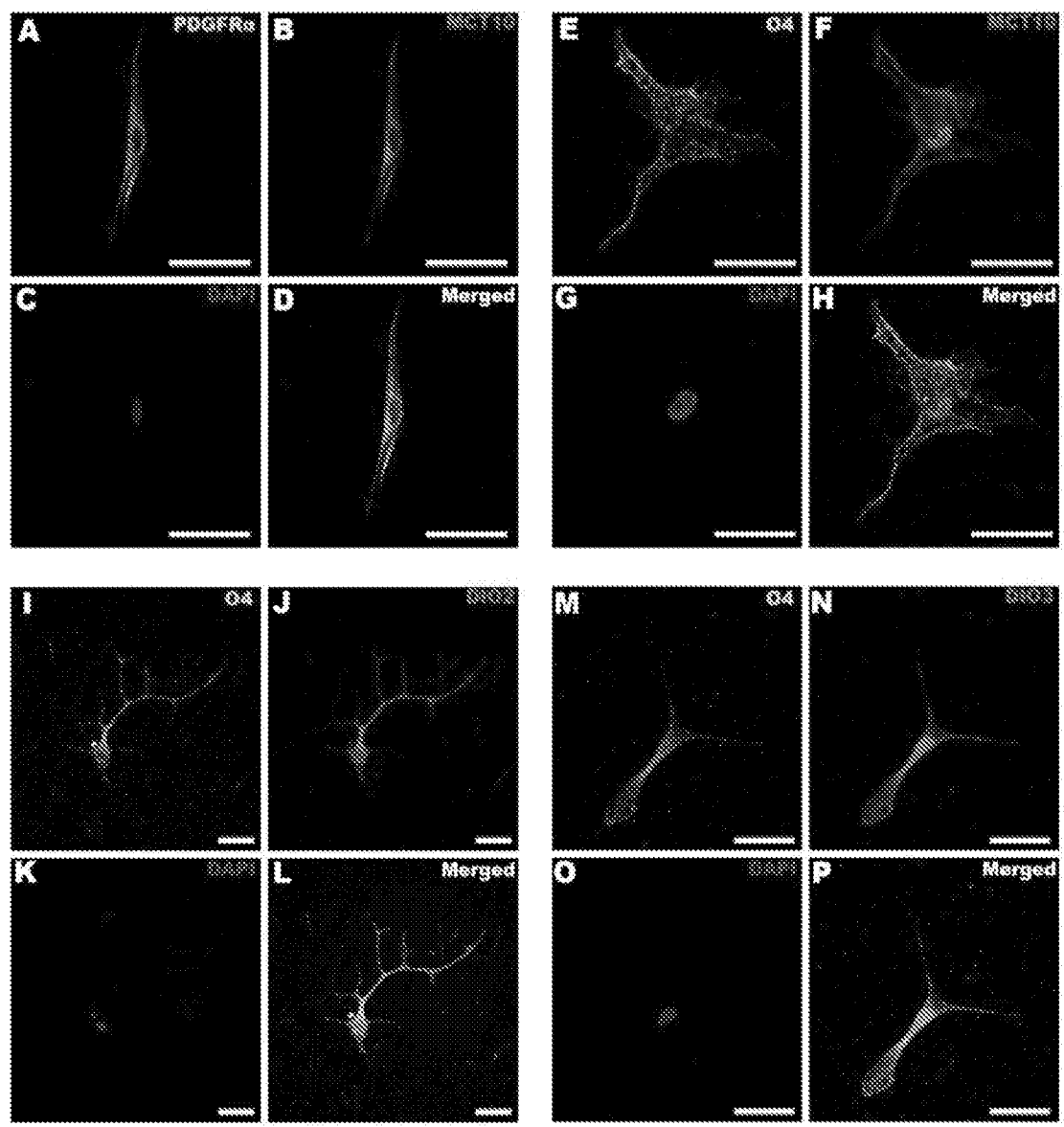

FIG. 11. MCT10, DIO2, and DIO3 are all Expressed in Oligodendroglial Lineage Cells (Related to FIG. 3)

(A-D) Nkx2.1-GFP+ sorted cells at day 12 of stage IV, were immunostained for (A) PDGFRα; (B) MCT10; (C) DAPI counterstaining; or the representative (D) merged image demonstrating co-localization of PDGFRα and MCT10. (E-H) Nkx2.1-GFP+ sorted cells at day 21 of stage VI were immunostained for (E) O4; (F) MCT10; (G) DAPI counterstaining; or the representative (H) merged image demonstrating co-localization of O4 and MCT10. (I-J) Nkx2.1-GFP+ sorted cells at day 21 of stage VI were immunostained for (I) O4; (J) DIO2; (K) DAPI counterstaining; or the representative (L) merged image demonstrates co-localization of O4 and DIO2. (M-P) Nkx2.1-GFP+ sorted cells at day 21 of stage VI were immunostained for (M) O4; (N) DIO3; (O) DAPI counterstaining; or the representative (P) merged image demonstrating co-localization of O4 and DIO3. Scale bars=20 μm.

Figure 12:
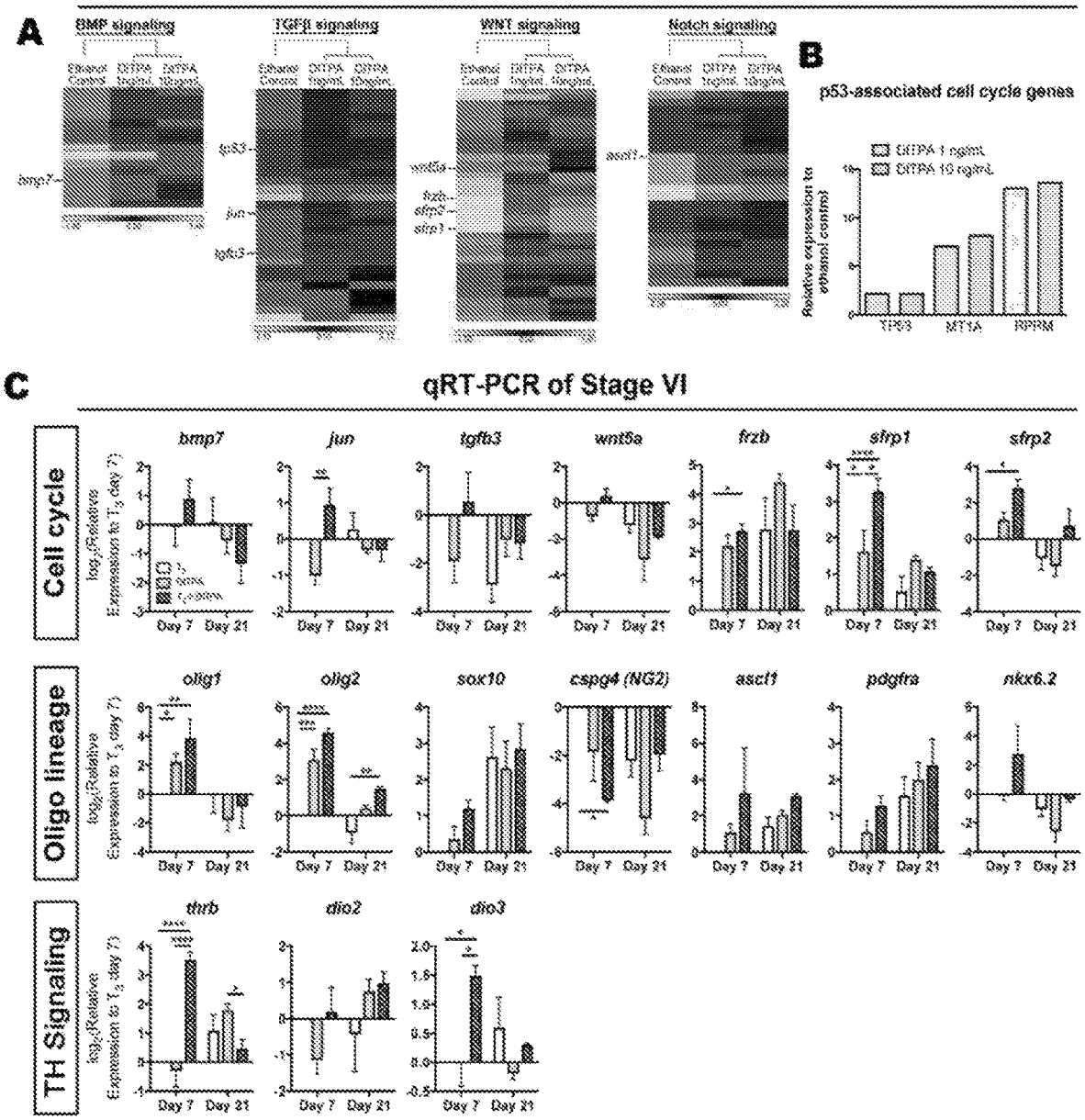

FIG. 12. DITPA Regulates Cell Cycle Associated Signaling Pathways and Associated Genes to Promote OL Development (Related to FIGS. 4 and 5)

(A) Heatmaps derived from microarray analysis (see FIG. 4) using GO term 'BMP signaling', 'TGFβ signaling', 'WNT signaling', and 'Notch signaling'. (B) Expression levels of p53-associated cell cycle genes upon DITPA treatment from microarray analysis showing up-regulation of TP53 (encoding p53), MT1A (encoding metallothionein-1A), and RPRM (encoding reprimo) upon DITPA treatment. (C) qRT-PCR analyses from the different treatment groups at stage VI of hESC-differentiation following the isolation and sorting of the Nkx2.1-GFP+ cells and derivation of maturing OLs (see FIG. 5) showing regulation of cell cycle associated genes (BMP signaling; bmp7, JNK signaling; jun, TGF☐Tsignaling; tgfb3 and WNT signaling; wnt5a, frzb, sfrp1, and sfrp2); OL lineage specific genes (olig1, olig2, sox10, cspg4 (NG2), ascl1, pdgfra, and nkx6.2); and intracellular TH signaling genes (thrb (TR☐(TRdio2, and dio3). Two-way ANOVA with Tukey's post-hoc analysis; *, $P<0.05$;  $P<0.01$; *, $P<0.001$; (n=3; mean ☐ 3; me FIG. 13. DITPA Treatment of Differentiating OPCs Overcomes the Cell Death Initiated by the Pharmacological Blockade of MCT8 Through Bosutinib Oligodendroglial cells derived from the hESC Nkx2.1-GFP+ sorted population at day 21 of stage VI, were treated with $T_3$ alone (50 ng/mL) dissolved in 0.01% of ethanol along with the co-administration of the following concentrations of Bosutinib; 1 ng/mL, 10 ng/mL and 100 ng/mL and Bosutinib 10 ng/mL and 100 ng/mL with the co-administration of 10 ng/mL of DITPA for 48 hours was also performed and all cells analyzed for the cell death. (A) Schematic diagram of the assessment of oligodendroglial cell death upon administration of Bosutinib and Bosutinib with DITPA. (B) Dot plots derived from flow cytometry showing the DAPI+ dead cell numbers upon 48 hours of Bosutinib and Bosutinib with DITPA treatments. (C) Proportions of DAPI+ dead cells (%) among the different treatment groups showing significant reduction in cell death in the oligodendroglial cells treated with DITPA. (D) The cytotoxicity test, MTT assay showed increased survival rates among the hESC-derived oligodendroglial populations that were treated with DITPA. One-way ANOVA with post-hoc Newman-Keuls test; $*P<0.05$; $P<0.01$; $*P<0.001$; (n=3; mean±SEM).

FIG. 14. Transduction of Stage V OPCs from Nkx2.1-GFP-Sorted Cultures with the Lentivirus Carrying slc16a2 shRNA (Related to FIG. 7)

(A) Schematic diagram of the lentivirus (LV) transduction procedure performed prior to apoptosis assay.

(B) qRT-PCR analysis of slc16a2 5 days post-lentivirus transduction. qRT-PCR analyses indicate the log of average fold-change in gene expression compared with no transduction controls Student's t-test; $****P<0.0001$; (n=3; mean±SEM).

FIG. 15. Developmental MCT8 Expression in Oligodendroglia in the Mouse Sub-Ventricular Zone (SVZ), Corpus Callosum (CC) and Optic Nerve (A) Schematic diagram of coronal section of mouse brain showing where images are taken.

(B) Developmental expression of MCT8 in PDGFRα-positive OPCs within the SVZ from p7-84. High magnification images were shown at the right hand side (*V: ventricular zone; scale bar=50 μm). (C) MCT8 expression in CC-1-positive mature oligodendrocytes within the CC at p21 (arrows indicate CC-1-positive oligodendrocytes expressing MCT8; scale bar=20 μm). (D) MCT8 expression in PDGFRα-positive OPCs within the optic nerve from p84 wild-type mouse (scale bar=50 μm).

FIG. 16. Suspected Dysregulation of TH Signalling in MOG35-55-EAE-Induced Wild-Type Mice Spinal Cord and MS Patient (A) Western immunoblotting for MCT8, MCT10, DIO2, and Actin (loading control) of lumbo-sacral spinal cord lysates of naïve, EAE-induced wild-type mice with clinical score 1, 2, and 3. (B-F) Densitometric quantification (AU) of (B) full-length MCT8 (FL-MCT8); (D) ~40 kDa putative degradation product of MCT8; (E) full-length MCT10 (FL-MCT10); (F) ~25 kDa putative degradation product of MCT10; (F) DIO2 over Actin (Data presented as mean±SEM, n=4-5, $*P<0.05$. $P<0.01$, $*P<0.001$, $****P<0.0001$. (G) Western immunoblotting for MCT8, and a-tubulin (loading control), showing reduction in monomeric, and putative oligomeric MCT8 in deep white matter lysates from progressive MS patient.

Maintenance of hESC Culture hESCs (Hes3 and Nkx2.1-GFP reporter cell line derived from Hes3 (Goulburn et al., 2011), were maintained on γ-irradiated mouse embryonic fibroblasts (MEFs) from a 129sv strain (Stemcore, AIBN, The University of Queensland), and dissociated with collagenase type IV (Life technologies) for passaging. They were maintained in serum-free hESC medium; DMEM/F12 (Life Technologies) supplemented with 20% Knockout Serum replacement (Life Technologies), 1× Non-Essential Amino Acids (NEAA) (Life Technologies), 0.5% Penicillin-Streptomycin (Life Technologies), 1× Glutamax (Life Technologies), 55 mM 2-Mercaptoethanol (Life Technologies) and basic fibroblast growth factor (bFGF) (10 ng/mL, Peprotech).

Oligodendrocyte (OL) Differentiation

Published protocols (Chaerkady et al., 2011; Kerr et al., 2010) were utilized for the production of OLs from hESCs with minor modifications.

Stage I; the cells were passaged onto 4% growth factor-reduced Matrigel (BD Biosciences) coated plates with MEF-conditioned medium (hESC medium supernatant without bFGF which were cultured overnight on γ-irradiated MEFs) with additional 10 ng/mL bFGF for a week.

Stage II; hESC cultures were dissociated using collagenase type IV, collected and resuspended in serum-free N2/B27 media (1×DMEM/F12 and 1× Neurobasal medium (Life technologies), 0.5×N2 supplement (Life technologies), 1×B27 supplement (Life technologies), 0.5% Penicillin-Streptomycin, 1× Glutamax and 1×NEAA) supplemented with bFGF (20 ng/mL), FGF4 (20 ng/mL, R&D systems), and Noggin (200 ng/mL, R&D systems). Resuspended cells were then placed onto non-adherent plates (Corning) at a density of 20,000 cells/cm² to form embryoid bodies (EBs), which were grown for 14 days.

Stage III; approximately 50 EBs were plated onto each well of 4% growth factor-reduced Matrigel coated plates and cultured in N2/B27 medium supplemented with bFGF (20 ng/mL, Peprotech) and Sonic hedgehog (shh) (100 ng/mL, R&D systems) for 5 days to differentiate them into neural precursors.

Stage IV; these cells were collected using 100 μL/cm² accutase (Life technologies) and plated at a density of 20,000 cells/cm² onto 4% growth factor-reduced Matrigel coated plates in N2/B27 medium with epidermal growth factor (EGF) (20 ng/mL, R&D systems). These cells were then fed daily for 12 days to induce glial progenitor cells or pre-OPCs.

Stage V; these cells were detached using accutase (Life technologies) and plated at the same density onto 4% growth factor-reduced Matrigel coated plates, in N2/B27 medium with platelet derived growth factor-AA (PDGF-AA) (20 ng/mL, R&D systems) for 14 days to induce OPCs.

Stage VI; for terminal differentiation, these cells were plated onto poly-L-ornithine (10 µg/mL, Sigma-Aldrich) and mouse laminin (10 µg/mL, Life technologies) coated plates in N2/B27 medium supplemented with $T_3$ (50 ng/mL, Sigma-Aldrich) for 21 days to induce pre-OLs.

Rationale for Nkx2.1-Based Sorting

An elegant genetic fate mapping study has uncovered that Nkx2.1+ precursors were the earliest wave of OPCs generated within the mouse ventral forebrain (Kessaris et al., 2006). This evidence prompted the inventors to isolate Nkx2.1+ neural precursors by utilizing the Nkx2.1-GFP hESC reporter line (the biological characteristics of which are described in (Goulburn et al., 2011), the disclosure of which is incorporated into this specification by reference) in an attempt to derive a purified population of OPCs. As expected, Nkx2.1-GFP+ isolated cells demonstrated a higher yield of PDGFRα+/NG2+ OPCs, which provided us with an increased yield of O4+ pre-OLs (following their derivation), when compared with Nkx2.1-GFP− isolated cells or other cell lines that were not sorted for their Nkx2.1 expression early during hESC culture. From these highly enriched OPCs and pre-OLs derived from Nkx2.1+ cells, the inventors identified the expression of MCT8 for the first time. To study the functional role of MCT8 during OL development, the inventors stably knocked down MCT8 in the purified OL cultures using a lentivirus constructed to encode the slc16a2 short hairpin RNA (shRNA), which resulted in significant oligodendroglial cell death and in turn, impaired myelination under co-culture conditions.

Fluorescence-Activated Cell Sorting (FACS)

At the end of stage III, neural precursors were dissociated using accutase (Life technologies) and stained with DAPI (1:2,000, Life Technologies) then resuspended in N2/B27 medium with Rho kinase inhibitor, Y27632 (10 µM, Bioreagent). They were sorted according to Nkx2.1-GFP expression on BD Influx (BD Biosciences), and Hes3-derived neural precursors served as negative controls for GFP expression. The data set was first plotted with forward side scatter (FSC) and side scatter (SSC) to gate single cells and only live cells (excluding DAPI-positive cells) were used for analysis. For post-sort analysis, data was processed using FlowJo software. The sorted cells; GFP-negative and GFP-positive cells were collected in stage IV medium with 10 µM Y27632, and further differentiated.

Live Cell Imaging and Processing

During stage II, the EBs obtained from the Nkx2.1-GFP reporter cell line were captured using a Nikon C1 inverted confocal microscope with a 4× dry objective lens, monitored daily (EBs derived from the Hes3 hESC line served as a negative control for GFP expression). Additionally, z-stack images were captured, processed, and analyzed by Imaris version 7.6.4. The intensity of GFP within a single EB was measured in arbitrary units, while the volume to each of the captured EBs was measured in voxels.

Immunocytochemistry

The cells were grown onto 13 mm glass coverslips which were placed onto 24-well plates coated with 4% growth factor-reduced Matrigel (BD Biosciences) (stage III-V). Whereas, at the OPC differentiation stage (Stage VI) the cells were grown onto 13 mm glass coverslips which were placed in 24-well plates coated with poly-L-ornithine (10 µg/mL, Sigma-Aldrich) and mouse laminin (10 µg/mL, Invitrogen). The glass coverslips were pre-treated with 1 M hydrochloric acid to enhance the cell attachment and autoclaved for sterility. The cells were plated onto the glass coverslip in each well and grown in the appropriate medium according to the stage of differentiation. The cells were fixed with 2% paraformaldehyde (PFA) for 10 minutes at room temperature. They were then washed three times for 10 minutes in 1×PBS and blocked in blocking buffer (5% Normal Donkey Serum, 5% Normal Goat Serum and 0.01% Triton X-100 in 1×PBS). For membranous staining (PDGFRα and NG2), the cells were treated without Triton X-100 in the blocking solution.

The fixed cells were incubated sequentially with primary then secondary antibodies overnight at 4° C. and 1 hour at room temperature, respectively. Primary antibodies used included: polyclonal rabbit anti-GFP (abcam, ab290, 1:500); monoclonal mouse anti-PDGFRα (BD Biosciences, BD556002, 1:200); monoclonal mouse anti-chondroitin sulfate proteoglycan (NG2) (BD Biosciences, BD554275, 1:200); monoclonal mouse anti-O4 (R&D systems, MAB1326, 1:200); polyclonal rabbit anti-myelin basic protein (MBP) (Millipore, AB980, 1:200); monoclonal mouse anti-glial fibrillary acidic protein (GFAP) (Sigma-Aldrich, G6171, 1:100); polyclonal goat anti-Olig2 (R&D systems, AF2418, 1:40), monoclonal mouse anti-Nestin (R&D systems, MAB1259, 1:200); polyclonal rabbit anti-MCT8 (MBL, MBP031, 1:200); monoclonal β-III-tubulin (Covance, MMS-435P, 1:1,000); monoclonal mouse anti-Sox10 (Sigma-Aldrich, SAB1402361, 1:500), polyclonal rabbit anti-MCT10 (US Biological, 041801, 1:200), polyclonal goat anti-DIO2 (Sigma-Aldrich, SAB2500310, 1:200), polyclonal rabbit anti-DIO3 (Abcam, ab82041, 1:100), monoclonal mouse anti-MBP (Millipore, NE1018 1:1000), and polyclonal rabbit anti-NG2 (Millipore, AB5320, 1:200).

Alexa Fluor-labeled secondary antibodies were used including anti-mouse 647 (Invitrogen, A31571, 1:200); anti-rabbit 647 (Invitrogen, A21244, 1:200); anti-goat 555 (Invitrogen, A51432, 1:200); and anti-mouse 555 (Invitrogen, A21422, 1:200). The cells were counterstained with 4',6-diamidino-2-phenylindole (DAPI) (Invitrogen, D1306, 1:2,000). The stained glass coverslips were placed on microscope slides (Thermo Scientific) with a drop of anti-fading fluorescence mounting medium (Dako). The slides were scanned and images were captured on the confocal microscopes (either Nikon C1 Upright or A1 Inverted) using a ×40 oil objective lens. 16-bit images were then converted to RGB images with ImageJ and processed in Adobe Photoshop.

Flow Cytometry

The cells were analyzed by passage through a FACS Canto II flow cytometer or LSR-Fortessa (BD Biosciences), using FACS Diva Software (BD Biosciences) for acquisition and FlowJo version 8.7.3. for post-analysis. For extracellular staining, the cells were detached by accutase and centrifuged at 1500 rpm for 3 minutes. The cell pellet was resuspended in media and filtered through the 20 µm mesh. The cells were washed with FACS buffer (1% bovine serum albumin and 0.01% sodium azide in 1×PBS) then sequentially incubated with primary then secondary antibodies for 30 minutes at 4° C.

After washing, the cells were counterstained with DAPI (1:2000), and analyzed on a flow cytometer for acquisition. The datasets were first plotted with forward scatter (FSC) and side scatter (SSC) to gate single cells and only live cells from single cell populations (i.e. excluding DAPI-positive cells) were used for analysis.

For intracellular staining of EBs at stage II, EBs were collected and the medium was carefully removed. Accutase was added to EBs in a tube to break up the aggregates, whereas the cells were detached by accutase from stage III onwards. The collected cells were washed with intracellular (IC) wash (Perm/Wash Buffer diluted 1:10 in distilled water, BD Biosciences). The cells were fixed and permeabilized by Cytofix/CytoPerm (BD Biosciences) according to the manufacturer's protocol. Then cells were washed with IC wash. These were then incubated subsequently with primary and secondary antibodies for 30 minutes. Primary antibodies included: monoclonal mouse anti-Nestin (R&D systems, MAB1259; 1:200), monoclonal mouse anti-GFAP (Sigma-Aldrich, G6171; 1:200), monoclonal mouse APC-conjugated anti-βIII-tubulin (R&D systems, 101195A), monoclonal mouse APC-conjugated anti-Epcam (BD Biosciences, 347200), monoclonal mouse PE-conjugated anti-PDGFRα (BD Biosciences, 556002), monoclonal mouse APC-conjugated anti-NG2 (R&D systems, FAB2585A), monoclonal mouse anti-O4 (R&D systems, FAB1326P; 1:200), and polyclonal rabbit anti-MCT8 (MBL, BMP031; 1:200). Alexa Fluor-labeled 568 and 647 secondary antibodies (Life Technologies, 1:500) were used. Isotype controls for primary antibodies were used for each experiment to check non-specific binding; mouse $IgG_1$ (BD Biosciences, 550878), APC-conjugated mouse $IgG_{2A}$ (R&D systems, 10003A), mouse IgM (BD Biosciences, 555584), PE-conjugated mouse $IgG_{2A}$ (BD Biosciences, 349053), APC-conjugated mouse IgG1 (BD Biosciences, 555751) and mouse $IgG_{2B}$ (BD Biosciences, 555740).

Quantitative PCR after Reverse Transcription

RNA was isolated from cells by using RNeasy Mini Kit (Qiagen) according to the manufacturer's instruction and treated with DNase-I to remove genomic DNA. The concentrations of total RNA were measured by Nanodrop ND-1000 spectrophotometer v3.7 (Thermo Specific) and complementary DNA (cDNA) was synthesized from 1 µg of total RNA using High-Capacity cDNA Reverse Transcription Kit (Applied Biosystems) according to the manufacturer's instructions. Real-Time Quantitative Reverse Transcription Polymerase Chain Reaction (qRT-PCR) was performed with 5-20 ng of cDNA template, 2× Taqman Gene expression master mix and 20× Taqman probes (Life technologies) on ABI Prism 7900HT Sequence detection system (Applied Biosystems). Gapdh served as an endogenous standard control. The qRT-PCR thermo-cycling reaction was 1 cycle at 50° C. for 2 minutes, 1 cycle at 95° C. for 10 minutes and 40 cycles of 95° C. for 15 seconds, then 60° C. for 1 minute. The threshold cycle ($C_T$) value, which represents the cycle at which the first PCR product is detected, was measured in triplicate and normalized against the endogenous control, GAPDH, to determine the $\Delta C_T$ value. Then the $\Delta C_T$ values of GFP-positive cells were then standardized against the $\Delta C_T$ values of undifferentiated hESCs, derived as relative mRNA expression ($\Delta\Delta C_T$).

Bar graphs illustrating the qRT-PCR analyses in FIG. 2, 3, S1-3 representing the $\log_2$ of the average fold-change in gene expression compared directly to the undifferentiated Stage I hESC or $T_3$-treated cells at day 7 in FIG. 5 and S5.

Accession Number of Taqman Probes Used for qRT-PCR

| Target Gene | Taqman Gene Expression Assay | Accession number |
|---|---|---|
| NKX2.1 | Hs00968940_m1 | NM_001079668.2 |
| MBP | Hs00921945_m1 | NM_001025101.1 |
| OLIG2 | Hs00300164_s1 | NM_005806.3 |
| NES (Nestin) | Hs00707120_s1 | NM_006617.1 |
| OLIG1 | Hs00744293_s1 | NM_138983.2 |
| PAX6 | Hs00240871_m1 | NM_001258462.1 |
| NKX6.2 | Hs00752986_s1 | NM_177400.2 |

-continued

| Target Gene | Taqman Gene Expression Assay | Accession number |
|---|---|---|
| GFAP | Hs00909233_m1 | NM_001242376.1 |
| MAP2 | Hs00258900_m1 | NM_002374.3 |
| CSPG4 (NG2) | Hs00361541_g1 | NM_001897.4 |
| SLC16A2 (MCT8) | Hs00989797_m1 | NM_006517.4 |
| PDGFRα | Hs00998018_m1 | NM_006206.4 |
| SOX10 | Hs00366918_m1 | NM_006941.3 |
| NKX2.2 | Hs00159616_m1 | NM_002509.3 |
| DIO2 | Hs00988260_m1 | NM_001007023.3 |
| DIO3 | Hs00956431_s1 | NM_001362.3 |
| SLC16A10 (MCT10) | Hs01039921_m1 | NM_018593.4 |
| GAPDH | Hs02758991_g1 | NM_002046.4 |
| CDKN1B (P27) | Hs01597588_m1 | NM_004064.3 |
| TP53 | Hs01034249_m1 | NM_000546.5 |
| TNFRSF21 (DR6) | Hs01560899_m1 | NM_014452.4 |
| MYT1 | Hs01027966_m1 | NM_004535.2 |
| PLP1 | Hs00166914_m1 | NM_001128834.1 |
| BMP7 | Hs00233476_m1 | NM_001719.2 |
| JUN | Hs01103582_s1 | NM_002228.3 |
| TGFB3 | Hs01086000_m1 | NM_003239.2 |
| WNT5A | Hs00998537_m1 | NM_003392.4 |
| FRZB | Hs00173503_m1 | NM_001463.3 |
| SFRP1 | Hs00610060_m1 | NM_003012.4 |
| SFRP2 | Hs00293258_m1 | NM_003013.2 |
| ASCL1 | Hs04187546_g1 | NM_004316.3 |
| THRB | Hs00230861_m1 | NM_001128176.2 |

Western Immunoblotting

Cell lysates and medium were collected for protein expression and secretion studies. Briefly whole cell lysates were collected in 1×RIPA buffer (Cell Signaling Technology) with 1× Protease inhibitor and 1× Phosphatase inhibitor cocktails (Calbiochem) and triturated through a 26 G needle. These were incubated at 4° C. for 30 minutes then centrifuged at 15,000 rpm for 20 minutes and supernatants were harvested for protein quantification (Pierce) and immunoblotting. For each sample, 5 µg of each protein was loaded on a 4-12% Bis-Tris gradient Gel (Invitrogen) for electrophoresis in 1×MOPS buffer (Invitrogen), which was then transferred onto a PVDF membrane (Merck/Millipore). Rabbit polyclonal anti-MCT8 (MBL, BMP031, 1:1000) and monoclonal β-actin (Sigma-Aldrich, A2228, 1:40,000) were diluted in 5% skim milk in TBST and subsequently probed using an anti-rabbit HRP-conjugated antibody (Calbiochem, 402335, 1:25,000) and anti-mouse HRP-conjugated (Calbiochem, 402335, 1:40,000) antibodies. The membrane was developed using the ECL prime kit (GE Healthcare) then exposed in the dark room.

Culture and Differentiation of Human OPCs from a Commercially Available Kit (Mixed Neural Cell Cultures)

H9-derived commercially available human neural precursors were cultured and differentiated according to the manufacturer's protocol (Human OPC differentiation kit, Millipore). Briefly, undifferentiated cells were maintained on 4% growth factor-reduced Matrigel (BD Biosciences) for a week in manufacturer provided expansion medium then differentiated on poly-L-ornithine (10 µg/mL, Sigma-Aldrich) and mouse laminin (10 µg/mL, Life Technologies) coated plates for 4 weeks in manufacturer provided medium.

DITPA Administration for Neural Cell Culture

Prior to the experiments with DITPA (Sigma-Aldrich) in the Nkx2.1-GFP reporter cell line, an in vitro toxicology assay based on MTT (Sigma-Aldrich) was performed to test the cellular toxicity of DITPA (at varying concentrations. 1, 10, and 100 ng/mL dissolved in absolute ethanol) on H9-derived OPCs (Millipore) The survival of OPCs and the different gene expression levels upon DITPA treatment were tested. To test the survival of hESC-derived OPCs, GFP+- derived pre-OLs from day 21 of stage VI were treated with DITPA (Sigma-Aldrich) reconstituted in absolute ethanol. The final concentration of ethanol in the culture was controlled at 0.01% since 0.01% of absolute ethanol is known to be ineffective on cell viability. Furthermore, to eliminate possible detrimental effects of ethanol on cells, 0.01% ethanol treatment of cultures served as a negative control.

Microarray Analysis

Raw signal intensity values were subjected to variance stabilization transformation including background correction, $log_2$ transformation and variance stabilization using the lumiR package of R Bioconductor (Du et al., 2008). Since there were fewer arrays of common genes detected in DITPA 100 ng/mL compared to DITPA 1 ng/mL and 10 ng/mL versus ethanol control, all analyses were performed without DITPA 100 ng/mL. Hierarchical clustering with centroid linkage clustering was performed. ANOVA analyses of normalized probe intensity values were performed in Partek Genomic Suite (Partek). ANOVA was used to calculate the significance of variation in normalized expression values between sample-groups, and fold change of gene expression was calculated as mean ratio. Absolute fold changes of 1.5 or more were defined as differentially expressed. Gene ontology enrichment analysis was performed on the list of differentially expressed probes in Partek.

Cell Cycle Analysis with BrdU

Pre-OLs from Nkx2.1-GFP+ sorted cultures at stage VI day 7 and day 21 were pulsed with BrdU for 1 hour. Cells were then treated with DNAse I for 45 minutes then collected using accutase (Life Technologies). Collected cells were fixed and permeabilized and stained with anti-BrdU conjugated with APC for 30 minutes at 4° C. Cells were washed and stained with 7-AAD. Cells were then analyzed on LSR-Fortessa (BD Biosciences). Unpulsed cells and pulsed cells without anti-BrdU staining served as a negative control.

Rat Retinal Ganglion Cell (RGC) Purification

The dissected retinae were digested using papain dissociation system according to the manufacturer's protocol (Worthington). Dissociated cells were then incubated sequentially on two Bandeireia lectin (Sigma-Aldrich)-coated plates to negatively select macrophages and endothelial cells. Cells were then incubated on a monoclonal mouse anti-rat Thy1.1 (202502, BioLegend)-coated plate to positively select RGCs. Plate-bound RGCs were then rinsed off by 0.25% trypsin-EDTA (Life Technologies). Purified RGCs were cultured on 8-well chamber slides at 625,000 cells/well. RGC were reaggregated for 2 days then transferred onto poly-D-lysine and mouse laminin (Invitrogen) coated coverglass in 24-well plates at 80,000 cells/well with RGC growth medium containing 1:1 Neurobasal, DMEM (Life Technologies) supplemented with 5 µg/mL human insulin (Sigma-Aldrich), 40 ng/mL $T_3$, 50 µg/mL N-acetyl-cysteine (Sigma-Aldrich), 1×B-27 supplement (Life Technologies), 10 ng/mL Biotin (Sigma-Aldrich), 100 µg/mL transferrin (Sigma-Aldrich), 16 µg/mL putrescine dihydrochloride (Sigma-Aldrich), 60 ng/mL progesterone (Sigma-Aldrich), 40 ng/mL sodium selenite (Sigma-Aldrich), 100 µg/mL bovine serum albumin (Sigma-Aldrich), 50 ng/mL BDNF (Peprotech), 10 ng/mL CNTF (R&D systems), 4.2 µg/mL forskolin (Sigma-Aldrich).

Co-Culture Myelination Medium

Myelination medium was adopted from (Watkins et al., 2008) consisting of DMEM-high glucose medium (Life Technologies), supplemented with 5 µg/mL human insulin (Sigma-Aldrich), 1 mg/mL apotransferrin (Sigma-Aldrich), 20 mM putrescine (Sigma-Aldrich), 4 µM progesterone (Sigma-Aldrich), 6 µm sodium selenite (Sigma-Aldrich), 50 nM hydrocortisone (Sigma-Aldrich), 1× trace elements B (Cellgro), 50 ng/mL Biotin (Sigma-Aldrich), 272 ng/mL Vitamin B12 (Sigma-Aldrich), 1×B-27 (Invitrogen), 100 ng/mL ceruloplasmin (Enzo Life Sciences), and 1 µM γ-secretase inhibitor (DAPT, Enzo Life Sciences).

Generation of Lentivirus Carrying slc16a2-shRNA psi-LVRU6MP vectors carrying either scrambled shRNA or 4 different shRNA sequences for slc16a2 were generated by Genecopoeia, USA. These vectors have two different promoters, U6 promoter for shRNA and EF1α for the mCherry reporter, and a puromycin resistance for stable selection (8,357 bp). The inventors tested 4 different shRNA sequences for the Nkx2.1-GFP hESC lines and the most efficient slc16a2 shRNA sequence was selected for the generation of lentivirus. The most efficient target sequence for our cells is as follows: GCTTCGCGCCGTAGTCTTA. This specific sequence or scrambled shRNA sequence were packaged into a lentivirus (Genecopoeia).

Pharmacological Blockade of MCT8-Dependent $T_3$ Transport

Pre-OLs from Nkx2.1-GFP+ sorted cultures at stage VI, day 21 were treated with the pharmacological inhibitor of MCT8, bosutinib (LC Laboratories, B-1788, reconstituted in dimethyl sulfoxide, [DMSO]) at different concentrations (1 ng/mL, 10 ng/mL and 100 ng/mL) with co-administration of 10 ng/mL DITPA. An MTT assay and flow cytometry were then performed on the cells stained for DAPI after 48 hours of treatment, to analyze DAPI+ dead cells.

Example 2

In this example, to potentiate oligodendrocyte differentiation, the potential role of DITPA as a therapeutic to overcome myelin abnormalities was studied by the inventors, From this study, it seems that human oligodendrocytes require MCT8 for their maintenance, differentiation and myelination. Furthermore, the major finding of this study is that DITPA is capable of driving oligodendrocyte differentiation and myelination even in the absence of MCT8. To support in vitro oligodendroglial expression of MCT8, the inventors performed an in vivo expression study of MCT8 during postnatal mouse brain development. From this, a specific expression of MCT8 in postnatal OPCs within the sub-ventricular zone (SVZ) during postnatal development, mature oligodendrocytes within the corpus callosum (CC) white matter tract and adult OPCs within the optic nerve were found (FIG. 15). Of interest, MCT8 expression seems to be maintained in cells residing within the SVZ throughout development, suggesting for its role in their maintenance (FIG. 15). Intriguingly, although it requires further validation, it seems that in EAE (an animal model of MS) and MS, local cellular hypothyroidism associated with reduced cellular TH transport is suspected as the expression level of MCT8, MCT10, and DIO2 was found to be reduced during EAE and MS progression (FIG. 16). From a translational perspective, DITPA holds great promise as it has already passed phase I clinical trials for treating patients with AHDS (Verge et al., 2012). Therefore, given enough evidence of dysregulation of TH transport during neuroinflammation, DITPA could well be immediately utilized in an attempt to enhance remyelination in MS.

REFERENCE

Verge, C. F., Konrad, D., Cohen, M., Di Cosmo, C., Dumitrescu, A. M., Marcinkowski, T., Hameed, S., Hamilton, J., Weiss, R. E., and Refetoff, S. (2012). Diiodothyropropionic acid (DITPA) in the treatment of MCT8 deficiency. *J Clin Endocrinol Metab* 97, 4515-4523.

Example 3—Preparation of DITPA for Oral Administration (1.5 mg/kg)

Example for body weight=25 kg.
Total DITPA to give per oral dosing=25 kg×1.5 mg/kg/day=37.5 mg DITPA. This amount would be divided into 3 equal portions, with each portion to be given approximately 8 hours apart on each day. Each portion amounts to a dose of 0.5 mg/kg/day, and for the 25 kg body weight is 12.5 mg DITPA.
The following describes the preparation of a mixture of DITPA for the 0.5 mg/kg dose.
Prepare 6 ml of the DITPA mixture as follows:
1. 15 mg of DITPA was placed into a glass vial.
2. 6 ml of vehicle solution was then added, and the glass vial was capped and the composition was mixed thoroughly with gentle shaking.
3. The composition was a syrupy mixture at a strength of 2.5 mg/ml.
4. The volume of the mixture required for administering the 12.5 mg portion for the 25 kg body weight is therefore, 12.5 mg/2.5 mg·m$^1$=5 ml.
FIG. 1 A is a chart showing body weight and volume of mixture required for the dose of 0.5 mg/kg. This is ⅓ of the daily dose; therefore, it is repeated 3 times a day.

Example 4—Preparation of DITPA for Oral Administration (2 mg/kg)

Example for body weight=25 kg.
Total DITPA to give per oral dosing=25 kg×2 mg/kg/day=50 mg DITPA. This amount is divided into 3 equal portions, with each portion to be given approx 8 hours apart on each day. Each portion amounts to a dose of 0.67 mg/kg/d, and for the 25 kg body weight is 16.7 mg DITPA. The following describes the preparation of a mixture of DITPA for the 0.67 mg/kg dose. Prepare 12 ml of the DITPA mixture as follows:
1. 30 mg of DITPA was placed into a glass vial.
2. Add 12 ml of vehicle solution that is provided, cap the vial and mix thoroughly with gentle shaking.
3. The mixture results as a syrupy mixture at a strength of 2.5 mg/ml.
4. The volume of the mixture required for administering the 16.7 mg portion for the 25 kg body weight is therefore, 16.7 mg/2.5 mg·m$^1$=6.7 ml.
FIG. 1 B is a chart showing body weight and volume of mixture required for the dose of 0.67 mg/kg. This is ⅓ of the daily dose; therefore, repeat this 3 times a day.

Example 6—Preparation of DITPA for Oral Administration (2.67 mg/kg)

Example for body weight=25 kg.
Total DITPA to give per oral dosing=25 kg×2.67 mg/kg/day=66.75 mg DITPA. This amount is divided into 3 equal portions, with each portion to be given approx 8 hours apart on each day. Each portion amounts to a dose of 0.89 mg/kg/d, and for the 25 kg body weight is 22.25 mg DITPA. The following describes the preparation of a mixture of DITPA for the 0.89 mg/kg dose. Prepare 12 ml of the DITPA mixture as follows:
1. 30 mg of DITPA was placed into a glass vial.
2. Add 12 ml of vehicle solution that is provided, cap the vial and mix thoroughly with gentle shaking.
3. The mixture results as a syrupy mixture at a strength of 2.5 mg/ml.
4. The volume of the mixture required for administering the 22.25 mg portion for the 25 kg body weight is therefore, 22.25 mg/2.5 mg·mr$^1$=8.9 ml.
FIG. 1 C is a chart showing body weight and volume of mixture required for the dose of 0.89 mg/kg. This is ⅓ of the daily dose; therefore, repeat this 3 times a day.

Example 7—Preparation of DITPA for Oral Administration (3.56 mg/kg)

Example for body weight=25 kg.
Total DITPA to give per oral dosing=25 kg×3.56 mg/kg/day=89 mg DITPA. This amount is divided into 3 equal portions, with each portion to be given approx 8 hours apart on each day. Each portion amounts to a dose of 1.19 mg/kg/d, and for the 25 kg body weight is 29.67 mg DITPA. The following describes the preparation of a mixture of DITPA for the 1.19 mg/kg dose. Prepare 12 ml of the DITPA mixture as follows:
1. 30 mg of DITPA was placed into a glass vial.
2. Add 12 ml of vehicle solution that is provided, cap the vial and mix thoroughly with gentle shaking.
3. The mixture results as a syrupy mixture at a strength of 2.5 mg/ml.
4. The volume of the mixture required for administering the 29.67 mg portion for the 25 kg body weight is therefore, 29.67 mg/2.5 mg·ml$^{"1}$=11.87 ml.
FIG. 1 D is a chart showing body weight and volume of mixture required for the dose of 1.19 mg/kg. This is ⅓ of the daily dose; therefore, repeat this 3 times a day.

Example 8—Preparation of DITPA for Oral Administration (4.75 mg/kg)

Example for body weight=25 kg.
Total DITPA to give per oral dosing=25 kg×4.75 mg/kg/day=1 18.75 mg DITPA. This amount is divided into 3 equal portions, with each portion to be given approx 8 hours apart on each day. Each portion amounts to a dose of 1.583 mg/kg/d, and for the 25 kg body weight is 39.58 mg DITPA. The following describes the preparation of a mixture of DITPA for the 1.583 mg/kg dose. Prepare 18 ml of the DITPA mixture as follows:
1. 45 mg of DITPA was placed into a glass vial.
2. Add 18 ml of vehicle solution that is provided, cap the vial and mix thoroughly with gentle shaking.
3. The mixture results as a syrupy mixture at a strength of 2.5 mg/ml.
4. The volume of the mixture required for administering the 39.58 mg portion for the 25 kg body weight is therefore, 39.58 mg/2.5 mg·ml$^{"1}$=15.8 ml.
FIG. 1 E is a chart showing body weight and volume of mixture required for the dose of 1.583 mg/kg. This is ⅓ of the daily dose; therefore, repeat this 3 times a day.
  10 ml of vehicle solution comprised 0.25% w/v, sodium carboxymethyl cellulose may be present in an amount of 0.5% w/v and the sodium saccharin may be present in an amount of 0.02%, with water making the balance.

INTERPRETATION OF THIS SPECIFICATION

It will be understood that the invention could take many forms and be put to many different uses. All such forms and uses are embodied within the spirit and scope of the invention, which is to be understood as not being limited to the particular constructional details of the embodiments discussed above, but which extends to each novel feature and combination of features disclosed in or evident from this specification and the accompanying claims and drawings. All of these different combinations constitute various alternative aspects of the invention.

It will also be understood that the term "comprises" (or its grammatical variants), as used in this specification, is equivalent in meaning to the term "includes" and should not be taken as excluding the presence of other elements or features. Further, wherever used in this specification, the term "includes" is not a term of limitation, and is not be taken as excluding the presence of other elements or features.

ABBREVIATIONS

The following is a list of some of the more commonly used abbreviations in this specification, and the expanded term which each abbreviation defines:
AHDS Allan-Herndon-Dudley syndrome
ANOVA Analysis of variance
bFGF Basic fibroblast growth factor
cDNA Complementary deoxyribonucleic acid
CNS Central nervous system
CNTF Ciliary neurotrophic facto
CRT Cellular replacement therapy
DAPI 4',6-diamidino-2-phenylindole, dihydrochloride
DITPA 3'5'-Diiodothyropropionic acid
DNA Deoxyribonucleic acid
EAE Experimental autoimmune encephalitis
EB Embryoid body
EGF Epidermal growth factor
FACS Fluorescence-activated cell sorting
FC Flow cytometry
GAPDH Glyceraldehyde 3-phosphate dehydrogenase
GFAP Glial fibrillary acidic protein
GFP Green fluorescent protein
GPC Glial precursor cell
hESC Human embryonic stem cell
HRP Horseradish peroxidase
ICC Immunocytochemistry
Ig Immunoglobulin
LCI Live cell imaging
MBP Myelin basic protein
MCT8 Monocarboxylate transporter 8
MEF Mouse embryonic fibroblast
MOG Myelin oligodendrocyte glycoprotein MS Multiple sclerosis
NG2 Neuron-glial antigen 2 (Chondroitin Sulfate Proteoglycan 4)
NT3 Neurotrphin-3
NPC Neural precursor cell
NSC Neural stem cell
OL Oligodendrocyte
OPC Oligodendrocyte (Oligodendroglial) precursor cell
PBS Phosphate buffered saline
PCR Polymerase chain reaction
PDGF Platelet-derived growth factor
PDGFRα Platelet-derived growth factor receptor α
PFA Paraformaldehyde
PLP Proteolipid protein
PMD Pelizaeus-Merzbacher disease
PVDF Polyvinylidene fluoride
RGC Rat Ganglion Cell
RNA Ribonucleic acid
rT-PCR Real-time polymerase chain reaction
SCI Spinal cord injury
Shh Sonic Hedgehog
SVZ sub-ventricular zone
T3 Triiodothyronine
T4 Thyroxine
TBST Tris-buffered saline with Tween 20

It is further to be understood that any discussion in this specification of background or prior art documents, devices, acts, information, knowledge or use ('Background Information') is included solely to explain the context of the invention. Any discussions of such Background Information is not be taken as an admission in any jurisdiction that any such Background Information constitutes prior art, part of the prior art base or the common general knowledge in the field of the invention on or before the priority date of the appended claims or any amended claims later introduced into this specification.

The invention claimed is:

1. A method of differentiating a mammalian oligodendrocyte precursor cell into a mammalian oligodendrocyte, the method comprising culturing the mammalian oligodendrocyte precursor cell in a culture medium comprising 3,5-diiodothyropropionic acid (DITPA) at a concentration which is effective to cause the mammalian oligodendrocyte precursor cell to differentiate into a mammalian oligodendrocyte, wherein the mammalian oligodendrocyte precursor cell was obtained through differentiation from a mammalian embryonic stem cell.

2. The method of claim 1, wherein the mammalian embryonic stem cell is human.

3. The method of claim 1 wherein the mammalian embryonic stem cell is a human embryonic stem cell comprising a transgene encoding a green fluorescent protein (GFP) operably linked to a Nkx2.1 promoter or a HES3 reporter cell comprising a transgene encoding a GFP.

4. The method of claim 1 wherein the mammalian embryonic stem cell is an H9 human embryonic stem cell.

5. The method of claim 1, wherein the mammalian oligodendrocyte is capable of myelinating a neuron in a human subject.

6. The method of claim 1, wherein the culture medium comprises between 1 ng/mL and 100 ng/mL DITPA.

7. The method of claim 1, further comprising differentiating mammalian embryonic stem cells to obtain the mammalian oligodendrocyte precursor cell, the method comprising:
   (i) culturing the mammalian embryonic stem cells in the presence of FGF2 so that a three-dimensional mass of cells form;
   (ii) culturing the three-dimensional mass of cells in the presence of FGF2, FGF4, and noggin so that an embryoid body forms;
   (iii) culturing the embryoid body in the presence of sonic hedgehog (shh) and FGF2 so that neural precursor cells form from cells of the embryoid body;
   (iv) adding EGF to the culture of (iii) so that glial precursor cells form from the neural precursor cells; and
   (v) adding PDFG to the culture of (iv) so that oligodendrocyte precursor cells form from the glial precursor cells;
   wherein the culturing of the oligodendrocyte precursor cells in the medium comprising DITPA forms an oligodendrocyte that is a post-mitotic oligodendrocyte capable of myelination.

8. The method of claim 7, wherein the mammalian embryonic stem cell is a human embryonic stem cell comprising a transgene encoding a GFP operably linked to a Nkx2.1 promoter or a HES3 reporter cell comprising a transgene encoding a GFP.

9. A human oligodendrocyte precursor cell in a culture medium comprising DITPA at a concentration which is effective to cause the human oligodendrocyte precursor cell to differentiate into a human oligodendrocyte, wherein the human oligodendrocyte precursor cell was obtained through differentiation of a human embryonic stem cell and the human embryonic stem cell is a human embryonic stem cell comprising a transgene encoding GFP operably linked to a Nkx2.1 promoter or a HES3 reporter cell comprising a transgene encoding a GFP.

10. A cell line comprising a human oligodendrocyte precursor cell in a culture medium comprising DITPA at a concentration which is effective to cause the human oligodendrocyte precursor cell to differentiate into a human oligodendrocyte, wherein the human oligodendrocyte precursor cell was obtained through differentiation of a human embryonic stem cell and the human embryonic stem cell is a human embryonic stem cell comprising a transgene encoding GFP operably linked to a Nkx2.1 promoter or a HES3 reporter cell comprising a transgene encoding a GFP.

* * * * *